United States Patent
Hotson et al.

(10) Patent No.: US 11,040,040 B2
(45) Date of Patent: Jun. 22, 2021

(54) METHODS OF TREATING CANCER

(71) Applicant: Corvus Pharmaceuticals, Inc., Burlingame, CA (US)

(72) Inventors: Andrew Hotson, Burlingame, CA (US); Richard A. Miller, Portola Valley, CA (US); Ian Mccaffery, Oakland, CA (US); Stephen Willingham, Sunnyvale, CA (US)

(73) Assignee: Corvus Pharmaceuticals, Inc., Burlingame, CA (US)

(*) Notice: Subject to any disclaimer, the term of this patent is extended or adjusted under 35 U.S.C. 154(b) by 0 days.

(21) Appl. No.: 16/500,041

(22) PCT Filed: Apr. 4, 2018

(86) PCT No.: PCT/US2018/026105
§ 371 (c)(1),
(2) Date: Oct. 1, 2019

(87) PCT Pub. No.: WO2018/187484
PCT Pub. Date: Oct. 11, 2018

(65) Prior Publication Data
US 2020/0297728 A1    Sep. 24, 2020

Related U.S. Application Data

(60) Provisional application No. 62/481,537, filed on Apr. 4, 2017, provisional application No. 62/514,598, filed on Jun. 2, 2017, provisional application No. 62/582,250, filed on Nov. 6, 2017.

(51) Int. Cl.
*C07K 16/28* (2006.01)
*A61K 31/519* (2006.01)

(52) U.S. Cl.
CPC ........ *A61K 31/519* (2013.01); *C07K 16/2827* (2013.01)

(58) Field of Classification Search
CPC ............ A61K 39/39558; A61K 31/519; A61K 2300/00; A61P 35/00; C07K 16/2827
See application file for complete search history.

(56) References Cited

U.S. PATENT DOCUMENTS

| | | |
|---|---|---|
| 7,405,219 B2 | 7/2008 | Gillespie et al. |
| 7,589,097 B2 | 9/2009 | Gillespie et al. |
| 8,450,328 B2 | 5/2013 | Bamford et al. |
| 8,987,279 B2 | 3/2015 | Bamford et al. |
| 9,376,443 B2 | 6/2016 | Bamford et al. |
| 9,765,080 B2 | 9/2017 | Bamford et al. |
| 2011/0172252 A1 | 7/2011 | Bamford et al. |
| 2019/0076433 A1 | 3/2019 | Willingham et al. |

FOREIGN PATENT DOCUMENTS

| | | |
|---|---|---|
| WO | WO-2009/156737 A1 | 12/2009 |
| WO | WO-2017/011831 A1 | 1/2017 |
| WO | WO-2017/112917 A1 | 6/2017 |
| WO | WO-2018/187484 A1 | 10/2018 |

OTHER PUBLICATIONS

McCaffery, et al, Biomarker and Clinical Activity of CPI-444, a Novel Small Molecule Inhibitor of A2A Receptor (A2AR), in a Ph 1b Study in Advanced Cancers, Annals of Oncology (Supplement 6), vol. 27, pp. 1 (2016). (Year: 2016).*
Beavis, P.A. et al. (2015, e-published Feb. 11, 2015). "Adenosine Receptor 2A Blockade Increases the Efficacy of Anti-PD-1 through Enhanced Antitumor T-cell Responses." *Cancer Immunol Res*; 3(5):506-517.
Gotwals, P. et al. (2017), "Prospects for combining targeted and conventional cancer therapy with immunotherapy." *Nat Rev Cancer* 17, 286-301.
Herbst, Roy S. et al. (2014). "Predictive correlates of response to the anti-PD-L1 antibody MPDL3280A in cancer patients," Nature, vol. 515, No. 7528, pp. 563-567.
International Search Report and Written Opinion issued in International Application No. PCT/US2016/68459, dated Mar. 16, 2017 (Mar. 16, 2017). 12 pages.
International Search Report and Written Opinion issued in International Application No. PCT/US2018/26105, dated Jul. 20, 2018 (Jul. 20, 2018). 15 pages.
Leone, R. D. et al. (2015, e-published Apr. 8, 2015). "A2aR antagonists: Next generation checkpoint blockade for cancer immunotherapy." *Computational and Structural Biotechnology Journal*, 13, 265-272.
Linehan et al. (2013). "Non-Clear Cell Renal Cancer: Disease-Based Management and Opportunities for Targeted Therapeutic Approaches." Semin Oncol. Aug. 2013; 40(4): 511-520.
Loi, S. et al. (2013), "CD73 promotes anthracycline resistance and poor prognosis in triple negative breast cancer," Proceedings of the National Academy of Sciences, 110(27):11091-11096.

(Continued)

*Primary Examiner* — Erich A Leeser
(74) *Attorney, Agent, or Firm* — Mintz, Levin, Cohn, Ferris, Glovsky and Popeo, P.C.

(57) ABSTRACT

Provided herein are, inter alia, methods of treating a cancer tumor in a subject in need thereof, the method comprising administering to the subject a therapeutically effective amount of an adenosine A2A receptor antagonist, wherein the subject comprises an elevated level of CD8+ tumor infiltrating lymphocytes relative to a control, the subject comprises an elevated level of T-effector gene signature relative to a control, the subject comprises an increased cancer tumor T cell receptor diversity or blood T cell receptor diversity relative to a control, the cancer tumor comprises an elevated level of PD-L1 relative to a control, and/or the cancer tumor or the blood of the subject comprises an elevated level of CD73 relative to a control. Further provided are, inter alia, methods for determining whether a subject is likely to, is, or has responded to anti-cancer therapy comprising an A2A receptor antagonist.

15 Claims, 18 Drawing Sheets

(56) References Cited

OTHER PUBLICATIONS

Mahoney et al. (2015). "Combination cancer immunotherapy and new immunomodulatory targets", Nature Reviews Drug Discovery, vol. 14, Aug. 2015 (Aug. 2015), pp. 561-585.

Mediavilla-Varela, Melanie et al. (2013) "Antagonism of adenosine A2A receptor expressed by lung adenocarcinoma tumor cells and cancer associated fibroblasts inhibits their growth," Cancer Biology & Therapy, 14:9. 9, 860-868.

Mittal, D. et al. (2014, e-published Jul. 1, 2014), "Antimetastatic Effects of Blocking PD-1 and the Adenosine A2A Receptor," Cancer Research, 74(14); 3652-3658.

Partial Supplementary European Search Report issued in European Application No. 18781701.0, dated Dec. 9, 2020 (Dec. 9, 2020). 20 pages.

Powles, Thomas et al. (2014), "MPDL3280A (anti-PD-L1) treatment leads to clinical activity in metastatic bladder cancer," Nature, 515(7528); pp. 558-562.

Swart, M. et al. (2016), "Combination Approaches with Immune-Checkpoint Blockade in Cancer Therapy," Frontiers of Oncology, vol. 6:233, pp. 1-16.

Young, A. et al. (2016), "Co-inhibition of CD73 and A2AR Adenosine Signaling Improves Anti-tumor Immune Responses," Cancer Cell 30(3), 391-403.

\* cited by examiner

| | Renal Cell Cancer (N=64) | Non-Small Cell Lung Cancer (N=60) |
|---|---|---|
| Prior anti-PD-(L)1 exposure | | |
| Naive | 19 (30%) | 4 (7%) |
| Resistant/Refractory | 45 (70%) | 56 (93%) |
| PD-L1 Negative | | |
| Determined by FDA-Approved Assay (SP142, cutoff = 5%) | 90% | 61% |
| Median time since IO agent, months (range) | 2 (1 – 70) | 3 (1 – 23) |
| Histology | | |
| Squamous | -- | 20 (33%) |
| Non-Squamous | -- | 40 (67%) |
| Adverse Prognostic Factors (%) | | |
| Visceral metastases | 90% | -- |
| Hepatic metastases | 17% | -- |
| Anemia | 47% | -- |
| Elevated LDH | 19% | -- |
| Median age, years (range) | 66 (44-70) | 70 (41-85) |
| No. of patients single agent / No. of patients combination | 33/31 | 30/30 |
| Median number prior therapies | 3 (1-5) | 2 (1-5) |

FIG. 11

All Adverse Events ≥ 5% Frequency (n=75)

| | Single Agent (%) | Combination (%) |
|---|---|---|
| Fatigue | 21 | 30 |
| Nausea | 11 | 12 |
| Pruritus | 10 | 11 |
| Diarrhea | 7 | 6 |
| Anemia | 7 | -- |
| Decreased Appetite | 6 | 9 |
| Pyrexia | 5 | 8 |
| Rash | -- | 6 |
| Cough | -- | 5 |
| Vomiting | -- | 5 |

Grade ≥ 3 Serious Adverse Events

- Single agent (n=1)
  - Gr 3 nausea-vomiting-diarrhea

- Combination CPI-444 + atezolizumab (n=5)
  - Gr 3 immune-related hepatitis, dermatitis, mucositis, pneumonitis
  - Gr 3 autoimmune hemolytic anemia
  - Gr 3 increased ALT/AST
  - Gr 3 thrombocytopenia/Gr 4 encephalitis
  - Gr 3 pneumonitis

FIG. 12

METHODS OF TREATING CANCER

CROSS-REFERENCE TO RELATED APPLICATIONS

This application is a Section 371 US national phase of International Application No. PCT/US2018/26105 filed Apr. 4, 2018, which claims priority to U.S. Application No. 62/582,250 filed Nov. 6, 2017; U.S. Application No. 62/514,598 filed Jun. 2, 2017; and U.S. Application No. 62/481,537 filed Apr. 4, 2017, the disclosures of which are incorporated by reference herein in their entirety and for all purposes.

BACKGROUND

The goal of immunotherapy is to drive cytotoxic T-cell responses to eradicate cancer. To prevent reaction to self-antigens, or overreaction, multiple inhibitory checkpoint signals exist including PD1/2, CTLA4 and adenosine. Extracellular adenosine, a purine nucleoside, is produced during acute, inflammatory processes by conversion from adenosine triphosphate (ATP) through ectonucleotidases CD73 and CD39 expressed on the cell surface of multiple tissue types. Adenosine is normally upregulated to protect a host from over-injury in response to such stimuli as infection or ischemia by binding its extracellular, G-protein coupled receptors on target cells (including MR, A2AR, A2BR, and A3R) and begin healing {Hasko 2008}. However, multiple tumor types can actively sustain extracellular adenosine levels well beyond acute phase reactions to dampen a host's immune response through multiple mechanisms {Antionioli 2013}. Increases in adenosine in the microenvironment by malignant cells recruits regulatory T-cells (Tregs), which express substantial CD39, to the area and further drive up adenosine levels {Sica 2010}.

Cancer cells also appear to directly utilize adenosine. As a result, adenosine causes inefficient presentation of tumor antigens to the adaptive system and enhances tumor growth. Thus, there is a need in the art for effective cancer treatments. The methods and compositions provided herein address these and other deficiencies in the art.

BRIEF SUMMARY

Provided herein are, inter alia, methods and compositions for selecting subjects for certain cancer treatments, identifying subjects who may benefit from certain cancer treatments, and treating cancer, such as lung cancer (e.g., non-small cell lung cancer), melanoma (e.g., malignant melanoma), breast cancer (e.g., triple negative breast cancer), colorectal cancer, renal cancer, bladder cancer, head and neck cancer, and prostate cancer.

Provided herein are methods and compositions for activating T cells, increasing an anti-tumor immune response, increasing the amount of CD8-positive cells relative to the amount of regulatory T cells, enhancing anti-tumor immune memory, and/or increasing global immune activation in a subject. In embodiments, provided herein are methods for detecting a patient who is likely to be refractory or resistant to monotherapy comprising a PD-1 pathway inhibitor. In embodiments, methods included herein identify subjects who are particularly likely to respond to treatment with an adenosine-A2A receptor antagonist. In embodiments, methods included herein identify subjects who are likely to respond to treatment comprising both an A2A receptor antagonist and a PD-1 pathway inhibitor. In embodiments, the PD-1 pathway inhibitor is atezolizumab.

In an aspect, a method of treating a cancer tumor in a subject in need thereof is provided. The method includes administering to the subject a therapeutically effective amount of an adenosine-A2A receptor antagonist. The subject comprises an elevated level of tumor infiltrating lymphocytes (TILs) (such as infiltrating CD8 T cells, e.g., within the cancer tumor) relative to a control, increased T cell receptor diversity in the blood or cancer tumor relative to a control, the cancer tumor comprises an elevated level of PD-L1 relative to a control, and/or the cancer tumor or a bodily fluid (e.g., whole blood, plasma, or serum) of the subject comprises an elevated level of CD73 relative to a control. In embodiments, the subject comprises an elevated level of a T cell gene signature (e.g., in the cancer tumor) relative to a control. In embodiments, the tumor infiltrating lymphocytes are CD8 T cells. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of treating a cancer tumor in a subject in need thereof is provided. The method includes (i) determining whether (a) the cancer tumor comprises elevated levels of tumor infiltrating lymphocytes (such as CD8) relative to a control, (b) the subject comprises an increased cancer tumor T cell receptor diversity or blood T cell receptor diversity relative to a control, (c) the cancer tumor comprises an elevated level of PD-L1 relative to a control, (d) the subject has an increased level of a T-effector signature compared to a control, and/or (e) the cancer tumor or a bodily fluid (e.g., whole blood, plasma, or serum) of the subject comprises an elevated level of CD73 relative to a control; and (ii) administering to the subject a therapeutically effective amount of an adenosine-A2A receptor antagonist. In embodiments, the tumor infiltrating lymphocytes are CD8 T cells. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of treating a cancer tumor in a subject in need thereof is provided. In embodiments, the cancer tumor comprises an elevated level of tumor infiltrating lymphocytes relative to a control, the subject comprises increased T cell receptor diversity in the blood or cancer tumor relative to a control, the cancer tumor comprises an elevated level of PD-L1 relative to a control, and/or the cancer tumor or a bodily fluid (e.g., whole blood, plasma, or serum) of the subject comprises an elevated level of CD73 relative to a control. In embodiments, the cancer tumor comprises an elevated level of a T cell gene signature relative to a control. The method includes administering to the subject a therapeutically effective amount of an adenosine-A2A receptor antagonist. In embodiments, the tumor infiltrating lymphocytes are CD8 T cells. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of treating a cancer tumor in a subject in need thereof is provided. In embodiments, the cancer tumor comprises an elevated level of tumor infiltrating lymphocytes relative to a control, the subject comprises increased T cell receptor diversity in the blood or cancer tumor relative to a control, the cancer tumor comprises an elevated level of PD-L1 relative to a control, and/or the cancer tumor or a bodily fluid (e.g., whole blood, plasma, or serum) of the subject comprises an elevated level of CD73 relative to a control. In embodiments, the cancer tumor comprises an elevated level of a T cell gene signature relative to a control. In embodiments, the tumor infiltrating lymphocytes are CD8 T cells. The method includes administering to the subject a therapeutically effective amount of an adenosine-A2A receptor antagonist of formula:

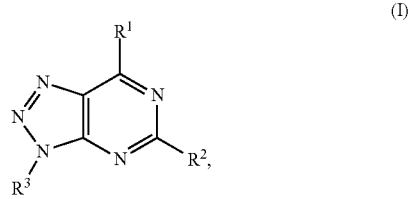

(I)

wherein the substituents are as defined herein. In embodiments, the adenosine-A2A receptor antagonist is a compound of formula (II). In embodiments, the adenosine-A2A receptor antagonist is a compound of formula (III). In embodiments, the adenosine-A2A receptor antagonist is a compound of formula (IIIA), a compound of formula (TIM), or a mixture thereof. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of activating a T cell is provided. In embodiments, the T cell is in a subject. In embodiments, the subject comprises an elevated level of tumor infiltrating lymphocytes (e.g., within a cancer tumor) relative to a control, increased T cell receptor diversity in the blood or a cancer tumor relative to a control, a cancer tumor that comprises an elevated level of PD-L1 relative to a control, and/or a cancer tumor or a bodily fluid (e.g., whole blood, plasma, or serum) that comprises an elevated level of CD73 relative to a control. In embodiments, the subject comprises an elevated level of a T cell gene signature (e.g., in a cancer tumor) relative to a control. In embodiments, the tumor infiltrating lymphocytes are CD8 T cells. The method includes contacting the T cell with an A2A receptor antagonist, wherein the A2A receptor antagonist is a compound of formula:

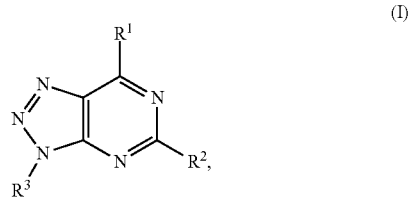

(I)

wherein the substituents are as defined herein. In embodiments, the adenosine-A2A receptor antagonist is a compound of formula (II). In embodiments, the adenosine-A2A receptor antagonist is a compound of formula (III). In embodiments, the adenosine-A2A receptor antagonist is a compound of formula (IIIA), a compound of formula (TIM), or a mixture thereof. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of inhibiting A2A receptor activity of a cell is provided. In embodiments, the cell is within a subject. In embodiments, the subject comprises an elevated level of tumor infiltrating lymphocytes (e.g., within a cancer tumor) relative to a control, increased T cell receptor diversity in the blood or a cancer tumor relative to a control, a cancer tumor that comprises an elevated level of PD-L1 relative to a control, and/or a cancer tumor or a bodily fluid (e.g., whole blood, plasma, or serum) that comprises an elevated level of CD73 relative to a control. In embodiments, the subject comprises an elevated level of a T cell gene signature (e.g., in a cancer tumor) relative to a control. In embodiments, the tumor infiltrating lymphocytes are CD8 T cells. The method includes contacting the cell with an A2A receptor antagonist, wherein the A2A receptor antagonist is a compound of formula:

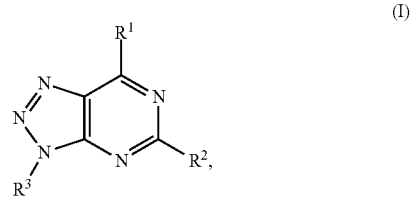

(I)

wherein the substituents are as defined herein. In embodiments, the adenosine-A2A receptor antagonist is a compound of formula (II). In embodiments, the adenosine-A2A receptor antagonist is a compound of formula (III). In embodiments, the adenosine-A2A receptor antagonist is a compound of formula (IIIA), a compound of formula (IIIB), or a mixture thereof. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of increasing an anti-tumor immune response in a subject in need thereof is provided. In embodiments, the subject comprises an elevated level of tumor infiltrating lymphocytes (e.g., within a cancer tumor) relative to a control, increased T cell receptor diversity in the blood or a cancer tumor relative to a control, a cancer tumor that comprises an elevated level of PD-L1 relative to a control, and/or a cancer tumor or a bodily fluid (e.g., whole blood, plasma, or serum) that comprises an elevated level of CD73 relative to a control. In embodiments, the subject comprises an elevated level of a T cell gene signature (e.g., in a cancer tumor) relative to a control. In embodiments, the tumor infiltrating lymphocytes are CD8 T cells. The method includes administering to the subject a therapeutically effective amount of an adenosine-A2A receptor antagonist and a programmed cell death protein 1 (PD-1) signaling pathway inhibitor. In embodiments, the PD-1 pathway inhibitor is atezolizumab. In embodiments, the methods further comprise administering an anti-cancer agent.

In an aspect, a method of increasing an anti-tumor immune response in a subject in need thereof is provided. In embodiments, the subject comprises an elevated level of tumor infiltrating lymphocytes (e.g., within a cancer tumor) relative to a control, increased T cell receptor diversity in the blood or a cancer tumor relative to a control, a cancer tumor that comprises an elevated level of PD-L1 relative to a control, and/or a cancer tumor or a bodily fluid (e.g., whole blood, plasma, or serum) that comprises an elevated level of CD73 relative to a control. In embodiments, the subject comprises an elevated level of a T cell gene signature (e.g., in a cancer tumor) relative to a control. In embodiments, the tumor infiltrating lymphocytes are CD8 T cells. The method includes administering to the subject a therapeutically effective amount of an adenosine-A2A receptor antagonist, wherein the A2A receptor antagonist is a compound of formula:

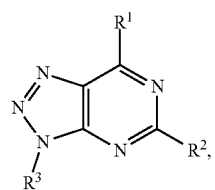

(I)

wherein the substituents are as defined herein. In embodiments, the adenosine-A2A receptor antagonist is a compound of formula (II). In embodiments, the adenosine-A2A receptor antagonist is a compound of formula (III). In embodiments, the adenosine-A2A receptor antagonist is a compound of formula (IIIA), a compound of formula (TIM), or a mixture thereof. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of increasing the amount of CD8-positive cells relative to the amount of regulatory T cells in a subject in need thereof is provided. In embodiments, the subject comprises an elevated level of tumor infiltrating lymphocytes (e.g., within a cancer tumor) relative to a control, increased T cell receptor diversity in the blood or a cancer tumor relative to a control, a cancer tumor that comprises an elevated level of PD-L1 relative to a control, and/or a cancer tumor or a bodily fluid (e.g., whole blood, plasma, or serum) that comprises an elevated level of CD73 relative to a control. In embodiments, the subject comprises an elevated level of a T cell gene signature (e.g., in a cancer tumor) relative to a control. In embodiments, the tumor infiltrating lymphocytes are CD8 T cells. The method includes administering to the subject a therapeutically effective amount of an adenosine-A2A receptor antagonist and a programmed cell death protein 1 (PD-1) signaling pathway inhibitor. In embodiments, the PD-1 pathway inhibitor is atezolizumab. In embodiments, the methods further comprise administering an anti-cancer agent.

In an aspect, a method of increasing the amount of CD8-positive cells relative to the amount of regulatory T cells in a subject in need thereof is provided. In embodiments, the subject comprises an elevated level of tumor infiltrating lymphocytes (e.g., within a cancer tumor) relative to a control, increased T cell receptor diversity in the blood or a cancer tumor relative to a control, a cancer tumor that comprises an elevated level of PD-L1 relative to a control, and/or a cancer tumor or a bodily fluid (e.g., whole blood, plasma, or serum) that comprises an elevated level of CD73 relative to a control. In embodiments, the subject comprises an elevated level of a T cell gene signature (e.g., in a cancer tumor) relative to a control. In embodiments, the tumor infiltrating lymphocytes are CD8 T cells. The method includes administering to the subject a therapeutically effective amount of an adenosine-A2A receptor antagonist, wherein the A2A receptor antagonist is a compound of formula:

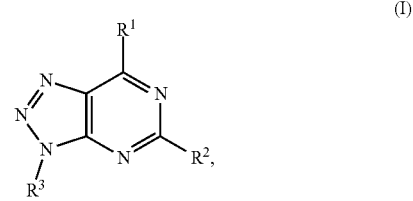

(I)

wherein the substituents are as defined herein. In embodiments, the adenosine-A2A receptor antagonist is a compound of formula (II). In embodiments, the adenosine-A2A receptor antagonist is a compound of formula (III). In embodiments, the adenosine-A2A receptor antagonist is a compound of formula (IIIA), a compound of formula (TIM), or a mixture thereof. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of decreasing tumor volume in a subject in need thereof is provided. In embodiments, the tumor comprises an elevated level of tumor infiltrating lymphocytes relative to a control, the subject comprises increased T cell receptor diversity in the blood or tumor relative to a control, the tumor comprises an elevated level of PD-L1 relative to a control, and/or the tumor comprises an elevated level of CD73 relative to a control. In embodiments, the tumor comprises an elevated level of a T cell gene signature relative to a control. In embodiments, the tumor infiltrating lymphocytes are CD8 T cells. The method includes administering to the subject a therapeutically effective amount of an adenosine-A2A receptor antagonist and a programmed cell death protein 1 (PD-1) signaling pathway inhibitor. In embodiments, the PD-1 pathway inhibitor is atezolizumab. In embodiment, the methods further comprise administering an anti-cancer agent.

In an aspect, a method of decreasing tumor volume in a subject in need thereof is provided. In embodiments, the tumor comprises an elevated level of tumor infiltrating lymphocytes relative to a control, the subject comprises increased T cell receptor diversity in the blood or tumor relative to a control, the tumor comprises an elevated level of PD-L1 relative to a control, and/or the tumor or a bodily fluid (e.g., whole blood, plasma, or serum) of the subject comprises an elevated level of CD73 relative to a control. In embodiments, the tumor comprises an elevated level of a T cell gene signature relative to a control. In embodiments, the tumor infiltrating lymphocytes are CD8 T cells. The method includes administering to the subject a therapeutically effective amount of an adenosine-A2A receptor antagonist, wherein the A2A receptor antagonist is a compound of formula:

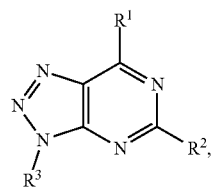

(I)

wherein the substituents are as defined herein. In embodiments, the adenosine-A2A receptor antagonist is a compound of formula (II). In embodiments, the adenosine-A2A receptor antagonist is a compound of formula (III). In embodiments, the adenosine-A2A receptor antagonist is a compound of formula (IIIA), a compound of formula (TIM), or a mixture thereof. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of enhancing anti-tumor immune memory in a subject in need thereof is provided. In embodiments, the tumor comprises an elevated level of tumor infiltrating lymphocytes relative to a control, the subject comprises increased T cell receptor diversity in the blood or tumor relative to a control, the tumor comprises an elevated level of PD-L1 relative to a control, and/or the tumor or a bodily fluid (e.g., whole blood, plasma, or serum) of the subject comprises an elevated level of CD73 relative to a control. In embodiments, the tumor comprises an elevated level of a T cell gene signature relative to a control. In embodiments, the tumor infiltrating lymphocytes are CD8 T cells. The method includes administering to the subject a therapeutically effective amount of an adenosine-A2A receptor antagonist and a programmed cell death protein 1 (PD-1) signaling pathway inhibitor. In embodiments, the PD-1 pathway inhibitor is atezolizumab. In embodiments, the methods further comprise administering an anti-cancer agent.

In an aspect, a method of enhancing anti-tumor immune memory in a subject in need thereof is provided. In embodiments, the tumor comprises an elevated level of tumor infiltrating lymphocytes relative to a control, the subject comprises increased T cell receptor diversity in the blood or tumor relative to a control, the tumor comprises an elevated level of PD-L1 relative to a control, and/or the tumor or a bodily fluid (e.g., whole blood, plasma, or serum) of the subject comprises an elevated level of CD73 relative to a control. In embodiments, the tumor comprises an elevated level of a T cell gene signature relative to a control. In embodiments, the tumor infiltrating lymphocytes are CD8 T cells. The method includes administering to the subject a therapeutically effective amount of an adenosine-A2A receptor antagonist, wherein the A2A receptor antagonist is a compound of formula:

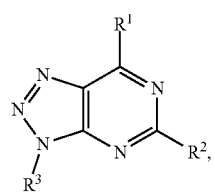

(I)

wherein the substituents are as defined herein. In embodiments, the adenosine-A2A receptor antagonist is a compound of formula (II). In embodiments, the adenosine-A2A receptor antagonist is a compound of formula (III). In embodiments, the adenosine-A2A receptor antagonist is a compound of formula (IIIA), a compound of formula (TIM), or a mixture thereof. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of increasing global immune activation in a subject in need thereof is provided. In embodiments, the subject comprises an elevated level of tumor infiltrating lymphocytes (e.g., within a cancer tumor) relative to a control, increased T cell receptor diversity in the blood or a cancer tumor relative to a control, a cancer tumor that comprises an elevated level of PD-L1, relative to a control, and/or the tumor or a bodily fluid (e.g., whole blood, plasma, or serum) of the subject comprises an elevated level of CD73 relative to a control. In embodiments, the subject comprises an elevated level of a T cell gene signature (e.g., in a cancer tumor) relative to a control. In embodiments, the tumor infiltrating lymphocytes are CD8 T cells. The method includes administering to the subject a therapeutically effective amount of an adenosine-A2A receptor antagonist, wherein the A2A receptor antagonist is a compound of formula:

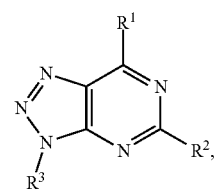

(I)

wherein the substituents are as defined herein. In embodiments, the adenosine-A2A receptor antagonist is a compound of formula (II). In embodiments, the adenosine-A2A receptor antagonist is a compound of formula (III). In embodiments, the adenosine-A2A receptor antagonist is a compound of formula (IIIA), a compound of formula (IIIB), or a mixture thereof. In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of treating a cancer tumor in a subject in need thereof is provided. In embodiments, the cancer tumor comprises an elevated level of tumor infiltrating lymphocytes relative to a control, the subject comprises increased T cell receptor diversity in the blood or cancer tumor relative to a control, the cancer tumor comprises an elevated level of PD-L1 relative to a control, and/or the cancer tumor or the blood of the subject comprises an elevated level of CD73 relative to a control. In embodiments, the cancer tumor comprises an elevated level of a T cell gene signature relative to a control. In embodiments, the tumor infiltrating lymphocytes are CD8 T cells. The method includes administering to the subject a therapeutically effective amount of an adenosine-A2A receptor antagonist of formula:

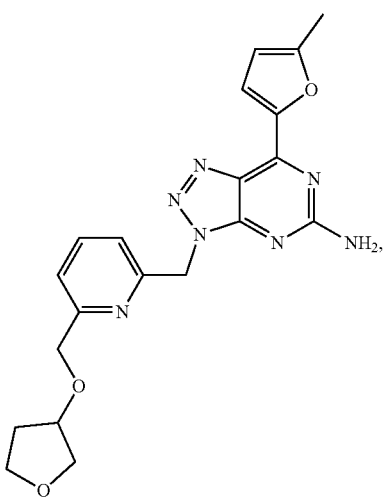

wherein the adenosine-A2A receptor antagonist is administered at 100 mg twice a day (BID). In embodiments, the methods further comprise administering a therapeutically effective amount of: (i) a PD-1 pathway inhibitor; (ii) an anti-cancer agent; or (iii) a PD-1 pathway inhibitor and an anti-cancer agent. In embodiments, the PD-1 pathway inhibitor is atezolizumab.

In an aspect, a method of treating a cancer tumor in a subject in need thereof is provided. In embodiments, the cancer tumor comprises an elevated level of tumor infiltrating lymphocytes relative to a control, the subject comprises increased T cell receptor diversity in the blood or cancer tumor relative to a control, the cancer tumor comprises an elevated level of PD-L1 relative to a control, and/or the cancer tumor or the blood of the subject comprises an elevated level of CD73 relative to a control. In embodiments, the cancer tumor comprises an elevated level of a T cell gene signature relative to a control. In embodiments, the tumor infiltrating lymphocytes are CD8 T cells. The method includes administering to the subject a therapeutically effective amount of an adenosine-A2A receptor antagonist of formula:

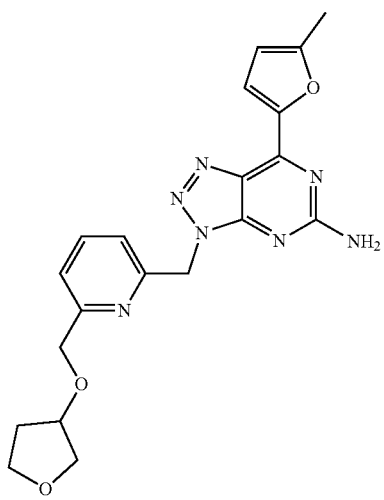

and a therapeutically effective amount of atezolizumab. In embodiments, the methods further comprise administering an anti-cancer agent.

In an aspect, a method of treating nivolumab refractory cancer in a subject in need thereof is provided. The method comprises administering to the subject a therapeutically effective amount of an adenosine-A2A receptor antagonist.

In an aspect, a method of treating cancer that is resistant to pembrolizumab, a tyrosine kinase inhibitor, or an mTOR inhibitor in a subject in need thereof is provided. The method comprises administering to the subject a therapeutically effective amount of an adenosine-A2A receptor antagonist.

BRIEF DESCRIPTION OF THE DRAWINGS

FIG. 1A is a waterfall plot showing that infiltration in the center of the tumor of >4% of tumor area is associated with increased tumor regression. The best change in SLD for each subject is shown in the waterfall plot colored by the percentage of CD8 infiltration in the center of the pre-treatment biopsy sample as measured by immunohistochemistry. Treatment with single agent CPI-444 or combination with atezolizumab and prior anti-PD-1 treatment status are indicated with colored rectangles under each subject on the waterfall plot. FIG. 1B is a waterfall plot of all dosed subjects with a measurable change in tumor growth, including subjects treated with CPI-444, subjects treated with CPI-444+atezolizumab, subjects with different tumor types, subjects resistant or refractory to anti-PD1 treatment, and subjects naïve for anti-PD1 treatment. A cutoff of 1% (rather than 4% for FIG. 1A) was used to classify subjects enriched for CD8 infiltration. The plot shows that infiltration in the center of the tumor of >1% of total cells is associated with tumor regression.

FIG. 2A: For the statistically significant genes in the Nanostring experiment the average of the normalized counts for CD8A=193, CXCL9=2254, CXCL10=1332, EOMES=22, IFNG=39, GZMB=330, CD274 (PD-L1)=123. The T-effector gene signature score is calculated as the geometric mean of the all the component genes listed in this figure.

FIGS. 3A and 3B show that baseline T clonality was associated with change in tumor size. Subjects with T cell receptor diversity (e.g., baseline T cell clonality within the normal healthy range (<0.2)) are enriched for tumor regression and changes in peripheral T cell receptor repertoire following CPI-444 treatment. Subjects with peripheral blood clonality within the normal healthy range (<0.2) showed tumor regression and changes in the peripheral TCR repertoire (indicated by Morisita Index<0.9). This shows drug induces T cell changes and efficacy in some subjects with normal/high baseline TCR diversity. FIG. 3C shows T clonality and change in tumor size for all subjects for which T clonality was assessed. Although the data for FIG. 3B did not reach statistical significe at the time of testing, the data suggests that subjects with baseline T cell clonality within the normal healthy range (<0.2) are more likely to have tumor regression following CPI-444 treatment.

In FIG. 9C, baseline biopsies revealed that subjects who were resistant to a prior PD-1 or PD-L1 treatment, with resistance defined as treatment greater than 3 months before discontinuation, exhibited higher CD73 gene expression than naïve subjects or subjects who were refractory as defined by treatment for less than 3 months.

FIG. 14 shows that expression of CD73 is associated with response to treatment. In embodiments, increased CD73 expression predicts subjects who are likely to benefit from treatment with CPI-444.

DETAILED DESCRIPTION

Definitions

Figure 1A:
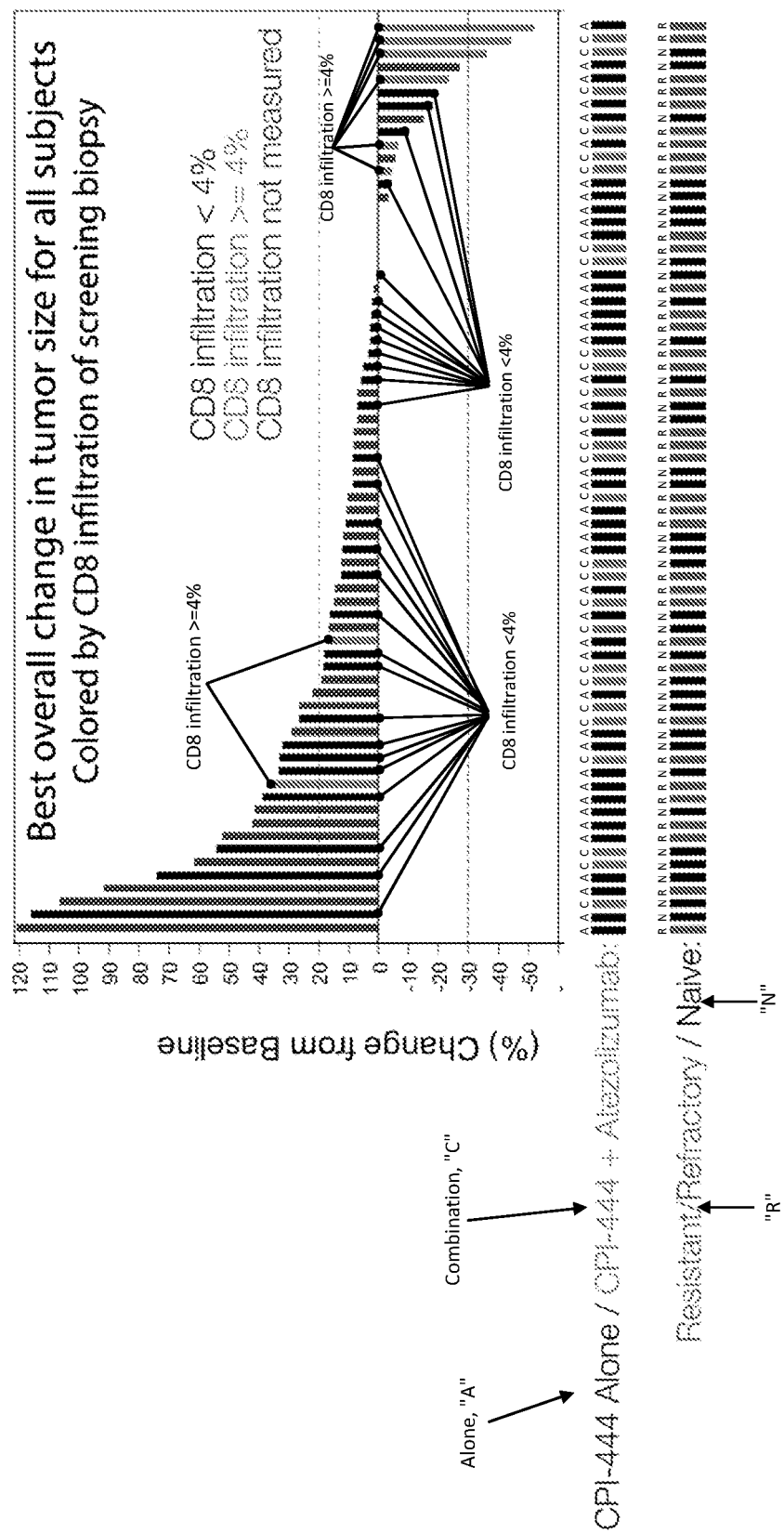
FIGS. 1A and 1B are waterfall plots showing that CD8 infiltration is associated with tumor regression. The waterfall plot includes all subjects from the clinical trial with available data, including all dosing levels and disease indications. CT scans of target lesions were performed prior to treatment and every 8 weeks post-treatment or at optimal time points. Target lesions were measured and the sum of longest dimensions (SLD) calculated. Subjects with regression of target tumor lesions are enriched for CD8 infiltration of tumors at baseline.
Figure 1B:
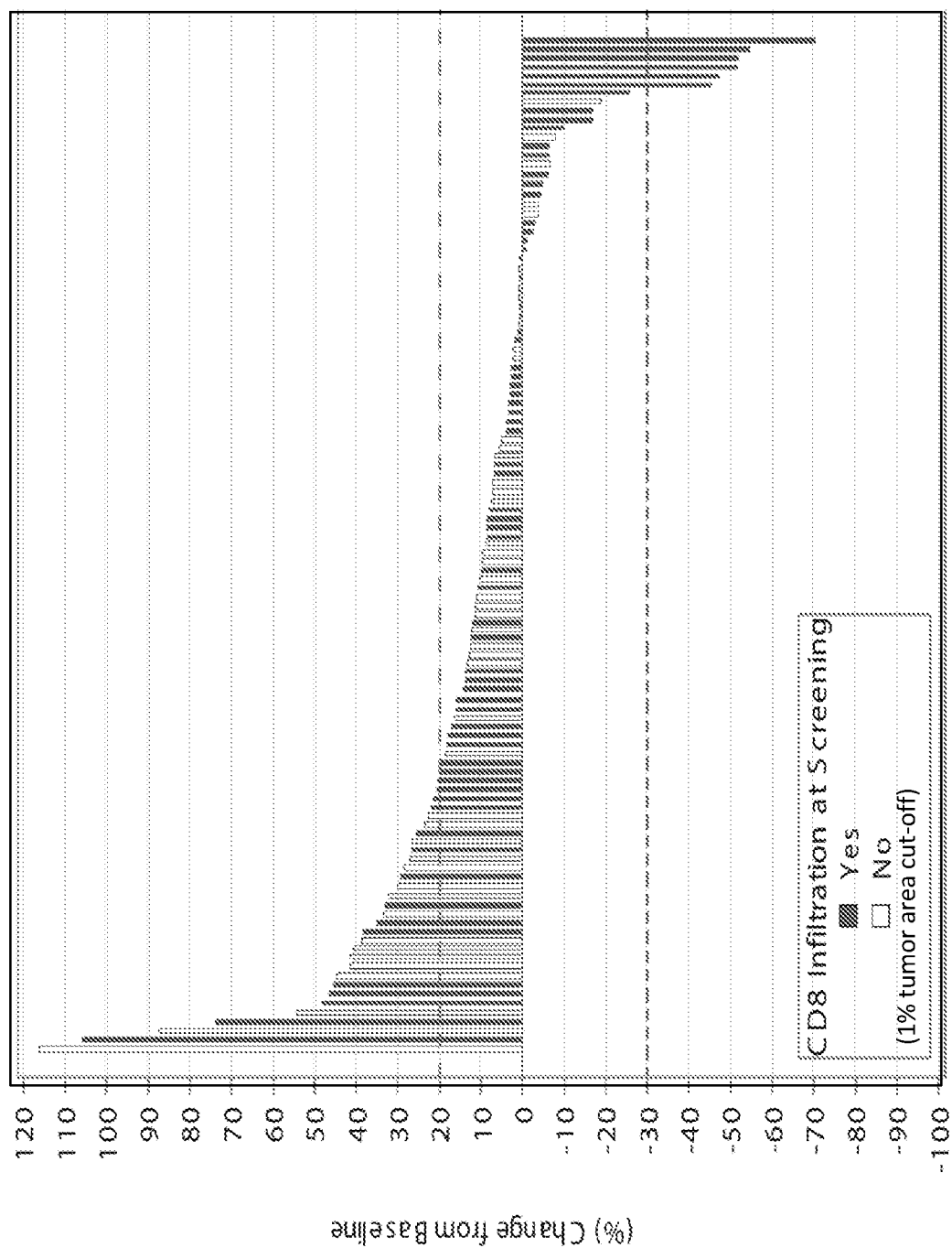
Figure 2A:
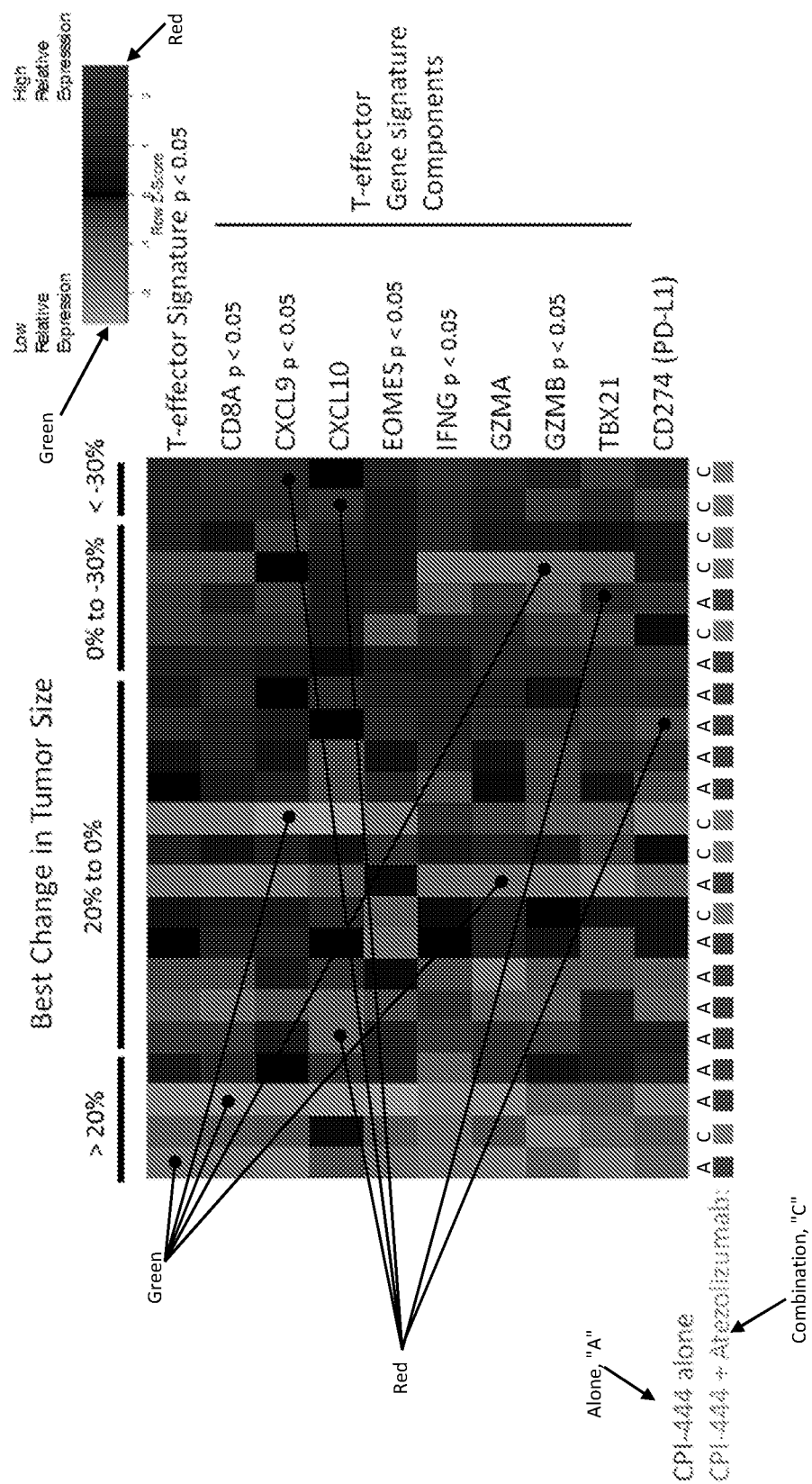
FIGS. 2A and B are gene expression heatmaps showing that T-effector signature genes and CD274 (PD-L1) are more highly expressed at baseline in tumors from subjects with tumor regression. Gene expression levels were determined from pre- and post-treatment tumor biopsies using the Nanostring Pan Cancer Immune Profiling panel with the addition of custom genes. Differential expression analysis was performed to determine gene expression differences between subjects in which a best change in tumor size showed no growth (less than or equal to zero) vs. those with tumor growth (greater than zero). A composite T-effector signature was calculated as the geometric mean of its composit genes; both the T-effector signature and a number of its component genes were expressed more highly in screen biopsy samples from subject with no tumor compared to subjects with tumor growth. For each gene shown, the z-score for each individual was calculated and used to display by color on the heatmap. When tumors are lined up from largest growth to smallest/regression, the tumors with little or no growth had high gene expression of the T-effector gene signature and some of the components thereof, and CD274. A z-score>0 is high expression. This means that a subject above the average gene expression of the entire cohort counts as high. Though gene expression was measured by Nanostring, but it could also be measured by other methods known in the art (e.g., RNAseq, qRT-PCR, or microarray analysis). A threshold cut-off for positive or high expression may be determined empirically.
Figure 2B:
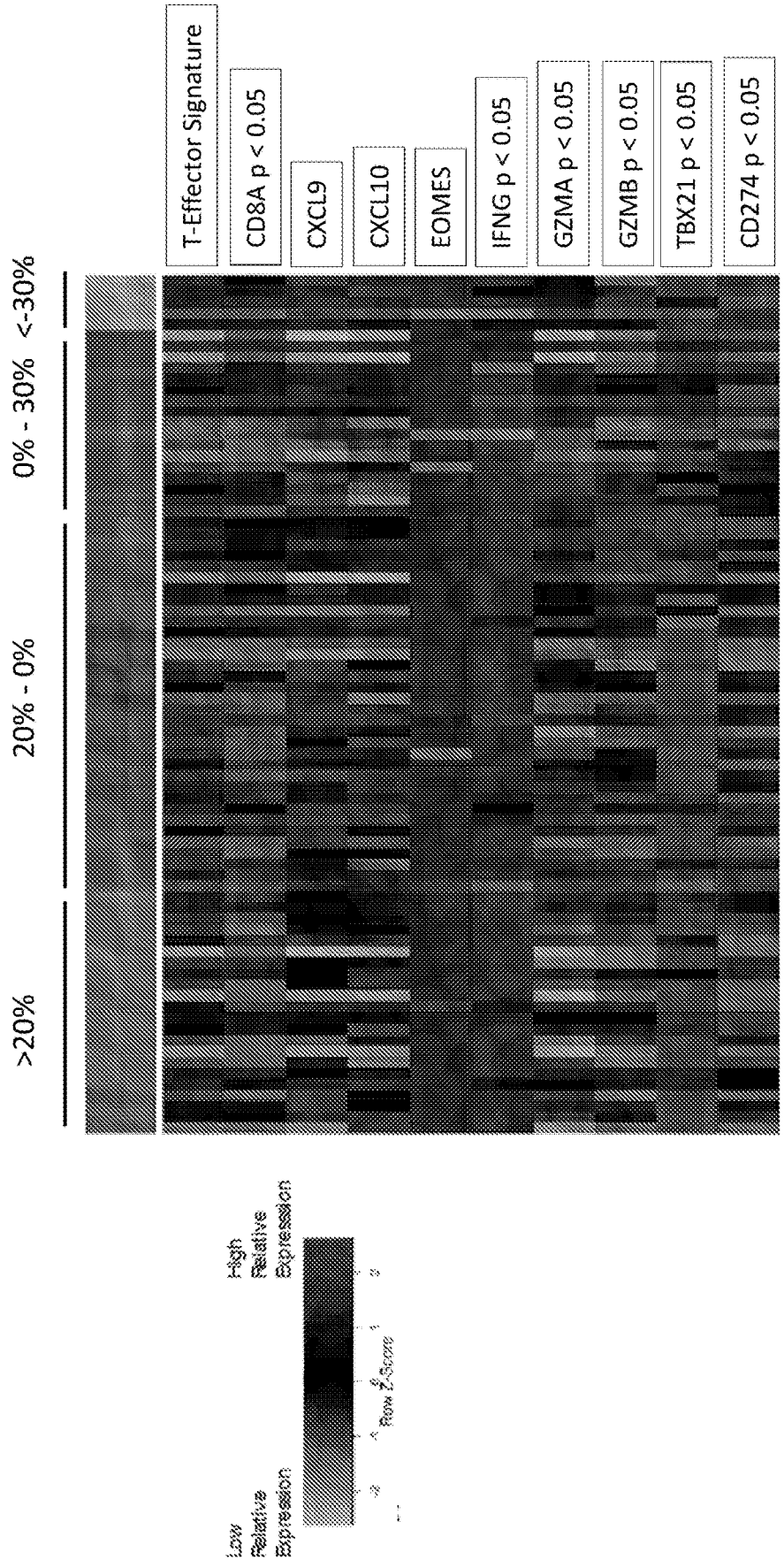
FIG. 2B shows a tumor shrinkage-sorted heatmap of key genes at time of screening. Expression of CD8A, IFNg, GZMA, GZMB, TBX21, and CD274 are significantly higher in baseline tumor samples of subjects that experienced tumor regression as determined by a best change in tumor size less than or equal to zero. The T-effector signature also is elevated in subjects that demonstrated tumor regression, but did not meet statistical significance (p=0.1).
Figure 3B:
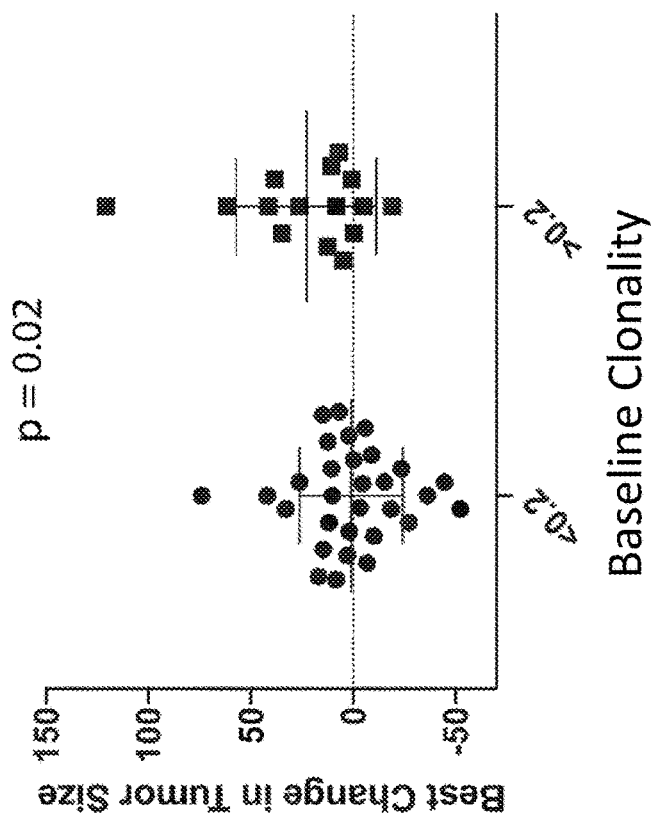
FIGS. 3A-3C: Peripheral blood mononuclear cells (PBMCs) were collected at day 0 and between day 28 and 56. Deep sequencing of TCRb and Moristia and clonality calculations were performed by Adaptive Biotechnologies (Seattle, Wash., USA). T cell receptor (TCR) repertoire clonality was assessed.
Figure 3A:
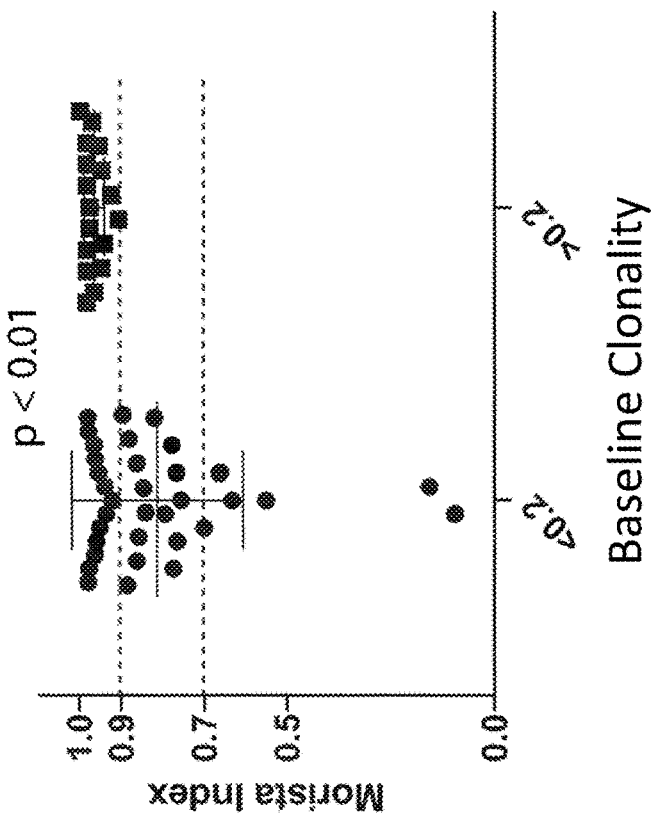
Figure 3C:
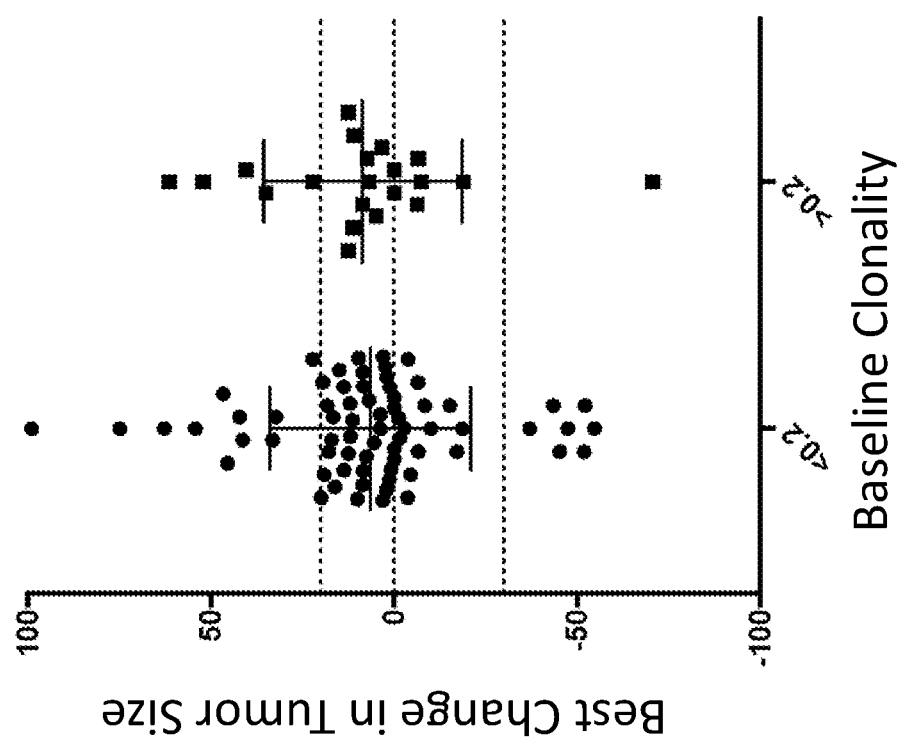
Figure 4:
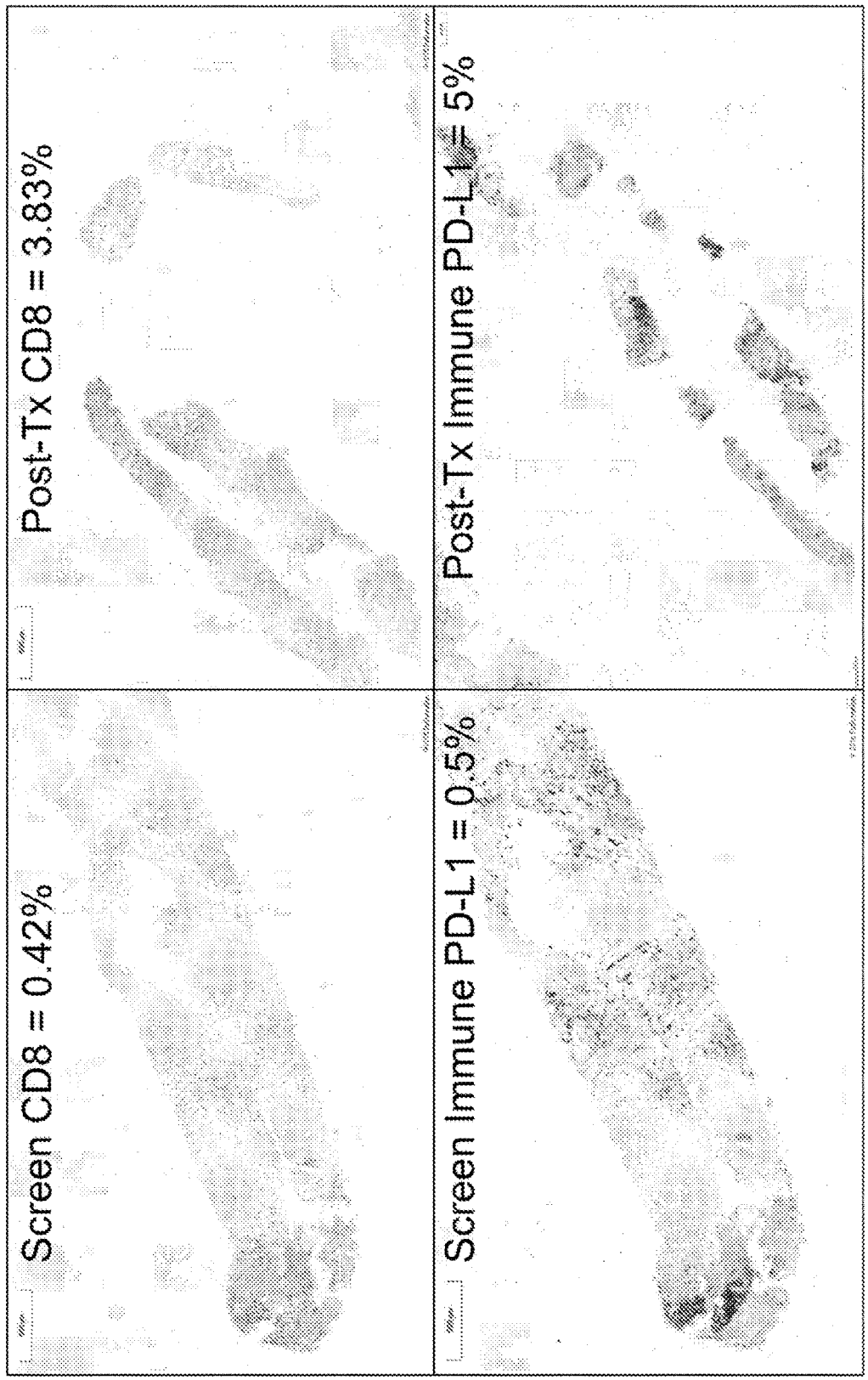
FIG. 4 shows images of example histology of PD-L1 and CD8 increase in post-Tx biopsy tumor (Non-Small Cell Lung Cancer). Core needle biopsies were collected prior to treatment and 1 to 4 months post-treatment. Biopsies were formalin fixed and parafin embedded. Four micron sections were cut for histology staining of CD8 (C8/144B), PD-L1 (SP142), and CD3 (2GV6) or for macrodissection and RNA extraction for gene expression analysis on a Nanostring machine. Scale bars=500 µm.
Figure 5:
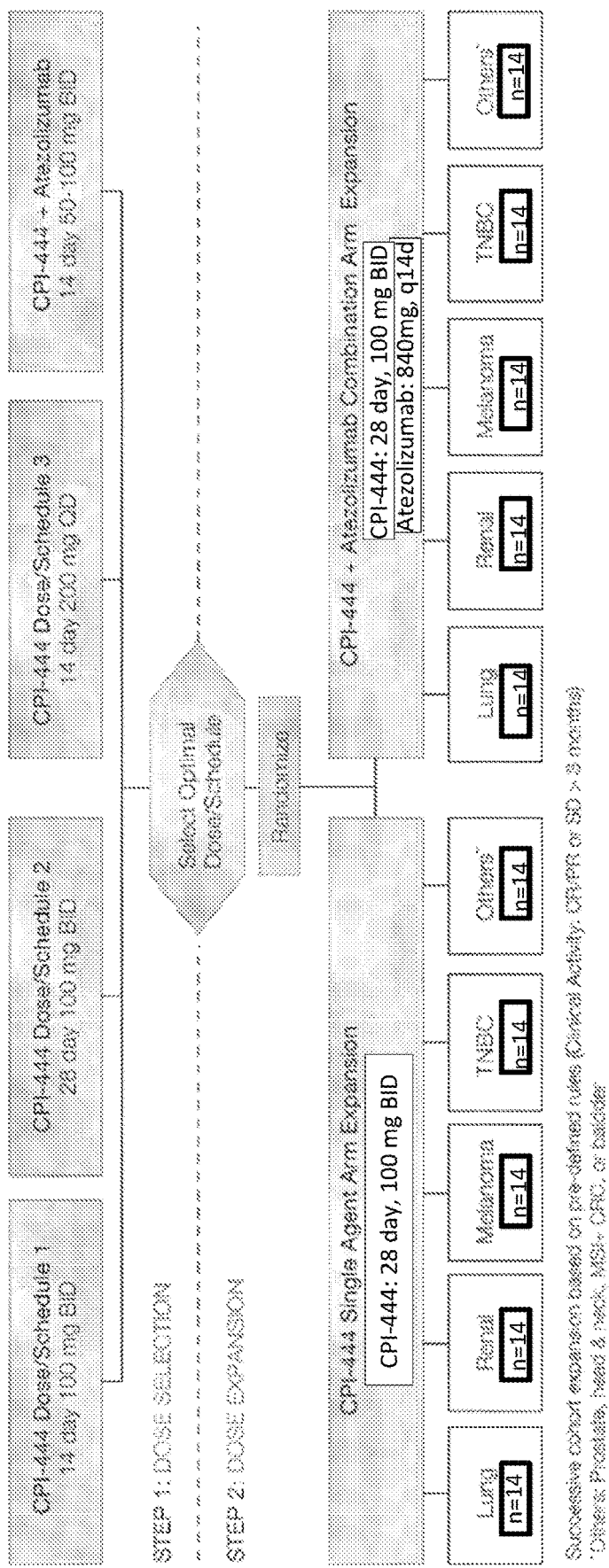
FIG. 5 is an illustration of an exemplary Phase 1/1B clinical trial design.
Figure 6:
FIG. 6 shows images showing anti-tumor immunity induced in responding renal cell carcinoma (RCC) PT., e.g. regression of tumors. The images in FIG. 6 and FIGS. 7A-7B show tumor regression in nivolumab refractory renal cancer treated with single agent CPI-444. There were five prior regimens including TKIs, mTOR inhibitor and nivolumab. The patient ultimately failed each prior therapy.
Figures 7A, 7B:
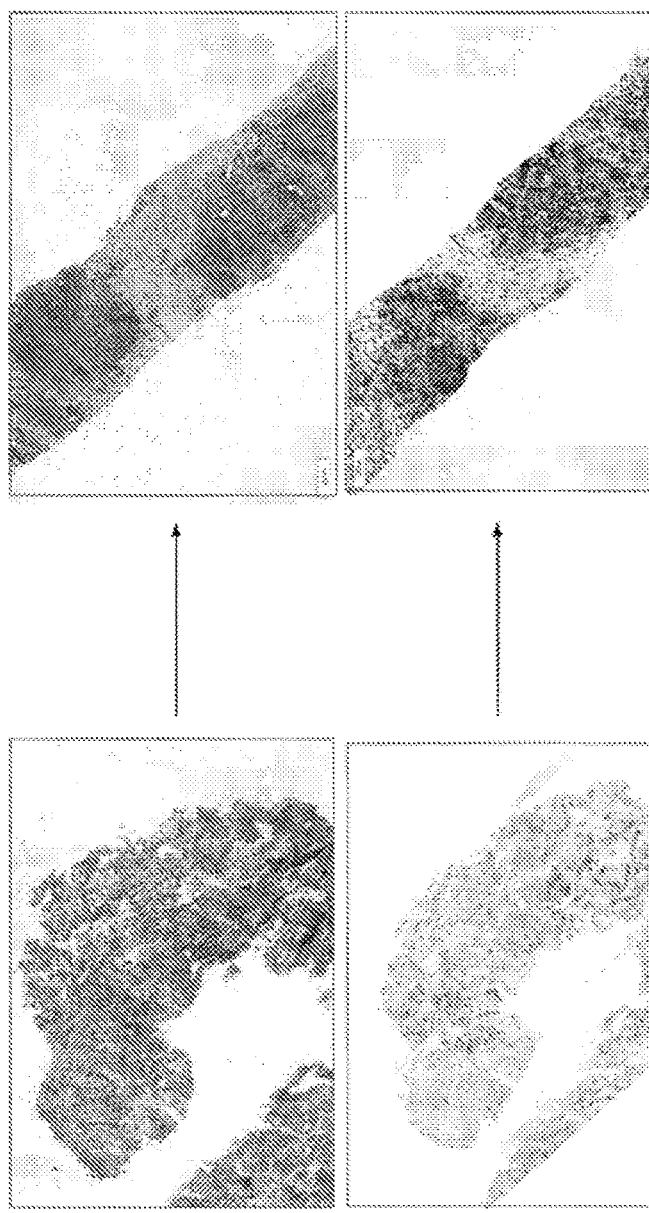
FIGS. 7A and 7B are images showing anti-tumor immunity induced in responding renal cell carcinoma (RCC) PT., e.g. increased immune infiltration (FIG. 7A) and increased CD8 tumor infiltrating lymphocyte infiltration (FIG. 7B). Scale Bars=500 µM.
Figure 8:
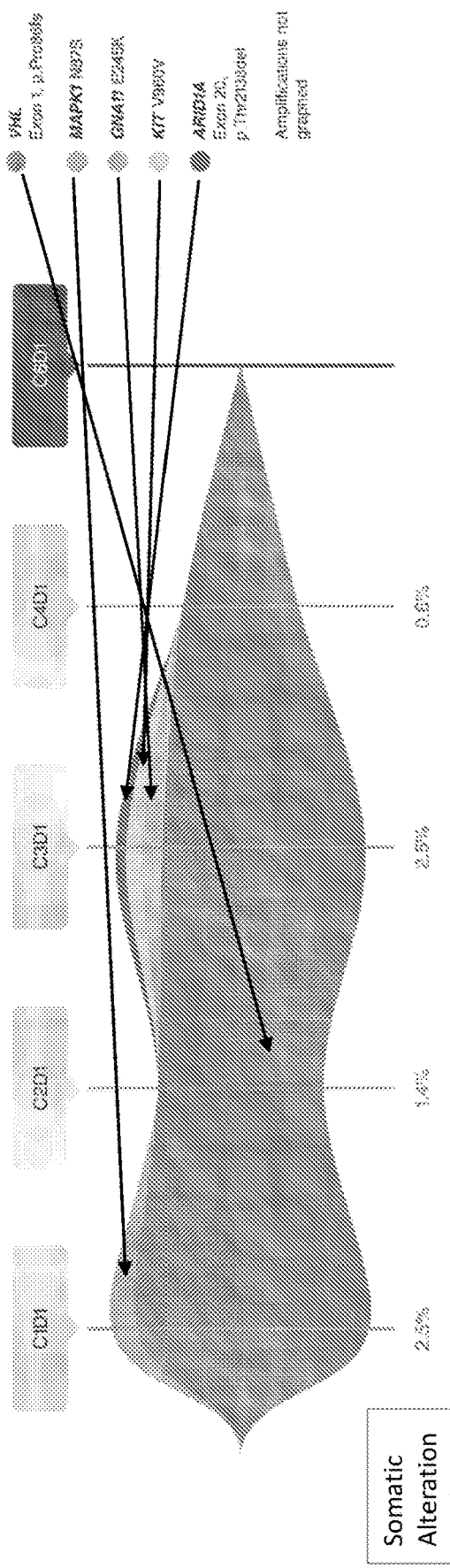
FIG. 8 is a diagram showing anti-tumor immunity induced in responding RCC PT., e.g. elimination of circulating tumor DNA
Figure 9B:
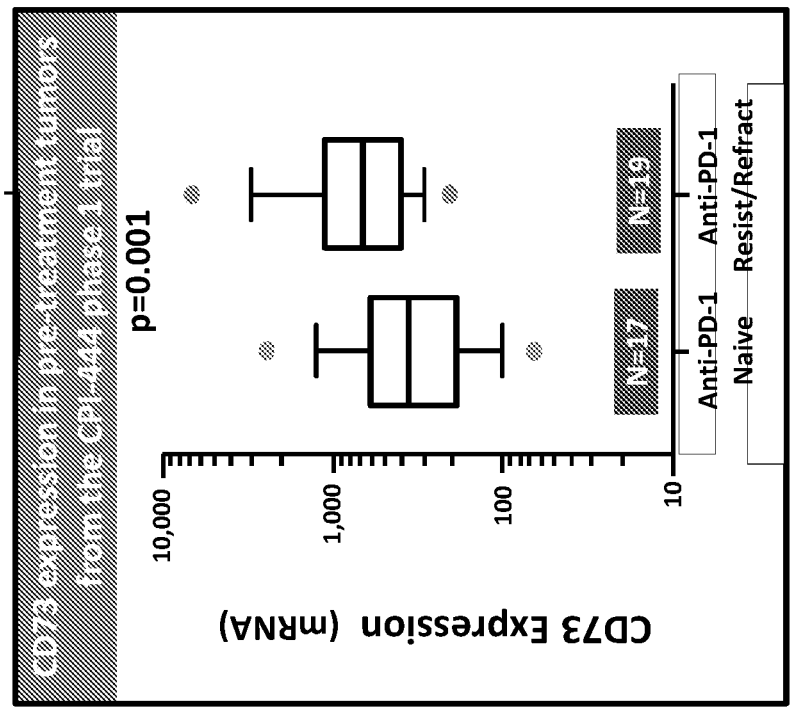
FIGS. 9A-9C are diagrams and graphs illustrating, without being bound by any theory, that adenosine suppresses immunity and can be a potential mechanism of resistance to PD-(L)1 therapy.
Figure 9A:
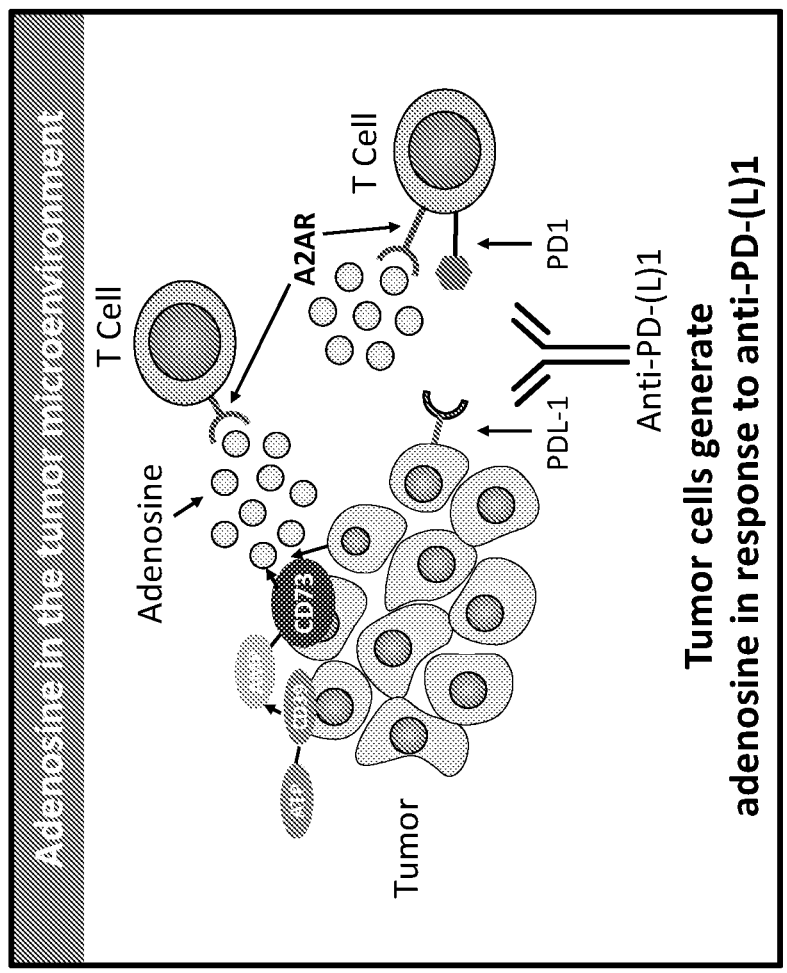
Figure 9C:
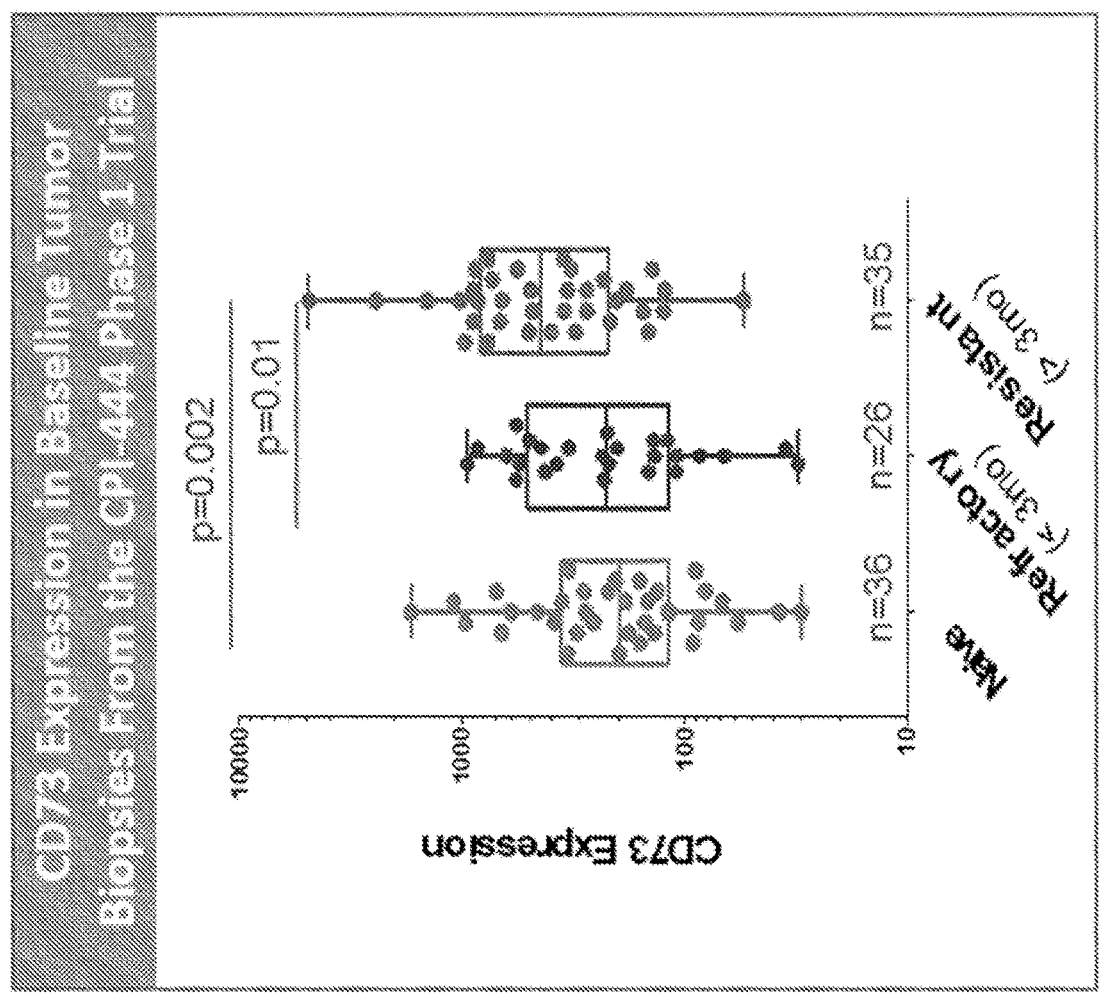
Figure 10:
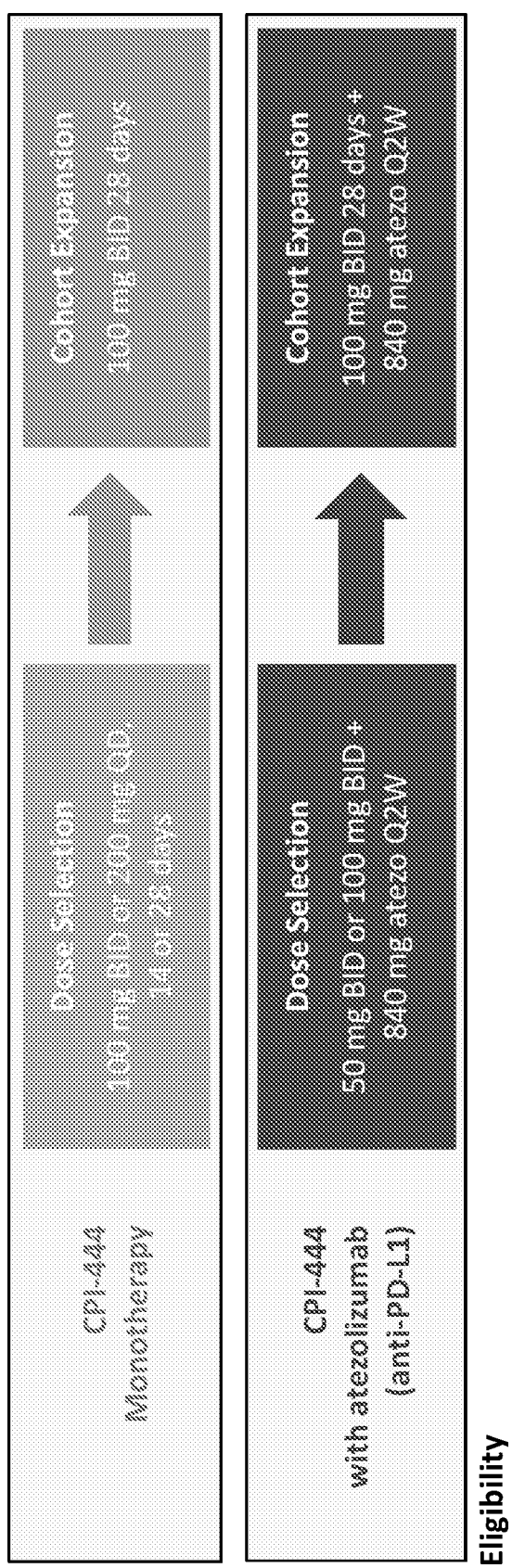
FIG. 10 shows non-limiting details relating to a Phase 1/1b clinical study with oral drug CPI-444. Expansion cohorts include renal cell and non-small cell lung cancer FIG. 11 provides a summary of exemplary patient characteristics. Archive samples data are available on 19 RCC and 28 NSCLC patients; based on FDA approved test, 5% cutoff FIG. 12 provides a summary of data regarding treatment-related adverse events. Arrows point to bars for combination treatment (CPI-444+atezolizumab).
Figures 13A, 13B, 13C:
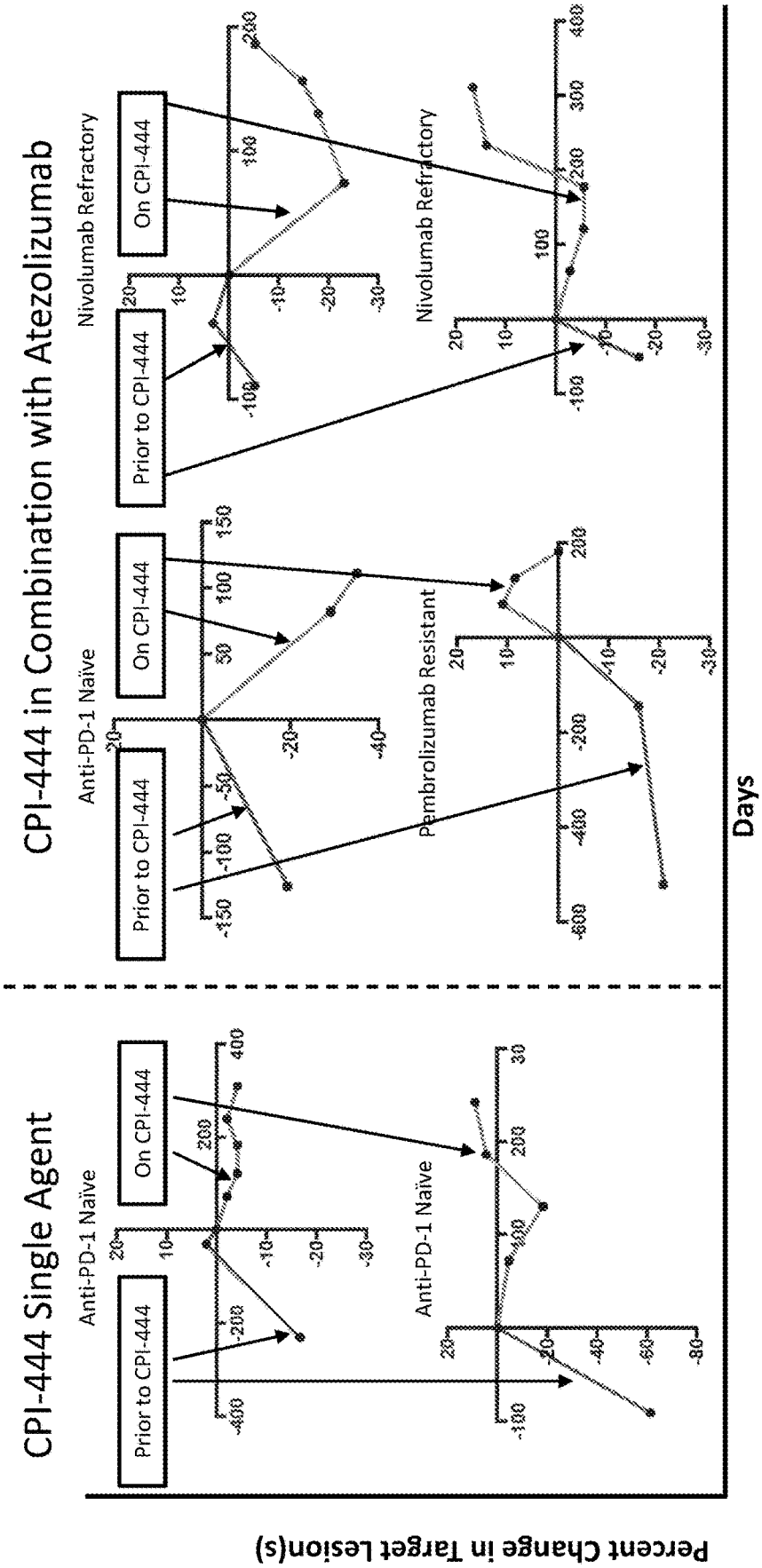
FIG. 13A-13C are graphs showing tumor growth kinetics in stable RCC patients.
Figure 14:
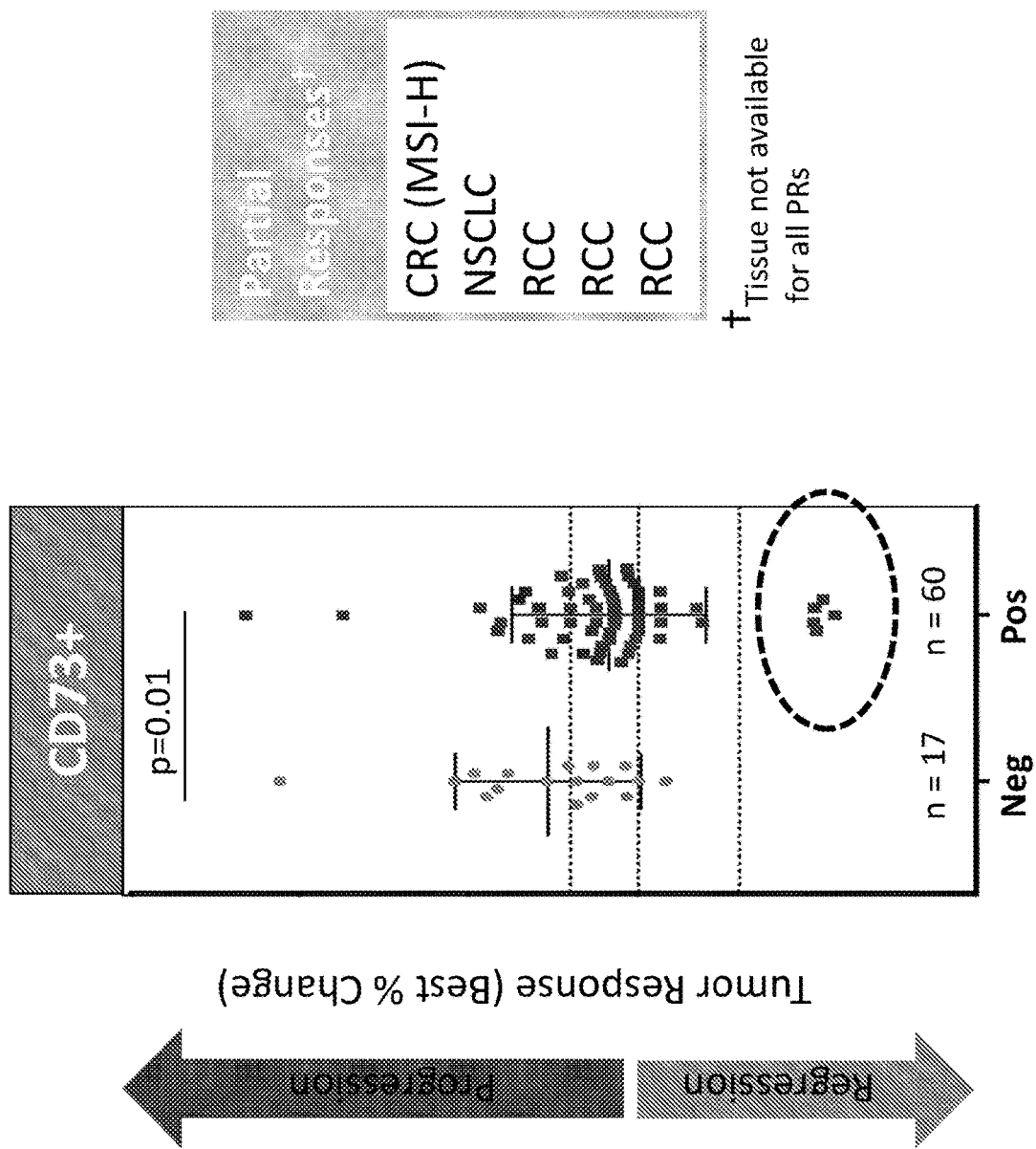
FIG. 14: Biopsies were collected from patients prior to beginning study drug, tumor was macrodissected and RNA extracted, and CD73 gene expression determine by Nanostring instrument.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., 0, N, or S). A heteroaryl moiety may include four optionally different ring heteroatoms (e.g., 0, N, or S). A heteroaryl moiety may include five optionally different ring heteroatoms (e.g., 0, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In embodiments, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties: (A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from: (i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from: (a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In embodiments, at least one or all of these groups are substituted with at least one size-limited substituent group. In embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable salts known to those of skill in the art are suitable. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol "⌇" and "-" denote the point of attachment of a chemical moiety to the remainder of a molecule or chemical formula.

In embodiments, a compound as described herein may include multiple instances of $R^2$ and/or other variables. In such embodiments, each variable may optional be different and be appropriately labeled to distinguish each group for greater clarity. For example, where each $R^2$ is different, they may be referred to, for example, as $R^{2.1}$, $R^{2.2}$, $R^{2.3}$, and/or $R^{2.4}$ respectively, wherein the definition of $R^2$ is assumed by $R^{2.1}$, $R^{2.2}$, $R^{2.3}$, and/or $R^{2.4}$. The variables used within a definition of $R^2$ and/or other variables that appear at multiple instances and are different may similarly be appropriately labeled to distinguish each group for greater clarity. In embodiments, the compound is a compound described herein (e.g., in an aspect, embodiment, example, claim, table, scheme, drawing, or figure).

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{12}$-substituted or unsubstituted alkyl, a plurality of $R^{12}$ substituents may be attached to the alkyl moiety wherein each $R^{12}$ substituent is optionally different. Where an R-substituted moiety is substituted with a plurality R substituents, each of the R-substituents may be differentiated herein using a prime symbol (') such as R', R", etc. For example, where a moiety is $R^{12}$-substituted or unsubstituted alkyl, and the moiety is substituted with a plurality of $R^{12}$ substituents, the plurality of $R^{12}$ substituents may be differentiated as $R^{12'}$, $R^{12''}$, $R^{12'''}$, etc. In embodiments, the plurality of R substituents is 3. In embodiments, the plurality of R substituents is 2.

In embodiments, a compound as described herein may include multiple instances of $R^1$, $R^2$, $R^3$, $R^4$, $R^5$, $R^6$, $R^7$, $R^9$, $R^{10}$, $R^{11}$, $R^{12}$, $R^{13}$, $R^{14}$ and/or other variables. In such embodiments, each variable may optional be different and be appropriately labeled to distinguish each group for greater clarity. For example, where each $R^1$, $R^2$, $R^3$, $R^4$, $R^5$, $R^6$, $R^7$, $R^9$, $R^{10}$, $R^{11}$, $R^{12}$, $R^{13}$, and/or $R^{14}$, is different, they may be referred to, for example, as $R^{1.1}$, $R^{1.2}$, $R^{1.3}$, $R^{1.4}$, $R^{2.1}$, $R^{2.2}$, $R^{2.3}$, $R^{2.4}$, $R^{3.1}$, $R^{3.2}$, $R^{3.3}$, $R^{3.4}$, $R^{4.1}$, $R^{4.2}$, $R^{4.3}$, $R^{4.4}$, $R^{5.1}$, $R^{5.2}$, $R^{5.3}$, $R^{5.4}$, $R^{6.1}$, $R^{6.2}$, $R^{6.3}$, $R^{6.4}$, $R^{7.1}$, $R^{7.2}$, $R^{7.3}$, $R^{7.4}$, $R^{9.1}$, $R^{9.2}$, $R^{9.3}$, $R^{9.4}$, $R^{10.1}$, $R^{10.2}$, $R^{10.3}$, $R^{10.4}$, $R^{11.1}$, $R^{11.2}$, $R^{11.3}$, $R^{11.4}$, $R^{12.1}$, $R^{12.2}$, $R^{12.3}$, $R^{12.4}$, $R^{13.1}$, $R^{13.2}$, $R^{13.3}$, $R^{13.4}$, $R^{14.1}$, $R^{14.2}$, $R^{14.3}$, and/or $R^{14.4}$, respectively, wherein the definition of $R^1$ is assumed by $R^{1.1}$, $R^{1.2}$, $R^{1.3}$, and/or $R^{1.4}$, the definition of $R^2$ is assumed by $R^{2.1}$, $R^{2.2}$, $R^{2.3}$, and/or $R^{2.4}$, the definition of $R^3$ is assumed by $R^{3.1}$, $R^{32}$, $R^{3.3}$, and/or $R^{3.4}$, the definition of $R^4$ is assumed by $R^{4.1}$, $R^{4.2}$, $R^{4.3}$, and/or $R^{4.4}$, the definition of $R^5$ is assumed by $R^{5.1}$, $R^{5.2}$, $R^{5.3}$, and/or $R^{5.4}$, the definition of $R^6$ is assumed by $R^{6.1}$, $R^{6.2}$, $R^{6.3}$, and/or $R^{6.4}$, the definition of $R^7$ is assumed by $R^{7.1}$, $R^{7.2}$, $R^{7.3}$, and/or $R^{7.4}$, the definition of $R^9$ is assumed by $R^{9.1}$, $R^{9.2}$, $R^{9.3}$, and/or $R^{9.4}$, the definition of $R^{10}$ is assumed by $R^{10.1}$, $R^{10.2}$, $R^{10.3}$, and/or $R^{10.4}$, the definition of $R^{11}$ is assumed by $R^{11.1}$, $R^{11.2}$, $R^{11.3}$, and/or $R^{11.4}$, the definition of $R^{12}$ is assumed by $R^{12.1}$, $R^{12.2}$, $R^{12.3}$, and/or $R^{12.4}$, the definition of $R^{13}$ is assumed by $R^{13.1}$, $R^{13.2}$, $R^{13.3}$, and/or $R^{13.4}$, the definition of $R^{14}$ is assumed by $R^{14.1}$, $R^{14.2}$, $R^{14.3}$, and/or $R^{14.4}$. The variables used within a definition of $R^1$, $R^2$, $R^3$, $R^4$, $R^5$, $R^6$, $R^7$, $R^9$, $R^{10}$, $R^{11}$, $R^{12}$, $R^{13}$ and/or $R^{14}$, and/or other variables that appear at multiple instances and are different may similarly be appropriately labeled to distinguish each group for greater clarity.

Descriptions of compounds herein are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

The term "antibody" is used according to its commonly known meaning in the art. As used herein, "antibody" may also refer to the antigen binding fragment thereof. Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor.

"Contacting" is used in accordance with its plain ordinary meaning and refers to the process of allowing at least two distinct species (e.g. chemical compounds including biomolecules or cells) to become sufficiently proximal to react, interact, or physically touch. It should be appreciated; however, the resulting reaction product can be produced directly from a reaction between the added reagents or from an intermediate from one or more of the added reagents which can be produced in the reaction mixture. In embodiments, contacting includes allowing two species to react, interact, or physically touch, wherein the two species may be, for example, a pharmaceutical composition as provided herein and a cell or a binding agent as described herein and its molecular target. In embodiments, contacting includes, for example, allowing a pharmaceutical composition as described herein to interact with a cell or a patient.

The terms "polypeptide," "peptide" and "protein" are used interchangeably herein to refer to a polymer of amino acid residues. In embodiments, the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: (1) Alanine, Glycine; (2) Aspartic acid, Glutamic acid; (3) Asparagine, Glutamine; (4) Arginine, Lysine; (5) Isoleucine, Leucine, Methionine, Valine; (6) Phenylalanine, Tyrosine, Tryptophan; (7) Serine, Threonine; and (8) Cysteine, Methionine. (see, e.g., Creighton, *Proteins* (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then the to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (NCBI; www.ncbi.nlm.nih.gov/). In embodiments, a BLAST algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value;

the cumulative score goes to zero or below, due to the accumulation of one or more negative-scoring residue alignments; or the end of either sequence is reached. The BLAST algorithm parameters W, T, and X determine the sensitivity and speed of the alignment. In embodiments, the NCBI BLASTN program (for nucleotide sequences) is used to determine identity. In embodiments, the NCBI BLASTP program (for amino acid sequences) is used to determine identity. In embodiments, the default BLASTN algorithm parameters for the NCBI BLASTN program are used. In embodiments, the BLASTN algorithm parameters include: automatic adjustment of parameters for short input sequences; an expect threshold of 10, a wordsize of 28; max matches in a query range of 0; match/mismatch scores of 1, −2; use of the filter for low complexity regions; and a mask for lookup table only. In embodiments, the default BLASTP algorithm parameters for the NCBI BLASTP program are used. In embodiments, the BLASTP algorithm parameters include: automatic adjustment of parameters for short input sequences; an expect threshold of 10; a wordsize of 6; max matches in a query range of 0; the BLOSUM62 matrix; gap costs of existence: 11 and extension: 1; and computational adjustments comprising conditional compositional score matrix adjustment.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated," when applied to a protein produced by a cell, denotes that the protein is essentially free of cellular components with which it is associated when produced (e.g., recombinantly or naturally) by the cell. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified," with respect to a protein, denotes that the protein gives rise to essentially one band in an electrophoretic gel. Particularly, it means that the protein is at least 85% pure, more preferably at least 95% pure, and most preferably at least 99% pure.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Typically a specific or selective reaction will be at least twice background signal or noise and more typically more than 10 to 100 times background.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells.

As defined herein, the term "inhibition", "inhibit", "inhibiting" and the like in reference to a protein-inhibitor (e.g., an A2A receptor antagonist or a PD-1 signaling pathway inhibitor) interaction means negatively affecting (e.g., decreasing) the activity or function of the protein (e.g., decreasing the activity of an A2A receptor or a PD-1 protein or PD-L1 protein) relative to the activity or function of the protein in the absence of the inhibitor (e.g., an A2A receptor antagonist or a PD-1 signaling pathway inhibitor). In embodiments, inhibition refers to reduction of a disease or symptoms of disease (e.g., cancer). Thus, inhibition includes, at least in part, partially or totally blocking stimulation, decreasing, preventing, or delaying activation, or inactivating, desensitizing, or down-regulating signal transduction or enzymatic activity or the amount of a protein (e.g., an A2A receptor or a PD-1 protein or PD-L1 protein). Similarly an "inhibitor" is a compound or protein that inhibits an A2A receptor or a PD-1 protein or PD-L1 protein, e.g., by binding, partially or totally blocking, decreasing, preventing, delaying, inactivating, desensitizing, or down-regulating activity (e.g., an A2A receptor activity or a PD-1 protein activity or PD-L1 protein activity).

An "anti-cancer agent" is a therapeutic used in the treatment or prevention of cancer. An anti-cancer agent can be a large or small molecule. Example anti-cancer agents include antibodies, small molecules, and large molecules or combinations thereof. In embodiments, an anti-cancer agent is not a PD-1 pathway inhibitor.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is not an anti-PD-1 pathway inhibitor. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+ estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus Calmette-Guerin* (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibodycalicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound. In embodiments, an analog is an adenosine analog. An example of an adenosine analog is 5'-N-ethyl-carboxamido-adenosine (NECA), having the structure shown below:

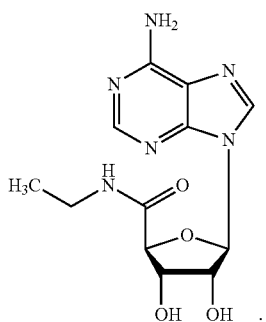

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

An "A2A receptor" or "adenosine-A2A receptor" or "adenosine A2A receptor" as referred to herein includes any of the recombinant or naturally-occurring forms of the adenosine A2A receptor also known as ADORA2A or isoforms or variants or homologs thereof that maintain adenosine A2A receptor activity (e.g. within at least 50%, 80%, 90%, 95%, 96%, 97%, 98%, 99% or 100% activity compared to adenosine A2A receptor). In some aspects, the isoforms, variants, or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring adenosine A2A receptor. In embodiments, the adenosine A2A receptor is substantially identical to the protein identified by the UniProt reference number P29274 or an isoform, variant, or homolog having substantial identity thereto. In embodiments, the adenosine A2A receptor is substantially identical to the protein identified by the UniProt reference number Q60613 or an isoform, variant or homolog having substantial identity thereto. In embodiments, ADORA2A is the protein as identified by the NCBI sequence reference GI:5921992, homolog or functional fragment thereof.

"A2B receptor" or "A2BR" or "Adenosine $A_{2B}$ receptor" are used interchangeably. A2B receptors are expressed in some mast cells, such as the BR line of canine mastocytoma cells, which appear to be responsible for triggering acute $Ca^2$ mobilization and degranulation. (See Auchampach et al., Mol. Pharmacol. 1997, 52, 846-S60 and Forsyth et al., Inflamm. Res. 1999, 48, 301-307.) Adenosine $A_{2B}$ receptors also trigger $Ca^{2+}$ mobilization, and participate in a delayed 1L8 release from human HMC-1 mast cells. Other functions associated with the $A2_B$ AR are the control of cell growth and gene expression, (See Neary et al., Trends Neurosci. 1996, 19, 13-18.) endothelial-dependent vasodilation (See Martin et al., J Pharmacol. Exp. Ther. 1993, 265, 248-2,53.), and fluid secretion from intestinal epithelia. (See Strohmeier, et al., J Biol. Chem. 1995, 270, 2387-2394.) Adenosine acting through $A_2B$ receptor subtype has also been reported to stimulate chloride permeability in cells expressing the cystic fibrosis transport regulator. (See Clancy et al., Am. J Physiol. 1999, 276, C361-C369.) Example A2 receptor antagonists are described in WO 2008002902, included herein by reference in its entirety. In embodiments, the adenosine $A_{2B}$ receptor is substantially identical to the protein identified by the UniProt reference number P29275 or an isoform, variant, or homolog having substantial identity thereto.

"Adenosine receptor antagonist" references to a molecule that inhibits (i.e. reduces) activity of adenosine receptors (e.g. A2a or A2b receptors) relative to the absence of the adenosine receptor antagonist. Adenosine receptors antagonists can be small or large molecule antagonists. In embodiments, CPI-444 is an exemplary adenosine-A2A receptor antagonist.

A "PD-1 protein" or "PD-1" as referred to herein includes any of the recombinant or naturally-occurring forms of the Programmed cell death protein 1 (PD-1) also known as cluster of differentiation 279 (CD 279) or isoforms or variants or homologs thereof that maintain PD-1 protein activity (e.g. within at least 50%, 80%, 90%, 95%, 96%, 97%, 98%, 99% or 100% activity compared to PD-1 protein). In some aspects, the isoforms, variants, or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 protein. In embodiments, the PD-1 protein is substantially identical to the protein identified by the UniProt reference number Q15116 or an isoform, variant, or homolog having substantial identity thereto. In embodiments, the PD-1 protein is substantially identical to the protein identified by the UniProt reference number Q02242 or an isoform, variant, or homolog having substantial identity thereto. In embodiments, the PD-1 protein is substantially identical to NCBI Accession No. NP 005009.2. In embodiments, the PD-1 mRNA is substantially identical to NCBI Accession No. NM_00518.2.

A "PD-L1 protein" or "PD-L1" as referred to herein includes any of the recombinant or naturally-occurring forms of the programmed death-ligand 1 (PD-L1) also known as cluster of differentiation 274 (CD 274) or variants or homologs thereof that maintain PD-L1 protein activity (e.g. within at least 50%, 80%, 90%, 95%, 96%, 97%, 98%, 99% or 100% activity compared to PD-L1 protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-L1 protein. In embodiments, the PD-L1 protein is substantially identical to the protein identified by the UniProt reference number Q9NZQ7 or a variant or homolog having substantial identity thereto. In embodiments, the PD-L1 protein is substantially identical to the protein identified by the UniProt reference number Q9EP73 or a variant or homolog having substantial identity thereto.

The term "atezolizumab" or "MPDL3280A" refers to a fully humanized, engineered monoclonal antibody of IgG1 isotype against the protein programmed cell death ligand 1 (PD-L1). Atezolizumab refers to CAS Registry number 1380723-44-3. Atezolizumab may be referred to as an anti-cancer agent. In embodiments, atezolizumab is referred to with the tradename TECENTRIQ®. An "atezolizumab refractory subject" refers to a subject who is an PD-1 pathway refractory subject and the prior anti-PD-1 pathway treatment was with atezolizumab. An "atezolizumab resistant subject" refers to a subject who is an PD-1 pathway resistant subject and the prior PD-1 pathway treatment was with atezolizumab. An "atezolizumab refractory cancer" refers to a cancer that is refractory to treatment with atezolizumab. An "atezolizumab resistant cancer" refers to a cancer that is resistant to treatment with atezolizumab.

"Nivolumab" refers to a human IgG4 anti-PD-1 monoclonal antibody that is commercially available as OPDIVO® by Bristol-Myers Squibb. Nivolumab refers to CAS Registry number 946414-94-4. Nivolumab may be referred to as an anti-cancer agent. A "nivolumab refractory subject" refers to a subject who is an PD-1 pathway refractory subject and the prior anti-PD-1 pathway treatment was with nivolumab. A "nivolumab resistant subject" refers to a subject who is a PD-1 pathway resistant subject and the prior anti-PD-1 pathway treatment was with nivolumab. A "nivolumab refractory cancer" refers to a cancer that is refractory to treatment with nivolumab. A "nivolumab resistant cancer" refers to a cancer that is resistant to treatment with nivolumab.

The term "blood cell detection agent" refers to a chemical or molecular moiety capable of identifying blood cells. A blood cell detection agent can refer to, for example, a chemical stain or an antibody against cell surface markers. Example blood cell detection agents include B cell detection agents and T cell detection agents.

The term "B cell detection agent" refers to a chemical or molecular moiety capable of identifying B cells. In examples, a B cell detection agent can be an antibody to a B cell specific surface maker (e.g. an antibody against CD19, or an antibody against CD20). B cell detection agents can be used alone or in combination. B cell detection agents can further be detected by fluorescence activated cell sorting (FACS).

"B Cells" or "B lymphocytes" refer to their standard use in the art. B cells are lymphocytes, a type of white blood cell (leukocyte), that develops into a plasma cell (a "mature B cell"), which produces antibodies. An "immature B cell" is a cell that can develop into a mature B cell. Generally, pro-B cells undergo immunoglobulin heavy chain rearrangement to become pro B pre B cells, and further undergo immunoglobulin light chain rearrangement to become an immature B cells. Immature B cells include T1 and T2 B cells.

"T cell detection agents" refers to a chemical or molecular moiety capable of identifying T cells. In examples, a T cell detection agent can be an antibody to a T cell specific surface maker (e.g. an antibody against CD3, and antibody against C4, or an antibody against CD8). T cell detection agents can be used alone or in combination. T cell detection agents can further be detected by fluorescence activated cell sorting (FACS).

"T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

The term "cell subset detection agent" refers to a chemical or molecule detection agent that can be used to identify and distinguish a specific subset of cells (e.g. senescent cells, naïve cells, effector cells, memory cells etc). Example cell subset detection agents include "naïve cell detection agents", "memory cell detection agents", and "effector cell detection agent." Cell subset detection agents can include antibodies against distinguishing cell surface markers. In embodiments, cell subset detection agents include antibodies against CD27 or antibodies against CD45RA.

The term "apoptotic cells detection agent" refers to a chemical or molecule detection agent that can be used to identify and distinguish apoptotic cells. Apoptotic cell detection agents can include antibodies against distinguishing cell surface markers. An example apoptosis detection agent includes an antibody against cPARP. PARP is inactivated by caspase cleavage. Cleaved poly-ADP-ribose polymerase (PARP) (cPARP) is the cleavage product of PARP. cPARP can be used as a marker for apoptosis.

The term "CD" or "Cluster of Differentiation" refers to a nomenclature system for antigens found on lymphocytes, although CD antigens can be found on cells other than lymphocytes. This nomenclature is used to name antigens recognized by monoclonal antibodies that specifically bind an antigen on B cells, T cells or antigen presenting cells. Each numeric antigen is a specific protein that is recognized in the art by its CD designation.

The term "CD3" as referred to herein is a protein complex comprising four chains including a CD3γ chain, a CD3δ chain, and two CD3ε chains. Non-limiting sequences of CD3 complex chains include: Epsilon chain precursor (NCBI Accession No. NP_000724.1); Gamma chain precursor (NCBI Accession No. NP_000064.1); Delta chain precursor (NCBI Accession No. NP_000723.1) which are incorporated herein by reference. Multiple isoforms are possible for each of the chains of CD3.

The term "CD4" as referred to herein is a glycoprotein expressed on the surface of T helper cells, regulatory T cells, monocytes, macrophages, and dendritic cells. CD4 was originally known as leu-3 and T4 (after the OKT4 monoclonal antibody). CD4 as referred to herein has four immunoglobulin domains ($D_1$ to $D_4$) that are exposed on the extracellular surface of the cell, see ENTREZ No. 920, UNIPROT No. P01730, and NCBI Accession No. NP_000607.1, which are incorporated by reference.

A "CD4+ T lymphocyte" or "CD4 T cell" and the like as referred to herein is a lymphocyte that expresses the CD4 glycoprotein on its surface. CD4 T cells include helper T cells, which are T cells that help orchestrate the immune response, including antibody responses and killer T cell responses. CD4 T cell precursors differentiate into one of several subtypes, including TH1 (type 1 helper T cell), TH2 (type 2 helper T cell), TH3 (T helper 3 cells), TH17 (T helper 17 cells) or TFH (Follicular B helper T cells). These subtypes of helper T cells are characterized by their secretion of different cytokines to facilitate different types of immune responses. In embodiments, a CD4 T cell is an effector T cell.

An "effector T cell" as referred to herein is a T cell that has been activated by its cognate antigen, and is actively involved in eliminating a pathogen or tumor cell. Thus, an effector T cell actively responds to a stimulus (a pathogen, tumor antigen, or a co-stimulation) and carries out a cell-mediated immune response. Non-limiting examples of effector T cells as referred to herein include helper T cells, killer T cells (cytotoxic T cells) and regulatory T cells.

A "CD8+ T lymphocyte" or "CD8 T cell" and the like as referred to herein is a lymphocyte that expresses the CD8 glycoprotein on its surface. Examples of CD8 T cells include cytotoxic T cells and natural killer cells. In one embodiment, a CD8 T cell is a cytotoxic T cell. In embodiments, a CD8 T cell is a suppressor T cell.

CD20 is involved in regulating early steps in the activation and differentiation process of B cells (Tedder et al., *Eur. J. Immunol.* 16:881-887, 1986) and can function as a calcium ion channel (Tedder et al., *J. Cell. Biochem.* 14D: 195, 1990). Non-limiting examples of amino acid sequences for CD19 are provided in NCBI Accession Nos. NP_068769.2 (human), NP_690605.1 (human), and NP_031667.1 (mouse), which are incorporated by reference herein.

CD27: A costimulatory immune checkpoint molecule. CD27 precursor (human)(NCBI Accession No. NP_001233.1). Multiple isoforms exist.

The term "CD45RA" as provided herein refers to the CD45 Receptor antigen also known as Protein tyrosine phosphatase, receptor type, C (PTPRC). Non-limiting amino acid sequences for CD45RA include NCBI Accession Nos. NP_002829.3, NP_563578.2, NP_563578.2, and NP_002829.3, which are all incorporated herein by reference. CD45RA is expressed on naïve T cells, as well as on CD8- and CD4-expressing effector cells. After antigen interaction, T cells gain expression of CD45RO and lose expression of CD45RA. Thus, either CD45RA or CD45RO is used to generally differentiate the naïve from memory T cell populations. Thus, a "CD45RA-negative CD8 T cell" as provided herein is a CD8 T cell which lacks expression of detectable amounts of CD45RA. In embodiments, the CD45RA-negative CD8 T cell is a memory T cell. A "CD45RA-negative CD4 T cell" as provided herein is a CD4 T cell which lacks expression of detectable amounts of CD45RA. In embodiments, the CD45RA-negative CD4 T cell is a memory T cell. In embodiments, the CD45RA-negative CD8 T cell is a memory T cell.

The term "CD8" as referred to herein is a transmembrane glycoprotein that serves as a co-receptor for the T cell receptor (TCR). Like the TCR, CD8 binds to a major histocompatibility complex (MHC) molecule, but is specific for the class I MHC protein, see, e.g., ENTREZ No. 925 and UNIPROT No. P01732, which are incorporated by reference herein.

The most common form of CD8 comprises an alpha-chain and a beta-chain. The term "CD8a" as provided herein refers to the alpha-chain of CD8, and includes homologues and isoforms thereof. Non-limiting amino acid sequences for CD8a include NCBI Accession Nos. AAH25715.1, NP_001759.3, and NP_741969.1, which are all incorporated herein by reference. Non-limiting nucleotide sequences for CD8a include NCBI Accession Nos. NR_027353.1, NM_001768.6, NM_171827.3, and NM_001145873.1, which are all incorporated herein by reference. In embodiments, a CD8a protein is a protein having amino acids in the sequence of one of the NCBI Accession numbers for CD8a disclosed herein, or an isoform or homologue thereof. In embodiments, a CD8a protein includes any protein having amino acids in the sequence of any one of one of the NCBI Accession numbers for CD8a disclosed herein, or an isoform or homologue thereof.

The term "PD-L1" as provided herein refers to programmed death-ligand 1 also known as CD274, and includes homologues and isoforms thereof. Non-limiting examples of amino acid sequences for PD-L1 include NCBI Accession Nos. AAI13735.1, AAI13737.1, and AAH74984.1, which are all incorporated herein by reference. Non-limiting examples of nucleotide sequences for PD-L1 include NCBI Accession Nos. NM_014143.3, NM_001267706.1, NR_052005.1, and NM_001314029.1, which are all incorporated herein by reference. In embodiments, a PD-L1 protein is a protein having amino acids in the sequence of one of the NCBI Accession numbers for PD-L1 disclosed herein, or an isoform or homologue thereof. In embodiments, a PD-L1 protein includes any protein having amino acids in the sequence of any one of one of the NCBI Accession numbers for PD-L1 disclosed herein, or an isoform or homologue thereof.

The term "CXCL9" as provided herein refers to C-X-C motif chemokine ligand 9, and includes homologues and isoforms thereof. Non-limiting examples of amino acid sequences for CXCL9 include NCBI Accession Nos. NP_002407.1, EAX05763.1, and AAH63122.1, which are all incorporated herein by reference. Non-limiting examples of nucleotide sequences for CXCL9 include NCBI Accession Nos. NM_002416.2, BC095396.1, and BC063122.1, which are all incorporated herein by reference. In embodiments, a CXCL9 protein is a protein having amino acids in the sequence of one of the NCBI Accession numbers for CXCL9 disclosed herein, or an isoform or homologue thereof. In embodiments, a CXCL9 protein includes any protein having amino acids in the sequence of any one of one of the NCBI Accession numbers for CXCL9 disclosed herein, or an isoform or homologue thereof.

The term "CXCL10" as provided herein refers to C-X-C motif chemokine ligand 10, and includes homologues and isoforms thereof. Non-limiting examples of amino acid sequences for CXCL10 include NCBI Accession Nos. NP_001556.2, EAX05773.1, AAH10954.1, and EAX05772.1, which are all incorporated herein by reference. Non-limiting examples of nucleotide sequences for CXCL10 include NCBI Accession Nos. NM_001565.3 and BC010954.1, which are all incorporated herein by reference. In embodiments, a CXCL10 protein is a protein having amino acids in the sequence of one of the NCBI Accession numbers for CXCL10 disclosed herein, or an isoform or homologue thereof. In embodiments, a CXCL10 protein includes any protein having amino acids in the sequence of any one of one of the NCBI Accession numbers for CXCL10 disclosed herein, or an isoform or homologue thereof.

The term "EOMES" as provided herein refers to eomesodermin, and includes homologues and isoforms thereof. Non-limiting examples of amino acid sequences for EOMES include NCBI Accession Nos. NP 001265112.1, NP 005433.2, and NP_001265111.1, which are all incorporated herein by reference. Non-limiting examples of nucleotide sequences for EOMES include NCBI Accession Nos. NM_001278183.1, NM_005442.3, and NM_001278182.1, which are all incorporated herein by reference. In embodiments, a EOMES protein is a protein having amino acids in the sequence of one of the NCBI Accession numbers for EOMES disclosed herein, or an isoform or homologue thereof. In embodiments, a EOMES protein includes any protein having amino acids in the sequence of any one of one of the NCBI Accession numbers for EOMES disclosed herein, or an isoform or homologue thereof.

The term "IFNγ" as provided herein refers to interferon gamma, and includes homologues and isoforms thereof. Non-limiting examples of amino acid sequences for IFNγ include NCBI Accession Nos. AAB59534.1, NP 000610.2, AAM28885.1, and AAA53230.1, which are all incorporated herein by reference. Non-limiting examples of nucleotide sequences for IFNγ include NCBI Accession Nos. NM_000619.2, AF506749.1, and AY255837.1, which are all incorporated herein by reference. In embodiments, a IFNγ protein is a protein having amino acids in the sequence of one of the NCBI Accession numbers for IFNγ disclosed herein, or an isoform or homologue thereof. In embodiments, a IFNγ protein includes any protein having amino acids in the sequence of any one of one of the NCBI Accession numbers for IFNγ disclosed herein, or an isoform or homologue thereof.

The term "GZMA" as provided herein refers to granzyme A, and includes homologues and isoforms thereof. Non-limiting examples of amino acid sequences for GZMA include NCBI Accession Nos. CAG33249.1 and NP 006135.1, which are all incorporated herein by reference. An non-limiting example of a nucleotide sequence for GZMA includes NCBI Accession Nos. NM_006144.3, which is incorporated herein by reference. In embodiments, a GZMA protein is a protein having amino acids in the sequence of one of the NCBI Accession numbers for GZMA disclosed herein, or an isoform or homologue thereof. In embodiments, a GZMA protein includes any protein having amino acids in the sequence of any one of one of the NCBI Accession numbers for GZMA disclosed herein, or an isoform or homologue thereof.

The term "GZMB" as provided herein refers to granzyme B, and includes homologues and isoforms thereof. Non-limiting examples of amino acid sequences for GZMB include NCBI Accession Nos. NP 001332940.1, NP_004122.2, EAW66003.1, and EAW66002.1, which are all incorporated herein by reference. Non-limiting examples of nucleotide sequences for GZMB include NCBI Accession Nos. NM_004131.5 and NM_001346011.1, which are all incorporated herein by reference. In embodiments, a GZMB protein is a protein having amino acids in the sequence of one of the NCBI Accession numbers for GZMB disclosed herein, or an isoform or homologue thereof. In embodiments, a GZMB protein includes any protein having amino acids in the sequence of any one of one of the NCBI Accession numbers for GZMB disclosed herein, or an isoform or homologue thereof.

The term "TBX21" as provided herein refers to T-box 21, commonly known as Tbet, and includes homologues and isoforms thereof. Non-limiting examples of amino acid sequences for TBX21 include NCBI Accession Nos. NP_037483.1, EAW94804.1, and AAH39739.1, which are all incorporated herein by reference. Non-limiting examples of nucleotide sequences for TBX21 include NCBI Accession Nos. NM_013351.1 and XM_011524698.2, which are all incorporated herein by reference. In embodiments, a TBX21 protein is a protein having amino acids in the sequence of one of the NCBI Accession numbers for TBX21 disclosed herein, or an isoform or homologue thereof. In embodiments, a TBX21 protein includes any protein having amino acids in the sequence of any one of one of the NCBI Accession numbers for TBX21 disclosed herein, or an isoform or homologue thereof.

The term "CXCL16" as provided herein refers to chemokine (C-X-C motif) ligand 16, and includes homologues and isoforms thereof. Non-limiting examples of amino acid sequences for CXCL16 include NCBI Accession Nos. AAQ89268.1, AAH17588.1, and AAK38275.1, which are all incorporated herein by reference. Non-limiting examples of nucleotide sequences for CXCL16 include NCBI Accession Nos. NM_001100812.1, NM_022059.3, and AF337812.1, which are incorporated herein by reference. In embodiments, a CXCL16 protein is a protein having amino acids in the sequence of one of the NCBI Accession numbers for CXCL16 disclosed herein, or an isoform or homologue thereof. In embodiments, a CXCL16 protein includes any protein having amino acids in the sequence of any one of one of the NCBI Accession numbers for CXCL16 disclosed herein, or an isoform or homologue thereof.

The term "PD-L2" as provided herein refers to programmed cell death 1 ligand 2, and includes homologues and isoforms thereof. Non-limiting examples of amino acid sequences for PD-L2 include NCBI Accession Nos. AAI13681.1, AAI13679.1, AAH74766.1, and NP_079515.2, which are all incorporated herein by reference. Non-limiting examples of nucleotide sequences for PD-L2 include NCBI Accession Nos. NM_025239.3, BC113680.1, BC113678.1, and AY254343.1, which are incorporated herein by reference. In embodiments, a PD-L2 protein is a protein having amino acids in the sequence of one of the NCBI Accession numbers for PD-L2 disclosed herein, or an isoform or homologue thereof. In embodiments, a PD-L2 protein includes any protein having amino acids in the sequence of any one of one of the NCBI Accession numbers for PD-L2 disclosed herein, or an isoform or homologue thereof.

The term "CKLF" as provided herein refers to chemokine like factor, and includes homologues and isoforms thereof. Non-limiting examples of amino acid sequences for CKLF include NCBI Accession Nos. AAQ89358.1, NP 857592.1, NP 857591.1, NP_058647.1, NP_001035228.1, and NP_057410.1, which are all incorporated herein by reference. Non-limiting examples of nucleotide sequences for CKLF include NCBI Accession Nos. NM_016951.3, NM_181641.2, NM_181640.2, NM_001040138.2, and NM_016326.3, which are incorporated herein by reference. In embodiments, a CKLF protein is a protein having amino acids in the sequence of one of the NCBI Accession numbers for CKLF disclosed herein, or an isoform or homologue thereof. In embodiments, a CKLF protein includes any protein having amino acids in the sequence of any one of one of the NCBI Accession numbers for CKLF disclosed herein, or an isoform or homologue thereof.

The term "OPG" as provided herein refers to Osteoprotegerin (also known as TNF Receptor Superfamily Member 11b or TNFRSF11B), and includes homologues and isoforms thereof. Non-limiting examples of amino acid sequences for OPG include NCBI Accession Nos. AAB53709.1, EAW91978.1, and NP_002537.3, which are all incorporated herein by reference. Non-limiting examples of nucleotide sequences for OPG include NCBI Accession Nos. NM_002546.3 and U94332.1, which are incorporated herein by reference. In embodiments, an OPG protein is a protein having amino acids in the sequence of one of the NCBI Accession numbers for OPG disclosed herein, or an isoform or homologue thereof. In embodiments, an OPG protein includes any protein having amino acids in the sequence of any one of one of the NCBI Accession numbers for OPG disclosed herein, or an isoform or homologue thereof.

The term "ICAM1" as provided herein refers to intercellular adhesion molecule 1, and includes homologues and isoforms thereof. Non-limiting examples of amino acid sequences for ICAM1 include NCBI Accession Nos. NP_000192.2 and AAH15969.1, which are all incorporated herein by reference. Non-limiting examples of nucleotide sequences for ICAM1 include NCBI Accession Nos. NM_000201.2 and AF340038.1, which are incorporated herein by reference. In embodiments, an ICAM1 protein is a protein having amino acids in the sequence of one of the NCBI Accession numbers for ICAM1 disclosed herein, or an isoform or homologue thereof. In embodiments, an ICAM1 protein includes any protein having amino acids in the sequence of any one of one of the NCBI Accession numbers for ICAM1 disclosed herein, or an isoform or homologue thereof.

The term "Eotaxin" as provided herein refers to C-C motif chemokine 11 (also known as CCL11), and includes homologues and isoforms thereof. Non-limiting examples of amino acid sequences for Eotaxin include NCBI Accession Nos. NP_002977.1, CAB07027.1, AAC51297.1, and AAC50369.1, which are all incorporated herein by reference. A non-limiting example of a nucleotide sequence for Eotaxin includes NCBI Accession No. NM_002986.2, which is incorporated herein by reference. In embodiments, an Eotaxin protein is a protein having amino acids in the sequence of one of the NCBI Accession numbers for Eotaxin disclosed herein, or an isoform or homologue thereof. In embodiments, an Eotaxin protein includes any protein having amino acids in the sequence of any one of one of the NCBI Accession numbers for Eotaxin disclosed herein, or an isoform or homologue thereof.

The term "CCL13" as provided herein refers to chemokine (C-C motif) ligand 13, and includes homologues and isoforms thereof. Non-limiting examples of amino acid sequences for CCL13 include NCBI Accession Nos. NP_005399.1, EAW80206.1, EAW80205.1, and AAH08621.1, which are all incorporated herein by reference. Non-limiting examples of nucleotide sequences for CCL13 include NCBI Accession Nos. NM_005408.2 and BC008621.1, which are incorporated herein by reference. In embodiments, a CCL13 protein is a protein having amino acids in the sequence of one of the NCBI Accession numbers for CCL13 disclosed herein, or an isoform or homologue thereof. In embodiments, a CCL13 protein includes any protein having amino acids in the sequence of any one of one of the NCBI Accession numbers for CCL13 disclosed herein, or an isoform or homologue thereof.

The term "IL2Ra" as provided herein refers to interleukin 2 receptor subunit alpha, and includes homologues and isoforms thereof. Non-limiting examples of amino acid sequences for IL2Ra include NCBI Accession Nos. NP_001295172.1, NP_001295171.1, NP_000408.1, EAW86414.1, EAW86413.1, and EAW86412.1, which are all incorporated herein by reference. Non-limiting examples of nucleotide sequences for L2Ra include NCBI Accession Nos. NM_001308243.1, NM_001308242.1, and NM_000417.2, which are incorporated herein by reference. In embodiments, an L2Ra protein is a protein having amino acids in the sequence of one of the NCBI Accession numbers for L2Ra disclosed herein, or an isoform or homologue thereof. In embodiments, an L2Ra protein includes any protein having amino acids in the sequence of any one of one of the NCBI Accession numbers for L2Ra disclosed herein, or an isoform or homologue thereof.

The term "IL7R" as provided herein refers to interleukin 7 receptor, and includes homologues and isoforms thereof. Non-limiting examples of amino acid sequences for L7R include NCBI Accession Nos. NP_002176.2, AAC83204.1, AAH69999.1, and EAW55924.1, which are all incorporated herein by reference. Non-limiting examples of nucleotide sequences for IL7R include NCBI Accession Nos. NM_002185.4 and NR_120485.2, which are incorporated herein by reference. In embodiments, an L7R protein is a protein having amino acids in the sequence of one of the NCBI Accession numbers for L7R disclosed herein, or an isoform or homologue thereof. In embodiments, an L7R protein includes any protein having amino acids in the sequence of any one of one of the NCBI Accession numbers for L7R disclosed herein, or an isoform or homologue thereof.

The term "CD44" as provided herein refers to CD44 antigen, and includes homologues and isoforms thereof. Non-limiting examples of amino acid sequences for CD44 include NCBI Accession Nos. ACI46596.1, CAA44602.1, NP 000601.3, NP 001001389.1, NP_001001390.1, NP_001001391.1, and NP_001001392.1 which are all incorporated herein by reference. Non-limiting examples of nucleotide sequences for CD44 include NCBI Accession Nos. NM_000610.3, NM_001001389.1, NM_001001390.1, NM_001001391.1, and NM_001001392.1, which are incorporated herein by reference. In embodiments, a CD44 protein is a protein having amino acids in the sequence of one of the NCBI Accession numbers for CD44 disclosed herein, or an isoform or homologue thereof. In embodiments, a CD44 protein includes any protein having amino acids in the sequence of any one of one of the NCBI Accession numbers for CD44 disclosed herein, or an isoform or homologue thereof.

The term "CXCL11" as provided herein refers to C-X-C motif chemokine 11, and includes homologues and isoforms thereof. Non-limiting examples of amino acid sequences for CXCL11 include NCBI Accession Nos. NP 001289052.1 and NP 005400.1, which are all incorporated herein by reference. Non-limiting examples of nucleotide sequences for CXCL11 include NCBI Accession Nos. NM_005409.4 and NM_001302123.1, which are incorporated herein by reference. In embodiments, a CXCL11 protein is a protein having amino acids in the sequence of one of the NCBI Accession numbers for CXCL11 disclosed herein, or an isoform or homologue thereof. In embodiments, a CXCL11 protein includes any protein having amino acids in the sequence of any one of one of the NCBI Accession numbers for CXCL11 disclosed herein, or an isoform or homologue thereof.

The term "NFATC4" as provided herein refers to Nuclear Factor Of Activated T-Cells 4, and includes homologues and isoforms thereof. Non-limiting examples of amino acid sequences for NFATC4 include NCBI Accession Nos. NP_004545.2, NP_001129494.1, NP_001185894.1, NP_001185895.1, and NP_001185896.1, which are all incorporated herein by reference. Non-limiting examples of nucleotide sequences for NFATC4 include NCBI Accession Nos. NM_001136022.2, NM_001198965.1, NM_001198966.2, NM_001198967.2, and NM_001288802.1, which are incorporated herein by reference. In embodiments, a NFATC4 protein is a protein having amino acids in the sequence of one of the NCBI Accession numbers for NFATC4 disclosed herein, or an isoform or homologue thereof. In embodiments, a NFATC4 protein includes any protein having amino acids in the sequence of any one of one of the NCBI Accession numbers for NFATC4 disclosed herein, or an isoform or homologue thereof.

The term "CD73" as provided herein refers to cluster of differentiation 73 (also known as ecto-5'-nucleotidase or NT5E) and includes homologues and isoforms thereof. Non-limiting examples of amino acid sequences for CD73 include NCBI Accession Nos. AAH65937.1, NP_002517.1, and NP_001191742.1, which are all incorporated herein by reference. Non-limiting examples of nucleotide sequences for CD73 include NM_002526.3, and NM_001204813.1, which are incorporated herein by reference. In embodiments, a CD73 protein is a protein having amino acids in the sequence of one of the NCBI Accession numbers for CD73 disclosed herein, or an isoform or homologue thereof. In embodiments, a CD73 protein includes any protein having amino acids in the sequence of any one of one of the NCBI Accession numbers for CD73 disclosed herein, or an isoform or homologue thereof. CD73 is an enzyme that catalyzes conversion of adenosine monophosphate to adenosine, and thus contributes towards local adenosine concentration.

A "memory T cell" is a T cell that has previously encountered and responded to its cognate antigen during prior infection, encounter with cancer or previous vaccination. At a second encounter with its cognate antigen memory T cells can reproduce (divide) to mount a faster and stronger immune response than the first time the immune system responded to the pathogen. In embodiments, the memory T cell is a CD45RA-negative CD4 T cell. In embodiments, the memory T cell is a CD45RA-negative CD8 T cell.

A "regulatory T cell" or "suppressor T cell" is a lymphocyte which modulates the immune system, maintains tolerance to self-antigens, and prevents autoimmune disease. Regulatory T cells express the CD4, FOXP3, and CD25 and are thought to be derived from the same lineage as naïve CD4 cells.

A "fixation agent" is a chemical or molecular agent capable of fixing a cell (e.g. of preserving a cell). A fixation agent can be used to prevent further biological process in preparation for cell staining, imaging or sorting. Fixation agents can be used alone or in combination. Non-limiting examples of fixation agents include formaldehyde, glutaraldehyde, ethanol, methanol, Potassium dichromate, chromic acid, and potassium permanganate, B-5, Zenker's fixative, picrates, and HOPE.

"Anti-PD-1 pathway refractory subject" or "refractory subject" or "IO-refractory subject" refer to cancer patients who are unresponsive to PD-1 pathway inhibitor therapy, such as treatment with PD-1 inhibitors and/or PD-L1 inhibitors. Generally, a refractory subject has been treated with a PD-1 pathway inhibitor (e.g., PD-1 inhibitor, PD-L1 inhibitor) for one month, two months, or three months, and was unresponsive to treatment with the PD-1 pathway inhibitor. Where the cancer patient is unresponsive to PD-1 pathway inhibitor therapy the patient shows less than 20% reduction in tumor size or volume after administration of PD-1 pathway inhibitor relative to a control. In embodiments, an anti-PD-1 refractory subject shows less than 10% reduction in tumor size or volume after administration of PD-1 pathway inhibitor relative to a control. In embodiments, an anti-PD-1 refractory subject shows less than 5% reduction in tumor size or volume after administration of PD-1 pathway inhibitor relative to a control. In embodiments, an anti-PD-1 refractory subject shows less than 1% reduction in tumor size or volume after administration of PD-1 pathway inhibitor relative to a control. In embodiments, an anti-PD-1 refractory subject shows less than 0.5% reduction in tumor size or volume after administration of PD-1 pathway inhibitor relative to a control. In embodiments, an anti-PD-1 refractory subject shows less than 0.1% reduction in tumor size or volume after administration of PD-1 pathway inhibitor relative to a control. In embodiments, an anti-PD-1 refractory subject shows no reduction in tumor size or volume after administration of PD-1 pathway inhibitor relative to a control. In embodiments, an anti-PD-1 refractory subject shows an increase in tumor size or volume after administration of PD-1 pathway inhibitor relative to a control.

"Anti-PD-1 pathway resistant subject" or "resistant subject" or "IO-resistant subject" refer to cancer patients who are initially responsive to PD-1 pathway inhibitor therapy, but then became resistant to PD-1 pathway inhibitor therapy (e.g., PD-1 inhibitor, PD-L1 inhibitor). "Resistant subjects" have been treated with PD-1 pathway inhibitor therapy for more than three months. The "anti-PD-1 resistant subject" initially showed some benefits from the PD-1 pathway inhibitor therapy, where the benefits could have been: (i) an increase over baseline of one or more of CD8+ cell infiltration, T cell activation, interferon-gamma pathway gene expression, and T cell clone expansion; (ii) a cancerous tumor that did not grow in size or volume; (iii) a cancerous tumor that decreased in size or volume; (iv) a cancerous tumor that did not metastasize; or (v) a combination of two or more of the foregoing. After initially showing a benefit to treatment, the "resistant subject" then became unresponsive to the PD-1 pathway inhibitor therapy, such as treatment with PD-1 inhibitors and/or PD-L1 inhibitors. Where the cancer patient is unresponsive to PD-1 pathway inhibitor therapy, the patient shows less than 20% reduction in tumor size or volume after administration of PD-1 pathway inhibitor relative to a control. Thus, in embodiments, an anti-PD-1 resistant subject shows less than 20% reduction in tumor size or volume after administration of PD-1 pathway inhibitor relative to a control. In embodiments, an anti-PD-1 resistant subject shows less than 10% reduction in tumor size or volume after administration of PD-1 pathway inhibitor relative to a control. In embodiments, an anti-PD-1 resistant subject shows less than 5% reduction in tumor size or volume after administration of PD-1 pathway inhibitor relative to a control. In embodiments, an anti-PD-1 resistant subject shows less than 1% reduction in tumor size or volume after administration of PD-1 pathway inhibitor relative to a control. In embodiments, an anti-PD-1 resistant subject shows less than 0.5% reduction in tumor size or volume after administration of PD-1 pathway inhibitor relative to a control. In embodiments, an anti-PD-1 resistant subject shows less than 0.1% reduction in tumor size or volume after administration of PD-1 pathway inhibitor relative to a control. In embodiments, an anti-PD-1 resistant subject shows no reduction in tumor size or volume after administration of PD-1 pathway inhibitor relative to a control. In embodiments, an anti-PD-1 resistant subject shows an increase in tumor size or volume after administration of PD-1 pathway inhibitor relative to a control.

"Subject naïve to PD-1 pathway inhibitor therapy" or "IO-naïve" refer to a subject that had not previously been treated with PD-1 pathway inhibitor therapy, such as PD-1 inhibitors or PD-L1 inhibitors.

The term "anti-tumor immune memory" as provided herein refers to the ability of the immune system of a subject to recognize (memorize) previously encountered tumor antigen. Once the tumor antigen has been recognized, the immune system reproduces (e.g., through T cell activation and proliferation) and can mount a faster and stronger immune response than the first time it responded to the same tumor antigen.

The term "global immune activation" as provided herein refers to the activation of immune cells of the adaptive immune system in a subject. Examples of immune cells activated during global immune activation are without limitation, antigen presenting cells (macrophages, dendritic cells), B cells and T cells. The activation may occur through recognition of a previously encountered antigen (tumor antigen) or it may occur through encounter of a novel (not previously encountered) antigen (tumor antigen).

The terms "disease" or "condition" refer to a state of being or health status of a patient or subject capable of being treated with a compound, pharmaceutical composition, or method provided herein. In embodiments, the disease is cancer (e.g., non-small cell lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). In embodiments, the disease is non-small cell lung cancer or renal cell carcinoma. The disease may be an autoimmune, inflammatory, cancer, infectious, metabolic, developmental, cardiovascular, liver, intestinal, endocrine, neurological, or other disease.

A "control" sample or value refers to a sample that serves as a reference, usually a known reference, for comparison to a test sample. For example, a test sample can be taken from a patient suspected of having a given disease (cancer) and compared to samples from a known cancer patient, or a known normal (non-disease) individual. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters. In embodiments, a control is a negative control. In embodiments, such as some embodiments relating to detecting the level of expression or infiltration, a control comprises the average amount of expression (e.g., protein or mRNA) of infiltration (e.g., number or percentage of cells in a population of cells) in a population of subjects (e.g., with cancer) or in a healthy or general population. In embodiments, the control comprises an average amount (e.g. percentage or number of infiltrating cells or amount of expression) in a population in which the number of subjects (n) is 5 or more, 6 or more, 7 or more, 8 or more, 9 or more, 10 or more, 25 of more, 50 or more, 100 or more, 1000 or more, 5000 or more, or 10000 or more. In embodiments, the control is a standard control.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma *villosum*.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer, testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

The terms "patient," "individual," "subject," and the like are interchangeable and refer to a living organism suffering from or who is a member of a species that may suffer from a disease or condition that can be treated by administration of a compound, composition or pharmaceutical composition as provided herein. Non-limiting examples include primates (such as humans, monkeys, and chimpanzees), other mammals (such as bovines, rats, mice, dogs, goat, sheep, cows, and deer), and other non-mammalian animals. In embodiments, a patient is human. In embodiments, a patient is a mammal. In embodiments, a patient is a dog. Thus, the methods are applicable to both human therapy and veterinary applications. In embodiments, an individual described as a "patient" does not necessarily have a given disease, but may be merely seeking medical advice. In embodiments, and depending on context, a "subject in need thereof" is a subject who has one or more risk factors for a cancer or cancer outcome. In embodiments, and depending on context, a "subject in need thereof" is a subject who has cancer (e.g., who has been diagnosed with cancer by a medical professional). In embodiments, and depending on context, a "subject in need thereof" is a subject who is suspected of having or who has a refractory or resistant cancer disclosed herein. In embodiments, and depending on context, a "subject in need thereof" is a subject who has not responded to a previous cancer treatment, an PD-1 pathway refractory subject, or a PD-1 pathway resistant subject.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

Methods of Treating Cancer

The methods provided herein are, inter alia, useful for the treatment of cancer. Cancer treatment can include administration of an anti-cancer agent. In embodiments, treatment of cancer comprises, consists essentially of, or consists of treating a cancer tumor. In embodiments, treatment of cancer comprises reducing the size of a cancer tumor or reducing the growth of a cancer tumor. In embodiments, treatment of cancer comprises increasing a subject's immune response to a cancer (e.g., a cancer antigen). In embodiments, treatment of cancer comprises increasing T cell infiltration (e.g., CD8 T cell infiltration) into a cancer tumor. In embodiments, an anti-cancer agent includes an adenosine receptor antagonist, alone or in combination with a programmed cell death protein 1 (PD-1) signaling pathway inhibitor. In embodiments, an adenosine receptor antagonist is an adenosine-A2A receptor antagonist. Through administration of a therapeutically effective amount of an adenosine-A2A receptor antagonist alone or in combination with a PD-1 signaling pathway inhibitor cancer may be treated in a subject in need thereof.

In embodiments, treating a cancer tumor includes preventing an increase in size or volume of the cancer tumor. In embodiments, treating a cancer tumor includes decreasing the size of volume of a cancer tumor. In embodiments, treating a cancer tumor includes eliminating the cancer tumor altogether. In embodiments, a cancer tumor is eliminated when it is not detectable by an imaging test such as magnetic resonance imaging (MRI), a positron emission tomography (PET) scan, X-ray computed tomography (CT), ultrasound, or single-photon emission computed tomography (SPECT). In embodiments, treating a cancer tumor further comprises reducing or preventing metastasis of the cancer tumor.

In embodiments, the cancer tumor is a solid tumor. In embodiments, the solid tumor is a sarcoma or carcinoma solid tumor. In embodiments, the solid tumor is a lymphoma solid tumor. In embodiments, the solid tumor is a melanoma solid tumor. In embodiments, the cancer is not a leukemia.

In embodiments, the solid tumor is bladder cancer, breast cancer, clear cell kidney cancer, head/neck squamous cell carcinoma, lung squamous cell carcinoma, melanoma, malignant melanoma, non-small-cell lung cancer (NSCLC), ovarian cancer, pancreatic cancer, prostate cancer, renal cell cancer (such as renal cell carcinoma), small-cell lung cancer (SCLC) or triple negative breast cancer. In embodiments, the subject is human. In embodiments, the subject is a refractory subject. In embodiments, the subject has had less than a 15% reduction (e.g., less than a 15%, 10%, or 5% reduction) in tumor volume after administration of anti-PD-1 compound. In embodiments, an anti-PD-1 compound was initially effective to reduce tumor volume by more than 15%, and then the tumor became resistant to the compound and continued increasing in volume. In embodiments, the refractory subject has a tumor that has increased in volume after administration of an anti-PD-1 compound. In embodiments, the anti-PD-1 compound is atezolizumab. In embodiments, the subject has nivolumab refractory cancer. In embodiments, the nivolumab refractory cancer is nivolumab refractory renal cancer (such as nivolumab refractory renal cell cancer, e.g., renal cell carcinoma). In embodiments, the cancer is resistant to pembrolizumab, a tyrosine kinase inhibitor, or an mTOR inhibitor. Non-limiting examples of tyrosine kinase inhibitors include imatinib, gefitinib, erlotinib, sunitinib, and cabozantinib. Non-limiting examples of mTOR inhibitors include rapamycin, rapamycin analogs such as rapalogs, e.g., temsirolimus, deforolimus, everolimus, and ridaforolimus, and ATP-competitive mTOR kinase inhibitors.

In embodiments, the cancer tumor comprises elevated levels of tumor infiltrating lymphocytes relative to a control, the cancer tumor comprises an elevated level of PD-L1 relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity or blood T cell receptor diversity relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity or blood T cell receptor diversity relative to a control, the cancer tumor comprises an elevated level of PD-L1 relative to a control, and the cancer tumor or the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity or blood T cell receptor diversity relative to a control, the cancer tumor comprises an elevated level of PD-L1 relative to a control, and the subject has an increased level of a T-effector signature compared to a control. In embodiments, the tumor infiltrating lymphocytes are CD8 T cells.

In embodiments, the subject comprises an increased cancer tumor T cell receptor diversity or blood T cell receptor diversity relative to a control, the cancer tumor comprises an elevated level of PD-L1 relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity or blood T cell receptor diversity relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity or blood T cell receptor diversity relative to a control, the cancer tumor comprises an elevated level of PD-L1 relative to a control, and the cancer tumor or the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity or blood T cell receptor diversity relative to a control, the cancer tumor comprises an elevated level of PD-L1 relative to a control, and the subject has an increased level of T-effector signature compared to a control. In embodiments, the tumor infiltrating lymphocytes are CD8 T cells.

In embodiments, the subject comprises an increased cancer tumor T cell receptor diversity or blood T cell receptor diversity relative to a control, the cancer tumor comprises an elevated level of PD-L1 relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control, the cancer tumor comprises an elevated level of PD-L1 relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity or blood T cell receptor diversity relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity or blood T cell receptor diversity relative to a control, the cancer tumor comprises an elevated level of PD-L1 relative to a control, and the subject has an increased level of a T-effector signature compared to a control. In embodiments, the tumor infiltrating lymphocytes are CD8 T cells.

In embodiments, the cancer tumor comprises an elevated level of PD-L1 relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control and the cancer tumor or the blood of the subject comprises an elevated level of CD73 relative to a control. In embodiments, the subject comprises an increased cancer tumor T cell receptor diversity or blood T cell receptor diversity relative to a control, and the cancer tumor or the blood of the subject comprises an elevated level of CD73 relative to a control. In embodiments, the cancer tumor comprises an elevated level of PD-L1 relative to a control, the subject has an increased level of a T-effector signature compared to a control, and the cancer tumor or the blood of the subject comprises an elevated level of CD73 relative to a control. In embodiments, the cancer tumor comprises an elevated level of PD-L1 relative to a control and the cancer tumor or the blood of the subject comprises an elevated level of CD73 relative to a control. In embodiments, the tumor infiltrating lymphocytes are CD8 T cells.

In embodiments, the cancer tumor comprises elevated levels of tumor infiltrating lymphocytes relative to a control, the subject comprises an increased cancer tumor T cell receptor diversity or blood T cell receptor diversity relative to a control, the cancer tumor comprises an elevated level of PD-L1 relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity and blood T cell receptor diversity relative to a control, the cancer tumor comprises an elevated level of PD-L1 relative to a control, the subject has an increased level of a T-effector signature compared to a control, and the cancer tumor or the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity or blood T cell receptor diversity relative to a control, the cancer tumor comprises an elevated level of PD-L1 relative to a control, the subject has an increased level of a T-effector signature compared to a control, and the cancer tumor and the blood of the subject comprises an elevated level of CD73 relative to a control. In embodiments, the cancer tumor comprises elevated levels of tumor infiltrating lymphocytes relative to a control, the subject comprises an increased cancer tumor T cell receptor diversity and blood T cell receptor diversity relative to a control, the cancer tumor comprises an elevated level of PD-L1 relative to a control, the subject has an increased level of a T-effector signature compared to a control, and the cancer tumor and the blood of the subject comprises an elevated level of CD73 relative to a control. In embodiments, the tumor infiltrating lymphocytes are CD8 T cells.

In embodiments, the cancer tumor comprises an elevated level of tumor infiltrating lymphocytes relative to a control, an elevated level of a T cell gene signature relative to a control, increased T cell receptor diversity in the blood or cancer tumor (e.g., in whole blood, serum, plasma, or cells obtained from blood, or a tumor biopsy) relative to a control, cancer tumor comprises an elevated level of PD-L1 (e.g., relative to a control), and/or the cancer tumor or the blood (e.g., whole blood or a portion thereof such as serum or plasma) of the subject comprises an elevated level of CD73 (e.g., relative to a control). In embodiments, the cancer tumor comprises an elevated level of tumor infiltrating lymphocytes relative to a control, an elevated level of a T cell gene signature relative to a control, increased T cell receptor diversity in the blood or cancer tumor (e.g., in whole blood, serum, plasma, or cells obtained from blood, or a tumor biopsy) relative to a control, the cancer tumor comprises an elevated level of PD-L1 (e.g., relative to a control), and/or the cancer tumor or the blood (e.g., whole blood or a portion thereof such as serum or plasma) of the subject comprises an elevated level of CD73 (e.g., relative to a control) prior to administration of the A2A receptor antagonist. In embodiments, the cancer tumor comprises an elevated level of tumor infiltrating lymphocytes relative to a control, an elevated level of a T cell gene signature relative to a control, increased T cell receptor diversity in the blood or cancer tumor (e.g., in whole blood, serum, plasma, or cells obtained from blood, or a tumor biopsy) relative to a control, the cancer tumor comprises an elevated level of PD-L1 (e.g., relative to a control), and/or the cancer tumor or the blood (e.g., whole blood or a portion thereof such as serum or plasma) of the subject comprises an elevated level of CD73 (e.g., relative to a control) after administration of the adenosine A2A receptor antagonist. In embodiments, the tumor infiltrating lymphocytes are CD8 T cells. In embodiments, the T cell gene signature is a subset of genes that comprise this signature.

Included herein is a method of treating a cancer tumor in a subject in need thereof, the method comprising (i) determining whether (a) the cancer tumor comprises elevated levels of tumor infiltrating lymphocytes (TILs) relative to a control, (b) the subject comprises an increased cancer tumor T cell receptor diversity or blood T cell receptor diversity relative to a control, (c) the cancer tumor comprises an elevated level of PD-L1 relative to a control, (d) the subject has an increased level of a T-effector signature compared to a control, or (e) the cancer tumor or the blood of the subject comprises an elevated level of CD73 relative to a control; and (ii) administering to the subject a therapeutically effective amount of an adenosine-A2A receptor antagonist. In embodiments, determining whether (a) the cancer tumor comprises elevated levels of tumor infiltrating lymphocytes relative to a control, (b) the subject comprises an increased cancer tumor T cell receptor diversity or blood T cell receptor diversity relative to a control, (c) the cancer tumor comprises an elevated level of PD-L1 relative to a control, (d) the subject has an increased level of a T-effector signature compared to a control, or (e) the cancer tumor or the blood of the subject comprises an elevated level of CD73 relative to a control comprises obtaining a biological sample from the subject. In embodiments, the biological sample comprises a tumor biopsy, whole blood, serum, or plasma. In embodiments, determining whether the cancer tumor comprises elevated levels of tumor infiltrating lymphocytes comprises detecting a T-effector signature. In embodiments, the tumor infiltrating lymphocytes are CD8 T cells. In embodiments, the T-effector signature is a subset of genes that comprise this signature.

In embodiments, pre-existing T cell (e.g., CD8 T cell) infiltration or activation is not required for tumor regression with either single agent or combination regimens disclosed herein. In embodiments, inhibition of A2AR signaling stimulates T cell infiltration and activation in the tumor microenvironment in both inflamed and non-inflamed tumors. In embodiments, adenosine suppresses immunity and is a mechanism of resistance to PD-(L)1 therapy. In embodiments, subjects with an increased level of CD73 expression (e.g., in peripheral blood and/or tumor cells, such as in a biopsy) are resistant to anti-PD-1 therapy. In embodiments, subjects who are resistant to anti-PD-1 therapy are administered an A2A receptor antagonist. In embodiments, an A2A receptor antagonist induces (e.g., is administered in an amount that is effective to induce) CD8 T-cell infiltration and Th1 gene expression in tumor tissues. In embodiments, an A2A receptor antagonist induces (e.g., is administered in an amount that is effective to induce) expansion of identical T-cell clones in blood and tumor. In embodiments, an A2A receptor antagonist is well tolerated as a monotherapy and in combination with atezolizumab. In embodiments, an A2A receptor antagonist has clinical activity alone and in combination with atezolizumab. In embodiments, an effective amount of an A2A receptor antagonist has anti-tumor activity in patients who have progressed after receiving anti-PD-L1 therapy (e.g., during an anti-PD-L1 treatment regimen). In embodiments, an effective amount of an A2A receptor antagonist has anti-tumor activity in patients with PD-L1 negative tumors. In embodiments, an effective amount of an A2A receptor antagonist has anti-tumor activity in patients who have an increased level of CD73 expression (e.g., in peripheral blood and/or tumor cells, such as in a biopsy).

In embodiments, the cancer tumor comprises an elevated level of tumor infiltrating lymphocytes relative to a control. As used herein, an elevated level of tumor infiltrating lymphocytes may include an elevated level of the number of tumor infiltrating lymphocytes and/or an elevated level of tumor infiltrating lymphocyte activity. In embodiments, the tumor infiltrating lymphocytes are tumor infiltrating T cells. In embodiments, the T cells are CD8 T cells. In embodiments, at least about 0.5%, 1%, 2%, 3%, 4%, 5%, 6%, 7%, 8%, 9%, 10%, 4%-5%, 4%-6%, 4%-7%, 4%-8%, 4%-9%, or 4%-10% of the tumor area in a region of the tumor are CD8 T cells. In embodiments, at least about 1% of the cells in a region of the tumor are CD8 T cells. In embodiments, at least about 2% of the cells in a region of the tumor are CD8 T cells. In embodiments, at least about 3% of the cells in a region of the tumor are CD8 T cells. In embodiments, at least about 4% of the cells in a region of the tumor are CD8 T cells. In embodiments, at least about 5% of the cells in a region of the tumor are CD8 T cells. In embodiments, at least about 6% of the cells in a region of the tumor are CD8 T cells. In embodiments, at least about 7% of the cells in a region of the tumor are CD8 T cells. In embodiments, at least about 8% of the cells in a region of the tumor are CD8 T cells. In embodiments, at least about 9% of the cells in a region of the tumor are CD8 T cells. In embodiments, at least about 10% of the cells in a region of the tumor are CD8 T cells. In embodiments, the region is the center of the cancer tumor. In embodiments, the tumor infiltrating lymphocytes (such CD8 T cells) are detected by immunohistochemistry. In embodiments, CD8 T cells are detected by immunohistochemistry (e.g., comprising an anti-CD8 antibody). In embodiments, the T cells are effector memory T cells. In embodiments, the tumor tissue has an increased level of CD8a, CXCL9, CXCL10, EOMES, IFNγ, GZMA, GZMB, TBX21, PD-L1, CXCL16, PD-L2, CKLF, OPG, ICAM1, Eotaxin, CCL13, IL2Ra, IL7R, and/or CD44 expression (e.g., compared to a control). In embodiments, the tumor tissue has an increased level of CD8a expression compared to a control. In embodiments, the tumor tissue has an increased level of CXCL9 expression compared to a control. In embodiments, the tumor tissue has an increased level of CXCL10 expression compared to a control. In embodiments, the tumor tissue has an increased level of EOMES expression compared to a control. In embodiments, the tumor tissue has an increased level of IFNγ expression compared to a control. In embodiments, the tumor tissue has an increased level of GZMA expression compared to a control. In embodiments, the tumor tissue has an increased level of GZMB expression compared to a control. In embodiments, the tumor tissue has an increased level of TBX21 expression compared to a control. In embodiments, the tumor tissue has an increased level of PD-L1 expression compared to a control. In embodiments, the tumor tissue has an increased level of CXCL16 expression compared to a control. In embodiments, the tumor tissue has an increased level of PD-L2 expression compared to a control. In embodiments, the tumor tissue has an increased level of CKLF expression compared to a control. In embodiments, the tumor tissue has an increased level of OPG expression compared to a control. In embodiments, the tumor tissue has an increased level of ICAM1 expression compared to a control. In embodiments, the tumor tissue has an increased level of Eotaxin expression compared to a control. In embodiments, the tumor tissue has an increased level of CCL13 expression compared to a control. In embodiments, the tumor tissue has an increased level of IL2Ra expression compared to a control. In embodiments, the tumor tissue has an increased level of IL7R expression compared to a control. In embodiments, the tumor tissue has an increased level of CD44 expression compared to a control.

In embodiments, an elevated level of tumor infiltrating lymphocytes comprises an elevated level of a T-effector gene signature or a subset of genes that comprise the T-effector gene signature. In embodiments, determining the level of tumor infiltrating lymphocytes comprises detecting (e.g., by assaying) CD8+ cells by immunohistochemistry. In embodiments, determining the level of tumor infiltrating lymphocyte activation comprises detecting (e.g., by assaying) a T-effector signature. Included herein are T-effector gene signature biomarkers that are predictive of tumor response to therapy with A2A receptor antagonists. In embodiments, a T-effector gene signature (also referred to herein as a T-effector signature or a T cell gene signature) comprises, consists essentially of, or consists of an increased level of expression of CD8a, CXCL9, CXCL10, EOMES, IFNγ, GZMA, GZMB, or TBX21 in a cancer tumor (e.g., a sample obtained from a cancer tumor such as a biopsy) compared to a control or reference value. In embodiments, a T-effector gene signature (also referred to herein as a T-effector signature or a T cell gene signature) comprises, consists essentially of, or consists of an increased level of expression of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, or CD44 in a cancer tumor (e.g., a sample obtained from a cancer tumor such as a biopsy) compared to a control or reference value. In embodiments, the T-effector gene signature comprises 1, 2, 3, 4, 5, 6, 7, 8, or 9 of CD8a, CXCL9, CXCL10, EOMES, IFNγ, GZMA, GZMB, and/or TBX21. In embodiments, the T-effector gene signature comprises 1 or 2 of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, and/or CD44. In embodiments, the T-effector gene signature comprises 1, 2, 3, 4, 5, 6, 7, 8, 9, 10, or more genes in addition to 1 or any combination of CD8a, CXCL9, CXCL10, EOMES, IFNγ, GZMA, GZMB, and/or TBX21. In embodiments, the T-effector gene signature comprises 1, 2, 3, 4, 5, 6, 7, 8, 9, 10, or more genes in addition to 1 or any combination of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, and/or CD44 such as STAT1. In embodiments, detecting a T-effector signature comprises use of the Fluidigm real-time PCR platform. In embodiments, the T-effector signature is a composite T-effector signature. In embodiments, a composite T-effector Signature comprises, consists essentially of, or consists of an increase in the expression of any combination of 2, 3, 4, 5, 6, 7, or 8 of CD8a, CXCL9, CXCL10, EOMES, IFNγ, GZMA, GZMB, and TBX21 compared to a control or reference value. In embodiments, a composite T-effector Signature comprises, consists essentially of, or consists of an increase in the expression of any combination of 2, 3, 4, 5, 6, 7, 8, 9, 10, 11, 12, 13, 14, 15, 16, 17, or 18, of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, and CD44 compared to a control or reference value. One exemplary composite T-effector signature comprises CXCL10, GZMA, and GZMB. In embodiments, a combination of at least about five of CD8a, CXCL9, CXCL10, EOMES, IFNγ, GZMA, GZMB, and TBX21 is selected for use as predictive T-effector signature biomarkers. In embodiments, a combination of at least about five of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, and CD44 is selected for use as predictive T-effector signature biomarkers. In embodiments, the T-effector gene signature consists of CD8a, CXCL9, CXCL10, EOMES, IFNγ, GZMA, GZMB, and TBX21. In embodiments, the T-effector gene signature consists of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, and CD44. In embodiments, the tumor sample is from a subject who is treatment naïve for A2A receptor antagonist therapy. In embodiments, the tumor sample is from a subject who has been administered an A2A receptor antagonist. In embodiments, to assess whether such a subject's tumor is likely to respond to a A2A receptor antagonist, the calculated score for the tumor sample is compared to a reference score for the T-effector gene signature that has been pre-selected to divide at least the majority of responders to A2A receptor antagonist therapy from at least the majority of non-responders to A2A receptor antagonist therapy. In embodiments, if the subject has an T-effector gene signature score that is equal to or a greater than the reference T-effector gene signature score, the subject is more likely to respond, or to achieve a better response, to the A2A receptor antagonist than if the subject's T-effector gene signature score is less than the reference score. In embodiments, a T-effector gene signature score for a tumor sample of interest is calculated as the arithmetic mean of normalized mRNA or protein expression levels, in the tumor sample, for each of the genes in the gene signature. In embodiments, the T-effector Signature score is the geometric mean of expression values (e.g., normalized mRNA or protein expression levels) for CD8a, CXCL9, CXCL10, EOMES, IFNγ, GZMA, GZMB, or TBX21. In embodiments, the T-effector Signature score is the geometric mean of expression values (e.g., normalized mRNA or protein expression levels) for CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, or CD44. In embodiments, the geometric mean is calculated by multiplying numbers together and then take a square root (for two numbers), cube root (for three numbers) etc. (calculable as the n th root of a product of n numbers). In embodiments, determining the level of tumor infiltrating lymphocytes comprises detecting a T-effector signature and/or calculating a T-effector signature Score. In embodiments, the tumor infiltrating lymphocytes are CD8 T cells. In embodiments, a tumor is scored as above or below the median or mean for expression of a gene (or genes) in a T-effector signature for a plurality of tumors, and patients with tumors scoring above the median or mean are identified as likely to respond to administration of an A2A receptor antagonist.

In embodiments, the cancer tumor comprises increased cancer tumor T cell receptor diversity relative to a control. In embodiments, the cancer tumor comprises increased cancer tumor T cell receptor diversity after administration of anti-cancer agent compared to before administration of the anti-cancer agent. In embodiments, the T cell receptor diversity is TCRβ diversity. In embodiments, T cell receptor diversity is counter to T cell clonality (with increased clonality indicating lower diversity and decreased clonality indicating higher diversity). In embodiments, two T cells that comprise an identical genomic sequence that encodes TCRβ are "clones" of each other, whereas two T cells that comprise different genomic sequences that encode TCRβ are not clones of each other. In embodiments, the level of T cell clonality is assayed. In embodiments, the level of T cell receptor clonality is determined by a process comprising detecting the nucleic acid sequences coding for TCRβ in a biological sample (such as a tumor biopsy, blood, plasma, or serum, or cells such as PBMCs obtained from blood). In embodiments, clonality is a measure of the frequency of sequences that code for TCRβ. In embodiments, the level of T cell receptor clonality is determined by a process comprising detecting the amino acid sequences for TCRβ that are encoded in a biological sample (such as a tumor biopsy, blood, plasma, or serum, or cells such as PBMCs obtained from blood). In embodiments, T cell receptor clonality is a measure of the clonality of genetic sequences for TCRβ that are encoded. In embodiments, T cell receptor clonality is expressed as the dominance of different TCRβ genetic sequences that are present. In embodiments, clonality is expressed as a Simpson's Diversity Index value. Non-limiting descriptions relating to the Simpson's Diversity Index are provided in Venturi et al. (2007) *J Immunol Methods* 321:182-195, the entire content of which is incorporated herein by reference. In embodiments, the clonality of PBMCs (e.g., of T cells within a population of PBMCs) in a subject is less than about 0.1, 0.2, 0.3, 0.4, 0.5, 0.6, 0.7, 0.8, 0.9, or 1.0 prior to administration of the anti-cancer agent. In embodiments, the clonality of PBMCs (e.g., of T cells within a population of PBMCs) in a subject is less than about 0.1, 0.2, 0.3, 0.4, 0.5, 0.6, 0.7, 0.8, 0.9, or 1.0 after administration of the anti-cancer agent. In embodiments, the Morisita Index of PBMCs in the subject is at least about 0.2, 0.3, 0.4, 0.5, 0.6, 0.7, 0.8, 0.9, or 1.0, or is about 0.2, 0.3, 0.4, 0.5, 0.6, 0.7, or 0.8 to about 0.9 after administration of the anti-cancer agent compared to a pre-treatment sample.

Clonality is a measure of the dominance of specific T cell clones within a sample. It can range from 0-1, with 0 meaning each clone appears only once and 1 meaning the sample has only copies of a single clone. Clonality does not indicate the number of clones. Clonality<0.2 is within the normal range, >0.2 means that a few clones dominate the sample. Clonality is conceptually the opposite of diversity. A clonality<0.2 is diverse because there a lot of different clones and the sample is not dominated by one or a few clone. In embodiments, diversity within the normal range is more likely to have tumor regression or changes in repertoire.

A Morisita Index score indicates the similarity between two samples. In embodiments, the Morisita Index score is used to test whether pre- and post-treatment samples are similar or treatment induced changes in the T cell repertoire. The Morisita Index can range from 0-1, with 0 meaning the samples are completely different (no shared clones) and a score of 1 meaning the samples are the same. In embodiments, a Morisita Index score>0.9 means very little change (e.g., within the range of sample to sample variation), while a Morisita Index score<0.9 means there was a change within the sample.

In embodiments, the cancer tumor comprises an elevated level of PD-L1. In embodiments, the level of PD-L1 (e.g., the absolute level of PD-L1) is measured in immune cells and/or tumor cells. In embodiments, the level of PD-L1 (e.g., the absolute level of PD-L1) is measured in immune cells and/or tumor cells by immunohistochemistry. In embodiments, the cancer tumor comprises an elevated level of PD-L1 relative to a control. In embodiments, the control is a negative control. In embodiments, the elevated level is an increase of at least about 1%, 5%, 10%, 15%, 20%, 25%, 30%, 35%, 40%, 45%, 50%, 55%, 60%, 65%, 70%, 75%, 80%, 85%, 90%, 100%, 2-fold, 5-fold, 10-fold, 20-fold, or 100-fold compared to the control. In embodiments, the elevated level is an increase of at least about 5%-50%, 50%-100%, or 75-200% compared to the control. In embodiments, the elevated level is an increase of at least about 1% compared to the control. In embodiments, the elevated level is an increase of at least about 5% compared to the control. In embodiments, the elevated level is an increase of at least about 10% compared to the control. In embodiments, the elevated level is an increase of at least about 15% compared to the control. In embodiments, the elevated level is an increase of at least about 25% compared to the control. In embodiments, the elevated level is an increase of at least about 50% compared to the control. In embodiments, the elevated level is an increase of at least about 75% compared to the control. In embodiments, the elevated level is an increase of at least about 100% compared to the control. In embodiments, the elevated level is an increase of at least about 2-fold compared to the control. In embodiments, the elevated level is an increase of at least about 5-fold compared to the control. In embodiments, the elevated level is an increase of at least about 10-fold compared to the control. In embodiments, the cancer tumor comprises an elevated level of PD-L1 in tumor infiltrating lymphocytes relative to a control. In embodiments, the tumor infiltrating lymphocytes are CD8 T cells. In embodiments, the cancer tumor comprises an elevated level of PD-L1 in all tumor cells (e.g., in the tumor cell population taken as a whole) relative to a control. In embodiments, the increased level of PD-L1 is an increased level of PD-L1 mRNA (i.e., mRNA that encodes PD-L1). In embodiments, the increased level of PD-L1 is an increased level of PD-L1 protein. In embodiments, the level of PD-L1 is measured by immunohistochemistry. In embodiments, the level of PD-L1 (e.g., as assessed by immunohistochemistry) is given a value between 0% and 100%. In embodiments, the level of PD-L1 is compared to a negative control. In embodiments, the level of PD-L1 expression is measured by gene expression. In embodiments, the level of PD-L1 is given a z-score. In embodiments, detecting PD-L1 expression comprises use of the Fluidigm real-time PCR platform. In embodiments, the tumor sample is from a subject who is treatment naïve for A2A receptor antagonist therapy. In embodiments, the tumor sample is from a subject who has been administered an A2A receptor antagonist. In embodiments, to assess whether such a subject's tumor is likely to respond to a A2A receptor antagonist, a calculated PD-L1 expression score for the tumor sample is compared to a reference score for PD-L1 expression that has been pre-selected to divide at least the majority of responders to A2A receptor antagonist therapy from at least the majority of non-responders to A2A receptor antagonist therapy. In embodiments, if the subject has a PD-L1 expression score that is equal to or a greater than the reference PD-L1 expression score, the subject is more likely to respond, or to achieve a better response, to the A2A receptor antagonist than if the subject's PD-L1 expression score is less than the reference score. Non-limiting examples of methods for detecting an increase in the level of PD-L1 mRNA included qRT-PCR, microarray hybridization methods, and RNA sequencing (RNAseq). Non-limiting examples of methods for detecting an increase in the level of PD-L1 protein include High-performance liquid chromatography (HPLC), Liquid chromatography-mass spectrometry (LC/MS), Enzyme-linked immunosorbent assay (ELISA), immunoelectrophoresis, Western blot, radioimmuno assays, and protein immunostaining (e.g., immunohistochemistry).

In embodiments, cancer tumor or the blood (e.g., whole blood, plasma, and/or serum) of the subject comprises an elevated level of CD73 relative to a control. In embodiments, the level of CD73 (e.g., the absolute level of CD73) is measured in immune cells and/or tumor cells. In embodiments, the level of CD73 (e.g., the absolute level of CD73) is measured in immune cells and/or tumor cells is measured by immunohistochemistry. In embodiments, the cancer tumor comprises an elevated level of CD73 relative to a control. In embodiments, the control is a negative control. In embodiments, the elevated level is an increase of at least about 1%, 5%, 10%, 15%, 20%, 25%, 30%, 35%, 40%, 45%, 50%, 55%, 60%, 65%, 70%, 75%, 80%, 85%, 90%, 100%, 2-fold, 5-fold, 10-fold, 20-fold, or 100-fold compared to the control. In embodiments, the elevated level is an increase of at least about 5%-50%, 50%-100%, or 75-200% compared to the control. In embodiments, the elevated level is an increase of at least about 1% compared to the control. In embodiments, the elevated level is an increase of at least about 5% compared to the control. In embodiments, the elevated level is an increase of at least about 10% compared to the control. In embodiments, the elevated level is an increase of at least about 15% compared to the control. In embodiments, the elevated level is an increase of at least about 25% compared to the control. In embodiments, the elevated level is an increase of at least about 50% compared to the control. In embodiments, the elevated level is an increase of at least about 75% compared to the control. In embodiments, the elevated level is an increase of at least about 100% compared to the control. In embodiments, the elevated level is an increase of at least about 2-fold compared to the control. In embodiments, the elevated level is an increase of at least about 5-fold compared to the control. In embodiments, the elevated level is an increase of at least about 10-fold compared to the control. In embodiments, the cancer tumor comprises an elevated level of CD73 in tumor infiltrating lymphocytes relative to a control. In embodiments, the tumor infiltrating lymphocytes are CD8 T cells. In embodiments, the cancer tumor comprises an elevated level of CD73 in all tumor cells (e.g., in the tumor cell population taken as a whole) relative to a control. In embodiments, the increased level of CD73 is an increased level of CD73 mRNA (i.e., mRNA that encodes CD73). In embodiments, the increased level of CD73 is an increased level of CD73 protein. In embodiments, the level of CD73 is measured by immunohistochemistry. In embodiments, the level of CD73 (e.g., as assessed by immunohistochemistry) is given a value between 0% and 100%. In embodiments, the level of CD73 (e.g., as assessed by immunohistochemistry) is given an H-score value between 0 and 300. In embodiments, the level of CD73 (e.g., as assessed by immunohistochemistry) can be given separately for tumor cells and for the stromal compartment. In embodiments, the level of CD73 is compared to a negative control. In embodiments, the level of CD73 expression is measured by gene expression. In embodiments, the level of CD73 is given a z-score. In embodiments, detecting CD73 expression comprises use of the Fluidigm real-time PCR platform. In embodiments, the tumor sample is from a subject who is treatment naïve for A2A receptor antagonist therapy. In embodiments, the tumor sample is from a subject who has been administered an A2A receptor antagonist. In embodiments, to assess whether such a subject's tumor is likely to respond to a A2A receptor antagonist, a calculated CD73 expression score for the tumor sample is compared to a reference score for CD73 expression that has been pre-selected to divide at least the majority of responders to A2A receptor antagonist therapy from at least the majority of non-responders to A2A receptor antagonist therapy. In embodiments, if the subject has a CD73 expression score that is equal to or a greater than the reference CD73 expression score, the subject is more likely to respond, or to achieve a better response, to the A2A receptor antagonist than if the subject's CD73 expression score is less than the reference score. Non-limiting examples of methods for detecting an increase in the level of CD73 mRNA included qRT-PCR, microarray hybridization methods, and RNA sequencing (RNAseq). Non-limiting examples of methods for detecting an increase in the level of CD73 protein include High-performance liquid chromatography (HPLC), Liquid chromatography-mass spectrometry (LC/MS), Enzyme-linked immunosorbent assay (ELISA), immunoelectrophoresis, Western blot, radioimmuno assays, and protein immunostaining (e.g., immunohistochemistry).

An "adenosine-A2A receptor antagonist" or "A2A receptor antagonist" as provided herein refers to a substance capable of detectably lowering expression or activity level of an A2A receptor compared to a control. The inhibited expression or activity of the A2A receptor can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. In embodiments the adenosine-A2A receptor antagonist is a compound or small molecule that inhibits an A2A receptor e.g., by binding, partially or totally blocking stimulation, decrease, prevent, or delay activation, or inactivate, desensitize, or down-regulate signal transduction, gene expression or enzymatic activity necessary for A2A activity. A "small molecule" is an organic compound having a molecular weight of less than about 2000 daltons. In embodiments, a small molecule has a molecular weight of less than about 1500, 1000, 900, 800, 700, 600, or 500 daltons. In embodiments, the A2A receptor antagonist is a small molecule having a molecular weight of less than 1000 daltons. In embodiments, the A2A receptor antagonist is CPI-444. In embodiments, the programmed cell death protein 1 (PD-1) signaling pathway inhibitor is atezolizumab. In embodiments, the A2A receptor antagonist and the PD-1 signaling pathway inhibitor are administered simultaneously or sequentially. In embodiments, the A2A receptor antagonist and the PD-1 signaling pathway inhibitor are administered within 1 month of each other, within 1 week of each other, within 1 day of each other, or within 1 hour of each other. In embodiments, the dose of the A2A receptor antagonist in combination with the dose of the PD-1 signaling pathway inhibitor is less than would typically be effective to treat a responsive subject if the dose of the A2A receptor antagonist was administered alone. In embodiments, the dose of the PD-1 signaling pathway inhibitor in combination with the dose of the A2A receptor antagonist is less than would typically be effective to treat a responsive subject if the dose of the PD-1 signaling pathway inhibitor was administered alone. In embodiments, the doses of the PD-1 signaling pathway inhibitor and the A2A receptor antagonist are each less than would typically be effective to treat a responsive subject if either was administered alone.

A "PD-1 signaling pathway inhibitor" or a "PD-1 pathway inhibitor" as provided herein refers to a substance capable of detectably lowering expression of or activity level of the PD-1 signaling pathway compared to a control. The inhibited expression or activity of the PD-1 signaling pathway can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a compound or small molecule that inhibits the PD-1 signaling pathway e.g., by binding, partially or totally blocking stimulation of the PD-1 signaling pathway, decrease, prevent, or delay activation of the PD-1 signaling pathway, or inactivate, desensitize, or down-regulate signal transduction, gene expression or enzymatic activity of the PD-1 signaling pathway. In embodiments, the PD-1 signaling pathway inhibitor inhibits PD-1 activity or expression. In embodiments, the PD-1 signaling pathway inhibitor inhibits PD-L1 activity or expression. In embodiments, the PD-1 signaling pathway inhibitor is a compound or a small molecule. In embodiments, the PD-1 signaling pathway inhibitor is an antibody. Exemplary PD-1 pathway inhibitors include atezolizumab, avelumab, durvalumab, BMS-936559, pidilzumab, AMP-224, AMP-514, PDR001, nivolumab, pembrolizumab, ipilimumab, and cemiplimab.

The term "anti-PD-1 compound" refers to a compound that is a PD-1 signaling pathway inhibitor.

According to the methods provided herein, the subject is administered an effective amount of one or more of the agents (e.g., an A2A receptor antagonist and/or a PD-1 signaling pathway inhibitor) provided herein. An "effective amount" is an amount sufficient to accomplish a stated purpose (e.g. achieve the effect for which it is administered, treat a disease (e.g., cancer), reduce receptor signaling activity, reduce one or more symptoms of a disease or condition). An example of an "effective amount" is an amount sufficient to contribute to the treatment, prevention, or reduction of a symptom or symptoms of a disease (e.g., cancer), which could also be referred to as a "therapeutically effective amount." A "reduction" of a symptom or symptoms (and grammatical equivalents of this phrase) means decreasing of the severity or frequency of the symptom(s), or elimination of the symptom(s). Guidance can be found in the literature for appropriate dosages for given classes of pharmaceutical products. For example, for the given parameter, a therapeutically effective amount will show an increase or decrease of at least 5%, 10%, 15%, 20%, 25%, 40%, 50%, 60%, 75%, 80%, 90%, or at least 100%. In embodiments, this increase or decrease for a given parameter may vary throughout the day (e.g. a peak percentage increase or decrease may differ from a percentage increase or decrease when therapeutic concentrations in circulating blood are at their peak or trough concentrations dependent on daily dosing patterns and individual pharmacokinetics). Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

Thus, in one aspect, a method of treating cancer in a subject in need thereof is provided. The method includes administering to the subject a therapeutically effective amount of an adenosine-A2A receptor antagonist. In aspects, the methods of treating cancer comprise administering to the subject a therapeutically effective amount of an adenosine-A2A receptor antagonist and a PD-1 signaling pathway inhibitor. In aspects, the methods of treating cancer comprise administering to the subject a therapeutically effective amount of an adenosine-A2A receptor antagonist, a PD-1 signaling pathway inhibitor, and an anti-cancer agent. In aspects, the methods of treating cancer comprise administering to the subject a therapeutically effective amount of an adenosine-A2A receptor antagonist and an anti-cancer agent. In aspects, the methods of treating cancer comprise administering to the subject a therapeutically effective amount of a PD-1 signaling pathway inhibitor. In embodiments, the anti-cancer agent is not a PD-1 signaling pathway inhibitor.

In embodiments, the adenosine-A2A receptor antagonist is a compound of formula:

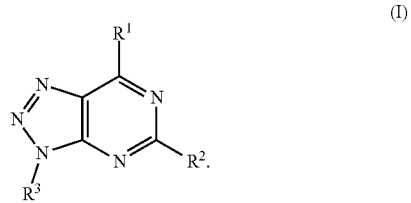

(I)

In formula (I), $R^1$ is independently hydrogen, halogen, $-CX^a_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^b_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^c_3$, $-CN$, $-SO_2Cl$, $-SO_{n3}R^{13}$, $-SO_{v3}NR^{13}R^{14}$, $-NHNH_2$, $-ONR^{13}R^{14}$, $-NHC=(O)NHNH_2$, $NHC=(O)NR^{13}R^{14}$, $-N(O)_{m3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, $=O$, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently —F, —Cl, —Br, or —I. The symbols $n_1$, $n_2$ and $n_3$ are independently an integer from 0 to 4. In embodiments, $n_1$ is 0. In embodiments, $n_1$ is 1. In embodiments, $n_1$ is 3. In embodiments, $n_1$ is 4. In embodiments, $n_2$ is 0. In embodiments, $n_2$ is 1. In embodiments, $n_2$ is 3. In embodiments, $n_2$ is 4. In embodiments, $n_3$ is 0. In embodiments, $n_3$ is 1. In embodiments, $n_3$ is 3. In embodiments, $n_3$ is 4. The symbols $m_1$, $m_2$ and $m_3$ are independently an integer from 1 to 2. In embodiments, $m_1$ is 0. In embodiments, $m_1$ is 1. In embodiments, $m_1$ is 2. In embodiments, $m_2$ is 0. In embodiments, $m_2$ is 1. In embodiments, $m_2$ is 2. In embodiments, $m_3$ is 0. In embodiments, $m_3$ is 1. In embodiments, $m_2$ is 2. The symbols $v_1$, $v_2$ and $v_3$ are independently an integer from 1 to 2. In embodiments, $v_1$ is 0. In embodiments, $v_1$ is 1. In embodiments, $v_1$ is 2. In embodiments, $v_2$ is 0. In embodiments, $v_2$ is 1. In embodiments, $v_2$ is 2. In embodiments, $v_3$ is 0. In embodiments, $v_3$ is 1. In embodiments, $v_3$ is 2.

In embodiments, $R^1$ is independently hydrogen, halogen, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, $R^{1A}$-substituted or unsubstituted alkyl, $R^{1A}$-substituted or unsubstituted heteroalkyl, $R^{1A}$-substituted or unsubstituted cycloalkyl, $R^{1A}$-substituted or unsubstituted heterocycloalkyl, $R^{1A}$-substituted or unsubstituted aryl, or $R^{1A}$-substituted or unsubstituted heteroaryl. $R^1$ may be $R^{1A}$-substituted or unsubstituted (e.g., $C_1$-$C_{20}$ or $C_1$-$C_6$) alkyl, $R^{1A}$-substituted or unsubstituted (e.g., 2 to 20 membered or 2 to 6 membered) heteroalkyl, $R^{1A}$-substituted or unsubstituted (e.g., $C_3$-$C_8$ or $C_5$-$C_7$) cycloalkyl, $R^{1A}$-substituted or unsubstituted (e.g., 3 to 8 membered or 3 to 6 membered) heterocycloalkyl, $R^{1A}$-substituted or unsubstituted (e.g., $C_5$-$C_{10}$ or $C_5$-$C_6$) aryl, or $R^{1A}$-substituted or unsubstituted (e.g., 5 to 10 membered or 5 to 6 membered) heteroaryl.

In embodiments, $R^{1A}$ is independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, $R^{1B}$-substituted or unsubstituted alkyl, $R^{1B}$-substituted or unsubstituted heteroalkyl, $R^{1B}$-substituted or unsubstituted cycloalkyl, $R^{1B}$-substituted or unsubstituted heterocycloalkyl, $R^{1B}$-substituted or unsubstituted aryl, or $R^{1B}$-substituted or unsubstituted heteroaryl. $R^{1A}$ may be $R^{1B}$-substituted or unsubstituted (e.g., $C_1$-$C_{20}$ or $C_1$-$C_6$) alkyl, $R^{1B}$-substituted or unsubstituted (e.g., 2 to 20 membered or 2 to 6 membered) heteroalkyl, $R^{1B}$-substituted or unsubstituted (e.g., $C_3$-$C_8$ or $C_5$-$C_7$) cycloalkyl, $R^{1B}$-substituted or unsubstituted (e.g., 3 to 8 membered or 3 to 6 membered) heterocycloalkyl, $R^{1B}$-substituted or unsubstituted (e.g., $C_5$-$C_{10}$ or $C_5$-$C_6$) aryl, or $R^{1B}$-substituted or unsubstituted (e.g., 5 to 10 membered or 5 to 6 membered) heteroaryl.

In embodiments, $R^{1B}$ is independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, $R^{1C}$-substituted or unsubstituted alkyl, $R^{1C}$-substituted or unsubstituted heteroalkyl, $R^{1C}$-substituted or unsubstituted cycloalkyl, $R^{1C}$-substituted or unsubstituted heterocycloalkyl, $R^{1C}$-substituted or unsubstituted aryl, or $R^{1C}$-substituted or unsubstituted heteroaryl. $R^{1B}$ may be $R^{1C}$-substituted or unsubstituted (e.g., $C_1$-$C_{20}$ or $C_1$-$C_6$) alkyl, $R^{1C}$-substituted or unsubstituted (e.g., 2 to 20 membered or 2 to 6 membered) heteroalkyl, $R^{1C}$-substituted or unsubstituted (e.g., $C_3$-$C_8$ or $C_5$-$C_7$) cycloalkyl, $R^{1C}$-substituted or unsubstituted (e.g., 3 to 8 membered or 3 to 6 membered) heterocycloalkyl, $R^{1C}$-substituted or unsubstituted (e.g., $C_5$-$C_{10}$ or $C_5$-$C_6$) aryl, or $R^{1C}$-substituted or unsubstituted (e.g., 5 to 10 membered or 5 to 6 membered) heteroaryl.

$R^{1C}$ is independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl. $R^{1C}$ may be independently unsubstituted (e.g., $C_1$-$C_{20}$ or C1-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^1$ is independently $R^{1A}$-substituted or unsubstituted alkyl, $R^{1A}$-substituted or unsubstituted heteroalkyl, $R^{1A}$-substituted or unsubstituted cycloalkyl, $R^{1A}$-substituted or unsubstituted heterocycloalkyl, $R^{1A}$-substituted or unsubstituted aryl, or s $R^{1A}$-substituted or unsubstituted heteroaryl. In embodiments, $R^1$ is $R^{1A}$-substituted or unsubstituted (e.g., 5 to 10 membered or 5 to 6 membered) heteroaryl. In embodiments, $R^1$ is unsubstituted 5 to 6 membered heteroaryl. In embodiments, $R^1$ is $R^{1A}$-substituted 5 to 6 membered heteroaryl. In embodiments, $R^1$ is unsubstituted 5 membered heteroaryl. In embodiments, $R^1$ is $R^{1A}$-substituted 5 membered heteroaryl. In embodiments, $R^1$ is $R^{1A}$-substituted furanyl.

In embodiments, $R^{1A}$ is $R^{1B}$-substituted or unsubstituted (e.g., $C_1$-$C_{20}$ or C1-$C_6$) alkyl. In embodiments, $R^{1A}$ is $R^{1B}$-substituted $C_1$-$C_6$ alkyl. In embodiments, $R^{1A}$ is unsubstituted $C_1$-$C_6$ alkyl. In embodiments, $R^{1A}$ is RIB-substituted $C_1$-$C_4$ alkyl. In embodiments, $R^{1A}$ is unsubstituted $C_1$-$C_4$ alkyl. In embodiments, $R^{1A}$ is RIB-substituted $C_1$-$C_3$ alkyl. In embodiments, $R^{1A}$ is unsubstituted $C_1$-$C_3$ alkyl. In embodiments, $R^{1A}$ is methyl.

In embodiments, $R^2$ is independently hydrogen, halogen, —CX$^b_3$, —CN, —SO$_2$Cl, —SO$_{n2}$R$^{11}$, —SO$_{v2}$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_{m2}$, —NR$^{11}$R$^{12}$, —NH—O—R$^{11}$, —C(O)R$^{11}$, —C(O)—OR$^{11}$, —C(O)NR$^{11}$R$^{12}$, or —OR$^{11}$. In embodiments of the methods provided herein, $R^2$ is independently hydrogen, halogen, —CF$_3$, —CN, —CCl$_3$, —COOH, —CH$_2$COOH, —CONH$_2$, —OH, —SH, —SO$_2$Cl, —SO$_3$H, —SO$_4$H, —SO$_2$NH$_2$, —NO$_2$, —NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^2$ is —NR$^{11}$R$^{12}$. In embodiments, $R^{11}$ and $R^{12}$ are independently hydrogen or substituted or unsubstituted (e.g., $C_1$-$C_{20}$ or $C_1$-$C_6$) alkyl. In embodiments, $R^{11}$ and $R^{12}$ are independently substituted or unsubstituted $C_1$-$C_6$ alkyl. In embodiments, $R^{11}$ and $R^{12}$ are independently substituted or unsubstituted $C_1$-$C_4$ alkyl. In embodiments, $R^{11}$ and $R^{12}$ are independently substituted or unsubstituted $C_1$-$C_3$ alkyl. In embodiments, $R^{11}$ and $R^{12}$ are independently unsubstituted $C_1$-$C_6$ alkyl. In embodiments, $R^{11}$ and $R^{12}$ are independently substituted or unsubstituted $C_1$-$C_4$ alkyl. In embodiments, $R^{11}$ and $R^{12}$ are independently unsubstituted $C_1$-$C_3$ alkyl. In embodiments, $R^{11}$ and $R^{12}$ are independently hydrogen.

In embodiments, $R^3$ is independently hydrogen, halogen, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^4$-substituted or unsubstituted alkyl, $R^4$-substituted or unsubstituted heteroalkyl, $R^4$-substituted or unsubstituted cycloalkyl, $R^4$-substituted or unsubstituted heterocycloalkyl, $R^4$-substituted or unsubstituted aryl, or $R^4$-substituted or unsubstituted heteroaryl. $R^3$ may be $R^4$-substituted or unsubstituted (e.g., $C_1$-$C_{20}$ or $C_1$-$C_6$) alkyl, $R^4$-substituted or unsubstituted (e.g., 2 to 20 membered or 2 to 6 membered) heteroalkyl, $R^4$-substituted or unsubstituted (e.g., $C_3$-$C_8$ or $C_5$-$C_7$) cycloalkyl, $R^4$-substituted or unsubstituted (e.g., 3 to 8 membered or 3 to 6 membered) heterocycloalkyl, $R^4$-substituted or unsubstituted (e.g., $C_5$-$C_{10}$ or $C_5$-$C_6$) aryl, or $R^4$-substituted or unsubstituted (e.g., 5 to 10 membered or 5 to 6 membered) heteroaryl.

$R^4$ is independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^5$-substituted or unsubstituted alkyl, $R^5$-substituted or unsubstituted heteroalkyl, $R^5$-substituted or unsubstituted cycloalkyl, $R^5$-substituted or unsubstituted heterocycloalkyl, $R^5$-substituted or unsubstituted aryl, or $R^5$-substituted or unsubstituted heteroaryl. $R^4$ may be $R^5$-substituted or unsubstituted (e.g., $C_1$-$C_{20}$ or $C_1$-$C_6$) alkyl, $R^5$-substituted or unsubstituted (e.g., 2 to 20 membered or 2 to 6 membered) heteroalkyl, $R^5$-substituted or unsubstituted (e.g., $C_3$-$C_8$ or $C_5$-$C_7$) cycloalkyl, $R^5$-substituted or unsubstituted (e.g., 3 to 8 membered or 3 to 6 membered) heterocycloalkyl, $R^5$-substituted or unsubstituted (e.g., $C_5$-$C_{10}$ or $C_5$-$C_6$) aryl, or $R^5$-substituted or unsubstituted (e.g., 5 to 10 membered or 5 to 6 membered) heteroaryl.

$R^5$ is independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^6$-substituted or unsubstituted alkyl, $R^6$-substituted or unsubstituted heteroalkyl, $R^6$-substituted or unsubstituted cycloalkyl, $R^6$-substituted or unsubstituted heterocycloalkyl, $R^6$-substituted or unsubstituted aryl, or $R^6$-substituted or unsubstituted heteroaryl. $R^5$ may be $R^6$-substituted or unsubstituted (e.g., $C_1$-$C_{20}$ or $C_1$-$C_6$) alkyl, $R^6$-substituted or unsubstituted (e.g., 2 to 20 membered or 2 to 6 membered) heteroalkyl, $R^6$-substituted or unsubstituted (e.g., $C_3$-$C_8$ or $C_5$-$C_7$) cycloalkyl, $R^6$-substituted or unsubstituted (e.g., 3 to 8 membered or 3 to 6 membered) heterocycloalkyl, $R^6$-substituted or unsubstituted (e.g., $C_5$-$C_{10}$ or $C_5$-$C_6$) aryl, or $R^6$-substituted or unsubstituted (e.g., 5 to 10 membered or 5 to 6 membered) heteroaryl.

$R^6$ is independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^7$-substituted or unsubstituted alkyl, $R^7$-substituted or unsubstituted heteroalkyl, $R^7$-substituted or unsubstituted cycloalkyl, $R^7$-substituted or unsubstituted heterocycloalkyl, $R^7$-substituted or unsubstituted aryl, or $R^7$-substituted or unsubstituted heteroaryl. $R^6$ may be $R^7$-substituted or unsubstituted (e.g., $C_1$-$C_{20}$ or $C_1$-$C_6$) alkyl, $R^7$-substituted or unsubstituted (e.g., 2 to 20 membered or 2 to 6 membered) heteroalkyl, $R^7$-substituted or unsubstituted (e.g., $C_3$-$C_8$ or $C_5$-$C_7$) cycloalkyl, $R^7$-substituted or unsubstituted (e.g., 3 to 8 membered or 3 to 6 membered) heterocycloalkyl, $R^7$-substituted or unsubstituted (e.g., $C_5$-$C_{10}$ or $C_5$-$C_6$) aryl, or $R^7$-substituted or unsubstituted (e.g., 5 to 10 membered or 5 to 6 membered) heteroaryl.

In embodiments, $R^3$ is independently hydrogen, halogen, $R^4$-substituted or unsubstituted alkyl, $R^4$-substituted or unsubstituted heteroalkyl, $R^4$-substituted or unsubstituted cycloalkyl, $R^4$-substituted or unsubstituted heterocycloalkyl, $R^4$-substituted or unsubstituted aryl, or $R^4$-substituted or unsubstituted heteroaryl. In embodiments, $R^3$ is independently $R^4$-substituted or unsubstituted (e.g., $C_1$-$C_{20}$ or $C_1$-$C_6$) alkyl. In embodiments, $R^3$ is independently $R^4$-substituted or unsubstituted $C_1$-$C_6$ alkyl. In embodiments, $R^3$ is independently $R^4$-substituted or unsubstituted $C_1$-$C_5$ alkyl. In embodiments, $R^3$ is independently $R^4$-substituted or unsubstituted $C_1$-$C_4$ alkyl. In embodiments, $R^3$ is independently $R^4$-substituted or unsubstituted $C_1$-$C_3$ alkyl. In embodiments, $R^3$ is independently unsubstituted $C_1$-$C_6$ alkyl. In embodiments, $R^3$ is independently unsubstituted $C_1$-$C_5$ alkyl. In embodiments, $R^3$ is independently $R^4$-unsubstituted $C_1$-$C_4$ alkyl. In embodiments, $R^3$ is independently unsubstituted $C_1$-$C_3$ alkyl. In embodiments, $R^3$ is independently $R^4$-substituted $C_1$-$C_6$ alkyl. In embodiments, $R^3$ is independently $R^4$-substituted $C_1$-$C_5$ alkyl. In embodiments, $R^3$ is independently $R^4$-substituted $C_1$-$C_4$ alkyl. In embodiments, $R^3$ is independently $R^4$-substituted $C_1$-$C_3$ alkyl. In embodiments, $R^3$ is $R^4$-substituted $C_1$ alkyl.

In embodiments, $R^4$ is $R^5$-substituted or unsubstituted (e.g., $C_1$-$C_{20}$ or $C_1$-$C_6$) alkyl, $R^5$-substituted or unsubstituted (e.g., 2 to 20 membered or 2 to 6 membered) heteroalkyl, $R^5$-substituted or unsubstituted (e.g., $C_3$-$C_8$ or $C_5$-$C_7$) cycloalkyl, $R^5$-substituted or unsubstituted (e.g., 3 to 8 membered or 3 to 6 membered) heterocycloalkyl, $R^5$-substituted or unsubstituted (e.g., $C_5$-$C_{10}$ or $C_5$-$C_6$) aryl, or $R^5$-substituted or unsubstituted (e.g., 5 to 10 membered or 5 to 6 membered) heteroaryl. In embodiments, $R^4$ is $R^5$-substituted or unsubstituted 5 to 6 membered heteroaryl. In embodiments, $R^4$ is $R^5$-substituted or unsubstituted 6 membered heteroaryl. In embodiments, $R^4$ is unsubstituted 6 membered heteroaryl. In embodiments, $R^4$ is $R^5$-substituted 6 membered heteroaryl. In embodiments, $R^4$ is $R^5$-substituted pyridinyl.

In embodiments, $R^5$ is $R^6$-substituted or unsubstituted (e.g., $C_1$-$C_{20}$ or $C_1$-$C_6$) alkyl, $R^6$-substituted or unsubstituted (e.g., 2 to 20 membered or 2 to 6 membered) heteroalkyl, $R^6$-substituted or unsubstituted (e.g., $C_3$-$C_8$ or $C_5$-$C_7$) cycloalkyl, $R^6$-substituted or unsubstituted (e.g., 3 to 8 membered or 3 to 6 membered) heterocycloalkyl, $R^6$-substituted or unsubstituted (e.g., $C_5$-$C_{10}$ or $C_5$-$C_6$) aryl, or $R^6$-substituted or unsubstituted (e.g., 5 to 10 membered or 5 to 6 membered) heteroaryl. In embodiments, $R^5$ is $R^6$-substituted or unsubstituted 2 to 6 membered heteroalkyl. In embodiments, $R^5$ is $R^6$-substituted or unsubstituted 2 to 5 membered heteroalkyl. In embodiments, $R^5$ is $R^6$-substituted or unsubstituted 2 to 4 membered heteroalkyl. In embodiments, $R^5$ is $R^6$-substituted or unsubstituted 2 to 3 membered heteroalkyl. In embodiments, $R^5$ is $R^6$-substituted or unsubstituted 2 membered heteroalkyl. In embodiments, $R^5$ is unsubstituted 2 to 6 membered heteroalkyl. In embodiments, $R^5$ is unsubstituted 2 to 5 membered heteroalkyl. In embodiments, $R^5$ is unsubstituted 2 to 4 membered heteroalkyl. In embodiments, $R^5$ unsubstituted 2 to 3 membered heteroalkyl. In embodiments, $R^5$ is unsubstituted 2 membered heteroalkyl. In embodiments, $R^5$ is $R^6$-substituted 2 to 6 membered heteroalkyl. In embodiments, $R^5$ is $R^6$-substituted 2 to 5 membered heteroalkyl. In embodiments, $R^5$ is $R^6$-substituted 2 to 4 membered heteroalkyl. In embodiments, $R^5$ is $R^6$-substituted 2 to 3 membered heteroalkyl. In embodiments, $R^5$ is $R^6$-substituted 2 membered heteroalkyl.

In embodiments, $R^6$ is $R^7$-substituted or unsubstituted (e.g., $C_1$-$C_{20}$ or $C_1$-$C_6$) alkyl, $R^7$-substituted or unsubstituted (e.g., 2 to 20 membered or 2 to 6 membered) heteroalkyl, $R^7$-substituted or unsubstituted (e.g., $C_3$-$C_8$ or $C_5$-$C_7$) cycloalkyl, $R^7$-substituted or unsubstituted (e.g., 3 to 8 membered or 3 to 6 membered) heterocycloalkyl, $R^7$-substituted or unsubstituted (e.g., $C_5$-$C_{10}$ or $C_5$-$C_6$) aryl, or $R^7$-substituted or unsubstituted (e.g., 5 to 10 membered or 5 to 6 membered) heteroaryl. In embodiments, $R^6$ is $R^7$-substituted or unsubstituted 3 to 6 membered heterocycloalkyl. In embodiments, $R^6$ is $R^7$-substituted or unsubstituted 5 membered heterocycloalkyl. In embodiments, $R^6$ is $R^7$-substituted 5 membered heterocycloalkyl. In embodiments, $R^6$ is unsubstituted 5 membered heterocycloalkyl. In embodiments, $R^6$ is unsubstituted tetrahydrofuranyl.

In embodiments of the methods provided herein, $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$ is $R^{1.4}$-substituted furanyl. In one further embodiment, $R^{1.4}$ is methyl. In another further embodiment, $R^2$ is —$NR^{11}R^{12}$. In another further embodiment, $R^{11}$ and $R^{12}$ are independently hydrogen. In yet another further embodiment, $R^3$ is $R^4$-substituted $C_1$ alkyl. In another further embodiment, $R^4$ is $R^5$-substituted pyridinyl. In yet another further embodiment, $R^5$ is $R^6$-substituted 2 membered heteroalkyl. In another further embodiments, $R^6$ is unsubstituted tetrahydrofuranyl.

In embodiments, the adenosine-A2A receptor antagonist is a compound of formula:

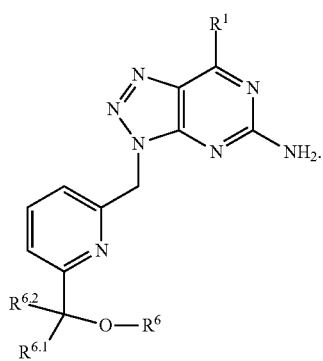

(II)

In formula (II), $R^6$, $R^{6.1}$ and $R^{6.2}$ are independently hydrogen, halogen, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$, $R^{6.1}$ and $R^{6.2}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{6.1}$ and $R^{6.2}$ are hydrogen and $R^6$ is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{6.1}$ and $R^{6.2}$ are hydrogen and $R^6$ is substituted or unsubstituted heterocycloalkyl. In embodiments, $R^{6.1}$ and $R^{6.2}$ are hydrogen and $R^6$ is unsubstituted heterocycloalkyl. In embodiments, $R^1$ is substituted (e.g. with an unsubstituted $C_1$-$C_5$ alkyl) or unsubstituted heteroaryl. In embodiments, $R^1$ is substituted (e.g. with an unsubstituted $C_1$-$C_5$ alkyl) or unsubstituted furanyl. In embodiments, $R^1$ is methyl-substituted furanyl.

In formula (II), $R^1$ and $R^6$ are as described above (e.g., $R^6$ may be $R^7$-substituted or unsubstituted 3 to 6 membered heterocycloalkyl and $R^1$ may be $R^{1.4}$-substituted 5 to 6 membered heteroaryl). Thus, in embodiments, $R^6$ is unsubstituted tetrahydrofuranyl and $R^1$ is $R^{1.4}$-substituted furanyl.

In formula (II), $R^{6.1}$ may be independently hydrogen, halogen, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{7.1}$-substituted or unsubstituted alkyl, $R^{7.1}$-substituted or unsubstituted heteroalkyl, $R^{7.1}$-substituted or unsubstituted cycloalkyl, $R^{7.1}$-substituted or unsubstituted heterocycloalkyl, $R^{7.1}$-substituted or unsubstituted aryl, or $R^{7.1}$-substituted or unsubstituted heteroaryl. $R^{6.1}$ may be $R^{7.1}$-substituted or unsubstituted (e.g., $C_1$-$C_{20}$ or $C_1$-$C_6$) alkyl, $R^{7.1}$-substituted or unsubstituted (e.g., 2 to 20 membered or 2 to 6 membered) heteroalkyl, $R^{7.1}$-substituted or unsubstituted (e.g., $C_3$-$C_8$ or $C_5$-$C_7$) cycloalkyl, $R^{7.1}$-substituted or unsubstituted (e.g., 3 to 8 membered or 3 to 6 membered) heterocycloalkyl, $R^{7.1}$-substituted or unsubstituted (e.g., $C_5$-$C_{10}$ or $C_5$-$C_6$) aryl, or $R^{7.1}$-substituted or unsubstituted (e.g., 5 to 10 membered or 5 to 6 membered) heteroaryl. In embodiments, $R^{6.1}$ is $R^{7.1}$-substituted or unsubstituted $C_1$-$C_6$ alkyl. In embodiments, $R^{6.1}$ is $R^{7.1}$-substituted or unsubstituted $C_1$-$C_5$ alkyl. In embodiments, $R^{6.1}$ is $R^{7.1}$-substituted or unsubstituted $C_1$-$C_4$ alkyl. In embodiments, $R^{6.1}$ is $R^{7.1}$-substituted or unsubstituted $C_1$-$C_3$ alkyl. In embodiments, $R^{6.1}$ is $R^{7.1}$-substituted $C_1$-$C_6$ alkyl. In embodiments, $R^{6.1}$ is $R^{7.1}$-substituted $C_1$-$C_5$ alkyl. In embodiments, $R^{6.1}$ is $R^{7.1}$-substituted $C_1$-$C_4$ alkyl. In embodiments, $R^{6.1}$ is $R^{7.1}$-substituted $C_1$-$C_3$ alkyl. In embodiments, $R^{6.1}$ is unsubstituted $C_1$-$C_6$ alkyl. In embodiments, $R^{6.1}$ is unsubstituted $C_1$-$C_5$ alkyl. In embodiments, $R^{6.1}$ is unsubstituted $C_1$-$C_4$ alkyl. In embodiments, $R^{6.1}$ is unsubstituted $C_1$-$C_3$ alkyl. In embodiments, $R^{6.1}$ is unsubstituted methyl.

$R^{6.2}$ is independently hydrogen, halogen, =O, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{7.2}$-substituted or unsubstituted alkyl, $R^{7.2}$-substituted or unsubstituted heteroalkyl, $R^{7.2}$-substituted or unsubstituted cycloalkyl, $R^{7.2}$-substituted or unsubstituted heterocycloalkyl, $R^{7.2}$-substituted or unsubstituted aryl, or $R^{7.2}$-substituted or unsubstituted heteroaryl. $R^{6.2}$ may be $R^{7.2}$-substituted or unsubstituted (e.g., $C_1$-$C_{20}$ or $C_1$-$C_6$) alkyl, $R^{7.2}$-substituted or unsubstituted (e.g., 2 to 20 membered or 2 to 6 membered) heteroalkyl, $R^{7.2}$-substituted or unsubstituted (e.g., $C_3$-$C_8$ or $C_5$-$C_7$) cycloalkyl, $R^{7.2}$-substituted or unsubstituted (e.g., 3 to 8 membered or 3 to 6 membered) heterocycloalkyl, $R^{7.2}$-substituted or unsubstituted (e.g., $C_5$-$C_{10}$ or $C_5$-$C_6$) aryl, or $R^{7.2}$-substituted or unsubstituted (e.g., 5 to 10 membered or 5 to 6 membered) heteroaryl. In embodiments, $R^{6.2}$ is $R^{7.2}$-substituted or unsubstituted $C_1$-$C_6$ alkyl. In embodiments, $R^{6.2}$ is $R^{7.2}$-substituted or unsubstituted $C_1$-$C_5$ alkyl. In embodiments, $R^{6.2}$ is $R^{7.2}$-substituted or unsubstituted $C_1$-$C_4$ alkyl. In embodiments, $R^{6.2}$ is $R^{7.2}$-substituted or unsubstituted $C_1$-$C_3$ alkyl. In embodiments, $R^{6.2}$ is $R^{7.2}$-substituted $C_1$-$C_6$ alkyl. In embodiments, $R^{6.2}$ is $R^{7.2}$-substituted $C_1$-$C_5$ alkyl. In embodiments, $R^{6.2}$ is $R^{7.2}$-substituted $C_1$-$C_4$ alkyl. In embodiments, $R^{6.2}$ is $R^{7.2}$-substituted $C_1$-$C_3$ alkyl. In embodiments, $R^{6.2}$ is unsubstituted $C_1$-$C_6$ alkyl. In embodiments, $R^{6.2}$ is unsubstituted $C_1$-$C_5$ alkyl. In embodiments, $R^{6.2}$ is unsubstituted $C_1$-$C_4$ alkyl. In embodiments, $R^{6.2}$ is unsubstituted $C_1$-$C_3$ alkyl. In embodiments, $R^{6.2}$ is unsubstituted methyl.

$R^7$, $R^{7.1}$ and $R^{7.2}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $R^7$, $R^{7.1}$ and $R^{7.2}$ may be independently unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., C3-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, the adenosine-A2A receptor antagonist is a compound of formula (III), also known as CPI-444:

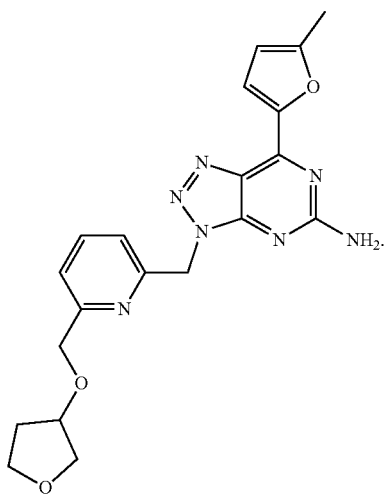 [SMILES: Cc1ccc(-c2nc(N)nc3c2nnn3Cc2cccc(COC3CCOC3)n2)o1]
(III)

In embodiments, the adenosine-A2A receptor antagonist is a compound of formula (IIIA):

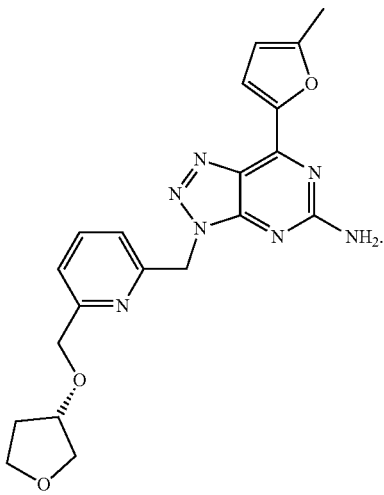 [SMILES: Cc1ccc(-c2nc(N)nc3c2nnn3Cc2cccc(COC3CCOC3)n2)o1]
(IIIA)

In embodiments, the adenosine-A2A receptor antagonist is a compound of formula (IIIB):

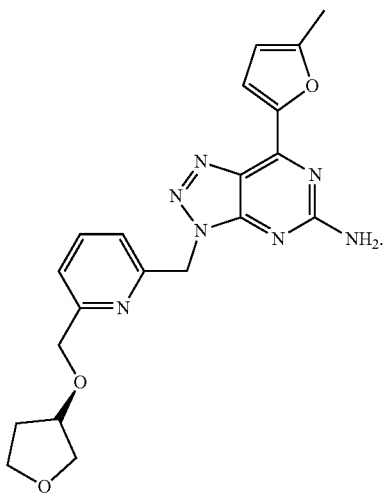
(IIIB)

In embodiments, the adenosine-A2A receptor antagonist is a mixture of the compounds of Formula (IIIA) and (IIIB). In embodiments, the adenosine-A2A receptor antagonist is a mixture of 1%-99% of the compound of Formula (IIIA) and 99%-1% of the compound of Formula (IIIB). In embodiments, the adenosine-A2A receptor antagonist is a mixture of 1%-50% of the compound of Formula (IIIA) and 99%-50% of the compound of Formula (IIIB). In embodiments, the adenosine-A2A receptor antagonist is a mixture of 99%-50% of the compound of Formula (IIIA) and 1%-50% of the compound of Formula (IIIB). In embodiments, the adenosine-A2A receptor antagonist is a mixture of 1%-25% of the compound of Formula (IIIA) and 99%-75% of the compound of Formula (IIIB). In embodiments, the adenosine-A2A receptor antagonist is a mixture of 99%-75% of the compound of Formula (IIIA) and 1%-25% of the compound of Formula (IIIB). In embodiments, the adenosine-A2A receptor antagonist is a racemic mixture of the compounds of Formula (IIIA) and (IIIB).

In embodiments, the adenosine-A2A receptor antagonists described herein, including the compounds of formula (I), formula (II), formula (III), formula (IIIA), and formula (IIIB) are in the form of a pharmaceutically acceptable salt. In embodiments, the adenosine-A2A receptor antagonists described herein, including the compounds of formula (I), formula (II), formula (III), formula (IIIA), and formula (IIIB) are in the free base form.

In embodiments, an adenosine receptor antagonists is administration in conjunction with an additional anti-cancer agent. In embodiments, an adenosine receptor antagonist is administered in conjunction with an antibody anti-cancer agent. In embodiments, an adenosine receptor antagonist is administered with a PD-L1 antagonist. In embodiments, an A2A receptor antagonist is administered in conjunction with an antibody against PD-L1. In embodiments, CPI-444 is administered in conjunction with atezolizumab.

In embodiments, the adenosine-A2A receptor antagonist and the PD-1 signaling pathway inhibitor are administered in a combined synergistic amount. A "combined synergistic amount" as used herein refers to the sum of a first amount (e.g., an amount of an adenosine-A2A receptor antagonist) and a second amount (e.g., an amount of a PD-1 signaling pathway inhibitor) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the adenosine-A2A receptor antagonist when used separately from the PD-1 signaling pathway inhibitor. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the PD-1 signaling pathway inhibitor when used separately from the adenosine-A2A receptor antagonist.

The synergistic effect may be an adenosine-A2A receptor activity decreasing effect and/or a PD-1 signaling pathway activity decreasing effect. In embodiments, synergy between the adenosine-A2A receptor antagonist and the PD-1 signaling pathway inhibitor may result in at least a 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater decrease (e.g., decrease of adenosine-A2A receptor activity or decrease of PD-1 signaling pathway activity) than the sum of the decrease of the adenosine-A2A receptor antagonist or the PD-1 signaling pathway when used individually and separately. In embodiments, synergy between the adenosine-A2A receptor antagonist and the PD-1 signaling pathway inhibitor may result in at least a 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater inhibition of the adenosine-A2A receptor and/or the PD-1 signaling pathway than the sum of the inhibition of the adenosine-A2A receptor antagonist or the PD-1 signaling pathway inhibitor when used individually and separately.

In embodiments, the synergistic effect may be a cancer-treating effect such as an lung cancer (i.e. a lung cancer-treating synergistic effect), bladder cancer (i.e. a bladder cancer-treating synergistic effect), melanoma (i.e. a melanoma-treating synergistic effect), renal cell carcinoma (i.e. a renal cell carcinoma-treating synergistic effect), colon cancer (i.e. a colon cancer-treating synergistic effect), ovarian cancer (i.e. an ovarian cancer-treating synergistic effect), gastric cancer (i.e. a gastric cancer-treating synergistic effect), breast cancer (i.e. a breast cancer-treating synergistic effect), head and neck carcinoma (i.e. a head and neck carcinoma-treating synergistic effect), prostate cancer (i.e. a prostate cancer-treating synergistic effect) and a hematologic malignancy (i.e. a hematologic malignancy-treating synergistic effect).

The adenosine-A2A receptor antagonist and the PD-1 signaling pathway inhibitor may be administered in combination either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of the adenosine-A2A receptor antagonist and the PD-1 signaling pathway inhibitor. In embodiments, where the adenosine-A2A receptor antagonist and the PD-1 signaling pathway inhibitor are administered sequentially, the A2A receptor antagonist is administered at a first time point and the PD-1 signaling pathway inhibitor is administered at a second time point, wherein the first time point precedes the second time point. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly). Thus, in embodiments, the adenosine-A2A receptor antagonist and the PD-1 signaling pathway inhibitor are administered simultaneously or sequentially.

In embodiments, the adenosine-A2A receptor antagonist is administered at a first time point and the PD-1 signaling pathway inhibitor is administered at a second time point, wherein the first time point precedes the second time point. In embodiments, the second time point is within less than about 120, 90, 60, 50, 40, 30, 20, 19, 18, 17, 16, 15, 14, 13, 12, 10, 11, 9, 8, 7, 6, 5, 4, 3, 2 or 1 days from the first time point. In embodiments, the second time point is within less than about 120 days from the first time point. In embodiments, the second time point is within less than about 90 days from the first time point. In embodiments, the second time point is within less than about 60 days from the first time point. In embodiments, the second time point is within less than about 50 days from the first time point. In embodiments, the second time point is within less than about 40 days from the first time point. In embodiments, the second time point is within less than about 30 days from the first time point. In embodiments, the second time point is within less than about 20 days from the first time point.

In embodiments, the second time point is within less than about 19 days from the first time point. In embodiments, the second time point is within less than about 18 days from the first time point. In embodiments, the second time point is within less than about 17 days from the first time point. In embodiments, the second time point is within less than about 16 days from the first time point. In embodiments, the second time point is within less than about 15 days from the first time point. In embodiments, the second time point is within less than about 14 days from the first time point. In embodiments, the second time point is within less than about 13 days from the first time point. In embodiments, the second time point is within less than about 12 days from the first time point. In embodiments, the second time point is within less than about 11 days from the first time point. In embodiments, the second time point is within less than about 10 days from the first time point. In embodiments, the second time point is within less than about 9 days from the first time point. In embodiments, the second time point is within less than about 8 days from the first time point. In embodiments, the second time point is within less than about 7 days from the first time point. In embodiments, the second time point is within less than about 6 days from the first time point. In embodiments, the second time point is within less than about 5 days from the first time point. In embodiments, the second time point is within less than about 4 days from the first time point. In embodiments, the second time point is within less than about 3 days from the first time point. In embodiments, the second time point is within less than about 2 days from the first time point. In embodiments, the second time point is within less than about 1 day from the first time point.

In embodiments, the second time point is within about 8, 10 or 12 days from the first time point. In embodiments, the second time point is within about 8, days from the first time point. In embodiments, the second time point is within about 10 days from the first time point. In embodiments, the second time point is within about 12 days from the first time point. In embodiments, the PD-1 signaling pathway inhibitor and the adenosine-A2A receptor antagonist are simultaneously administered at the second time point. In embodiments, the PD-1 signaling pathway inhibitor and the adenosine-A2A receptor antagonist are concomitantly administered at the second time point. In embodiments, the PD-1 signaling pathway inhibitor is administered at the second time point and the adenosine-A2A receptor antagonist is not administered at the second time point.

In embodiments, the PD-1 signaling pathway inhibitor is administered at a first time point and the adenosine-A2A receptor antagonist is administered at a second time point, wherein the first time point precedes the second time point. In embodiments, the second time point is within less than about 120, 90, 60, 50, 40, 30, 20, 19, 18, 17, 16, 15, 14, 13, 12, 10, 11, 9, 8, 7, 6, 5, 4, 3, 2 or 1 days from the first time point. In embodiments, the second time point is within less than about 120 days from the first time point. In embodiments, the second time point is within less than about 90 days from the first time point. In embodiments, the second time point is within less than about 60 days from the first time point. In embodiments, the second time point is within less than about 50 days from the first time point. In embodiments, the second time point is within less than about 40 days from the first time point. In embodiments, the second time point is within less than about 30 days from the first time point. In embodiments, the second time point is within less than about 20 days from the first time point.

In embodiments, the second time point is within less than about 19 days from the first time point. In embodiments, the second time point is within less than about 18 days from the first time point. In embodiments, the second time point is within less than about 17 days from the first time point. In embodiments, the second time point is within less than about 16 days from the first time point. In embodiments, the second time point is within less than about 15 days from the first time point. In embodiments, the second time point is within less than about 14 days from the first time point. In embodiments, the second time point is within less than about 13 days from the first time point. In embodiments, the second time point is within less than about 12 days from the first time point. In embodiments, the second time point is within less than about 11 days from the first time point. In embodiments, the second time point is within less than about 10 days from the first time point. In embodiments, the second time point is within less than about 9 days from the first time point. In embodiments, the second time point is within less than about 8 days from the first time point. In embodiments, the second time point is within less than about 7 days from the first time point. In embodiments, the second time point is within less than about 6 days from the first time point. In embodiments, the second time point is within less than about 5 days from the first time point. In embodiments, the second time point is within less than about 4 days from the first time point. In embodiments, the second time point is within less than about 3 days from the first time point. In embodiments, the second time point is within less than about 2 days from the first time point. In embodiments, the second time point is within less than about 1 day from the first time point.

In embodiments, the second time point is within about 8, 10 or 12 days from the first time point. In embodiments, the second time point is within about 8, days from the first time point. In embodiments, the second time point is within about 10 days from the first time point. In embodiments, the second time point is within about 12 days from the first time point. In embodiments, the PD-1 signaling pathway inhibitor and the adenosine-A2A receptor antagonist are simultaneously administered at the second time point. In embodiments, the PD-1 signaling pathway inhibitor and the adenosine-A2A receptor antagonist are concomitantly administered at the second time point. In embodiments, the adenosine-A2A receptor antagonist is administered at the second time point and the PD-1 signaling pathway inhibitor is not administered at the second time point.

In embodiments, the adenosine-A2A receptor antagonist is administered at an amount of about 0.5 mg, 1 mg, 2 mg, 3 mg, 4 mg, 5 mg, 10 mg, 20 mg, 30 mg, 40 mg, 50 mg, 60 mg, 70 mg, 80 mg, 90 mg, 100 mg, 200 mg, 300 mg, 1-50 mg, 1-200 mg, 1-100 mg, 50-100 mg, 50-150 mg, 100-200 mg, or 150-200 mg. In embodiments, the adenosine-A2A receptor antagonist is administered at an amount of about 0.5 mg/kg, 1 mg/kg, 2 mg/kg, 3 mg/kg, 4 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg, 300 mg/kg, 1-50 mg/kg, 1-200 mg/kg, 1-100 mg/kg, 50-100 mg/kg, 50-150 mg/kg, 100-200 mg/kg, or 150-200 mg/kg. In embodiments, the A2A receptor antagonist is administered at an amount of about 0.5 mg/kg. In embodiments, the A2A receptor antagonist is administered at an amount of about 1 mg/kg. In embodiments, the A2A receptor antagonist is administered at an amount of about 5 mg/kg. In embodiments, the A2A receptor antagonist is administered at an amount of about 10 mg/kg. In embodiments, the A2A receptor antagonist is administered at an amount of about 20 mg/kg. In embodiments, the A2A receptor antagonist is administered at an amount of about 30 mg/kg. In embodiments, the A2A receptor antagonist is administered at an amount of about 40 mg/kg. In embodiments, the A2A receptor antagonist is administered at an amount of about 50 mg/kg. In embodiments, the A2A receptor antagonist is administered at an amount of about 60 mg/kg. In embodiments, the A2A receptor antagonist is administered at an amount of about 70 mg/kg. In embodiments, the A2A receptor antagonist is administered at an amount of about 80 mg/kg. In embodiments, the A2A receptor antagonist is administered at an amount of about 90 mg/kg. In embodiments, the A2A receptor antagonist is administered at an amount of about 100 mg/kg. In embodiments, the A2A receptor antagonist is administered at an amount of about 200 mg/kg. In embodiments, the A2A receptor antagonist is administered at an amount of about 300 mg/kg. It is understood that where the amount is referred to as "mg/kg", the amount is milligram per kilogram body weight of the subject being administered with the A2A receptor antagonist.

In embodiments, the adenosine-A2A receptor antagonist is administered at an amount of about 0.5 mg/kg, 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg or 300 mg/kg. In embodiments, the A2A receptor antagonist is administered at an amount of about 1 mg/kg. In embodiments, the A2A receptor antagonist is administered at an amount of about 1 mg/kg to 2 mg/kg. In embodiments, the A2A receptor antagonist is administered at an amount of about 1 mg/kg to 3 mg/kg. In embodiments, the A2A receptor antagonist is administered at an amount of about 1 mg/kg to 4 mg/kg. In embodiments, the A2A receptor antagonist is administered at an amount of about 1 mg/kg to 5 mg/kg.

In embodiments, the adenosine-A2A receptor antagonist is administered at an amount of about 10 mg BID, 20 mg BID, 30 mg BID, 40 mg BID, 50 mg BID, 60 mg BID, 70 mg BID, 80 mg BID, 90 mg BID, 100 mg BID, 110 mg BID, 120 mg BID, 130 mg BID, 140 mg BID, 150 mg BID, 160 mg BID, 170 mg BID, 180 mg BID, 190 mg BID, 200 mg BID, 210 mg BID, 220 mg BID, 230 mg BID, 240 mg BID, 250 mg BID, 260 mg BID, 270 mg BID, 280 mg BID, 290 mg BID, or 300 mg BID. In embodiments, the A2A receptor antagonist is administered at an amount of about 10 mg BID. In embodiments, the A2A receptor antagonist is administered at an amount of about 20 mg BID. In embodiments, the A2A receptor antagonist is administered at an amount of about 30 mg BID. In embodiments, the A2A receptor antagonist is administered at an amount of about 40 mg BID. In embodiments, the A2A receptor antagonist is administered at an amount of about 50 mg BID. In embodiments, the A2A receptor antagonist is administered at an amount of about 60 mg BID. In embodiments, the A2A receptor antagonist is administered at an amount of about 70 mg BID. In embodiments, the A2A receptor antagonist is administered at an amount of about 80 mg BID. In embodiments, the A2A receptor antagonist is administered at an amount of about 90 mg BID. In embodiments, the A2A receptor antagonist is administered at an amount of about 100 mg BID. It is understood that where the amount is referred to as "BID" which stands for "bis in die", the amount is administered twice a day.

In embodiments, the adenosine-A2A receptor antagonist is administered at an amount of about 110 mg BID. In embodiments, the A2A receptor antagonist is administered at an amount of about 120 mg BID. In embodiments, the A2A receptor antagonist is administered at an amount of about 130 mg BID. In embodiments, the A2A receptor antagonist is administered at an amount of about 140 mg BID. In embodiments, the A2A receptor antagonist is administered at an amount of about 150 mg BID. In embodiments, the A2A receptor antagonist is administered at an amount of about 160 mg BID. In embodiments, the A2A receptor antagonist is administered at an amount of about 170 mg BID. In embodiments, the A2A receptor antagonist is administered at an amount of about 180 mg BID. In embodiments, the A2A receptor antagonist is administered at an amount of about 190 mg BID. In embodiments, the A2A receptor antagonist is administered at an amount of about 200 mg BID. It is understood that where the amount is referred to as "BID" which stands for "bis in die", the amount is administered twice a day.

In embodiments, the adenosine-A2A receptor antagonist is administered at an amount of about 210 mg BID. In embodiments, the A2A receptor antagonist is administered at an amount of about 220 mg BID. In embodiments, the A2A receptor antagonist is administered at an amount of about 230 mg BID. In embodiments, the A2A receptor antagonist is administered at an amount of about 240 mg BID. In embodiments, the A2A receptor antagonist is administered at an amount of about 250 mg BID. In embodiments, the A2A receptor antagonist is administered at an amount of about 260 mg BID. In embodiments, the A2A receptor antagonist is administered at an amount of about 270 mg BID. In embodiments, the A2A receptor antagonist is administered at an amount of about 280 mg BID. In embodiments, the A2A receptor antagonist is administered at an amount of about 290 mg BID. In embodiments, the A2A receptor antagonist is administered at an amount of about 300 mg BID. It is understood that where the amount is referred to as "BID" which stands for "bis in die", the amount is administered twice a day.

In embodiments, the adenosine-A2A receptor antagonist is administered at an amount of about 10 mg QD, 20 mg QD, 30 mg QD, 40 mg QD, 50 mg QD, 60 mg QD, 70 mg QD, 80 mg QD, 90 mg QD, 100 mg QD, 110 mg QD, 120 mg QD, 130 mg QD, 140 mg QD, 150 mg QD, 160 mg QD, 170 mg QD, 180 mg QD, 190 mg QD, 200 mg QD, 210 mg QD, 220 mg QD, 230 mg QD, 240 mg QD, 250 mg QD, 260 mg QD, 270 mg QD, 280 mg QD, 290 mg QD, or 300 mg QD. In embodiments, the A2A receptor antagonist is administered at an amount of about 10 mg QD. In embodiments, the A2A receptor antagonist is administered at an amount of about 20 mg QD. In embodiments, the A2A receptor antagonist is administered at an amount of about 30 mg QD. In embodiments, the A2A receptor antagonist is administered at an amount of about 40 mg QD. In embodiments, the A2A receptor antagonist is administered at an amount of about 50 mg QD. In embodiments, the A2A receptor antagonist is administered at an amount of about 60 mg QD. In embodiments, the A2A receptor antagonist is administered at an amount of about 70 mg QD. In embodiments, the A2A receptor antagonist is administered at an amount of about 80 mg QD. In embodiments, the A2A receptor antagonist is administered at an amount of about 90 mg QD. In embodiments, the A2A receptor antagonist is administered at an amount of about 100 mg QD. It is understood that where the amount is referred to as "QD" which stands for "quaque die", the amount is administered once a day.

In embodiments, the adenosine-A2A receptor antagonist is administered at an amount of about 110 mg QD. In embodiments, the A2A receptor antagonist is administered at an amount of about 120 mg QD. In embodiments, the A2A receptor antagonist is administered at an amount of about 130 mg QD. In embodiments, the A2A receptor antagonist is administered at an amount of about 140 mg QD. In embodiments, the A2A receptor antagonist is administered at an amount of about 150 mg QD. In embodiments, the A2A receptor antagonist is administered at an amount of about 160 mg QD. In embodiments, the A2A receptor antagonist is administered at an amount of about 170 mg QD. In embodiments, the A2A receptor antagonist is administered at an amount of about 180 mg QD. In embodiments, the A2A receptor antagonist is administered at an amount of about 190 mg QD. In embodiments, the A2A receptor antagonist is administered at an amount of about 200 mg QD. It is understood that where the amount is referred to as "QD" which stands for "quaque die", the amount is administered once a day.

In embodiments, the adenosine-A2A receptor antagonist is administered at an amount of about 210 mg QD. In embodiments, the A2A receptor antagonist is administered at an amount of about 220 mg QD. In embodiments, the A2A receptor antagonist is administered at an amount of about 230 mg QD. In embodiments, the A2A receptor antagonist is administered at an amount of about 240 mg QD. In embodiments, the A2A receptor antagonist is administered at an amount of about 250 mg QD. In embodiments, the A2A receptor antagonist is administered at an amount of about 260 mg QD. In embodiments, the A2A receptor antagonist is administered at an amount of about 270 mg QD. In embodiments, the A2A receptor antagonist is administered at an amount of about 280 mg QD. In embodiments, the A2A receptor antagonist is administered at an amount of about 290 mg QD. In embodiments, the A2A receptor antagonist is administered at an amount of about 300 mg QD. It is understood that where the amount is referred to as "QD" which stands for "quaque die", the amount is administered once a day.

The adenosine-A2A receptor antagonist may be administered at an amount as provided herein on 28 consecutive days. The A2A receptor antagonist may be administered at an amount as provided herein on 14 consecutive days. In embodiments, the A2A receptor antagonist is administered at 50 mg BID, 100 mg BID or 200 mg QD. In embodiments, the A2A receptor antagonist is administered at 50 mg BID. In embodiments, the A2A receptor antagonist is administered at 100 mg BID. In embodiments, the A2A receptor antagonist is administered at 200 mg QD. In embodiments, the A2A receptor antagonist is administered at 100 mg BID and the PD-1 signaling pathway inhibitor is administered at an amount of 840 mg. In further embodiments, the A2A receptor antagonist and the PD-1 signaling pathway inhibitor are administered simultaneously on 28 consecutive days. In other further embodiments, the A2A receptor antagonist and the PD-1 signaling pathway inhibitor are administered simultaneously on 14 consecutive days.

In embodiments, the PD-1 signaling pathway inhibitor is administered at an amount of less than about 1,300 mg. In embodiments, the PD-1 signaling pathway inhibitor is administered at an amount of less than about 1,200 mg. In embodiments, the PD-1 signaling pathway inhibitor is administered at an amount of less than about 1,100 mg. In embodiments, the PD-1 signaling pathway inhibitor is administered at an amount of less than about 1,000 mg. In embodiments, the PD-1 signaling pathway inhibitor is administered at an amount of less than about 900 mg. In embodiments, the PD-1 signaling pathway inhibitor is administered at an amount of less than about 800 mg. In embodiments, the PD-1 signaling pathway inhibitor is administered at an amount of less than about 700 mg. In embodiments, the PD-1 signaling pathway inhibitor is administered at an amount of less than about 600 mg. In embodiments, the PD-1 signaling pathway inhibitor is administered at an amount of less than about 500 mg. In embodiments, the PD-1 signaling pathway inhibitor is administered at an amount of less than about 400 mg. In embodiments, the PD-1 signaling pathway inhibitor is administered at an amount of less than about 300 mg. In embodiments, the PD-1 signaling pathway inhibitor is administered at an amount of less than about 200 mg. In embodiments, the PD-1 signaling pathway inhibitor is administered at an amount of less than about 100 mg. In embodiments, the PD-1 signaling pathway inhibitor is administered at an amount of about 100 mg, 200 mg, 300 mg, 400 mg, 500 mg, 600 mg, 700 mg, 800 mg, 900 mg, 1.00 mg, 1,100 mg, 1,200 mg, or 1,300 mg. It is understood that where the amount is referred to as "mg" that the amount is the total amount in milligram of PD-1 signaling pathway inhibitor administered to the subject.

In embodiments, the PD-1 signaling pathway inhibitor is administered at an amount of about 700 mg. In embodiments, the PD-1 signaling pathway inhibitor is administered at an amount of about 720 mg. In embodiments, the PD-1 signaling pathway inhibitor is administered at an amount of about 740 mg. In embodiments, the PD-1 signaling pathway inhibitor is administered at an amount of about 760 mg. In embodiments, the PD-1 signaling pathway inhibitor is administered at an amount of about 780 mg. In embodiments, the PD-1 signaling pathway inhibitor is administered at an amount of about 800 mg. In embodiments, the PD-1 signaling pathway inhibitor is administered at an amount of about 820 mg. In embodiments, the PD-1 signaling pathway inhibitor is administered at an amount of about 840 mg. In embodiments, the PD-1 signaling pathway inhibitor is administered at an amount of about 860 mg. In embodiments, the PD-1 signaling pathway inhibitor is administered at an amount of about 880 mg. In embodiments, the PD-1 signaling pathway inhibitor is administered at an amount of about 900 mg. It is understood that where the amount is referred to as "mg" that the amount is the total amount in milligram of PD-1 signaling pathway inhibitor administered to the subject.

The methods provided herein are, inter alia, useful for the treatment of cancer. In embodiments, the cancer is selected from lung cancer (such as non-small cell lung cancer), bladder cancer, melanoma, renal cell carcinoma, colon cancer, ovarian cancer, gastric cancer, breast cancer, head and neck carcinoma, prostate cancer and a hematologic malignancy. In embodiments, the cancer is lung cancer. In embodiments, the cancer is non-small cell lung cancer. In embodiments, the cancer is bladder cancer. In embodiments, the cancer is melanoma. In embodiments, the cancer is renal cell carcinoma. In embodiments, the cancer is colon cancer. In embodiments, the cancer is colorectal cancer. In embodiments, the cancer is ovarian cancer. In embodiments, the cancer is gastric cancer. In embodiments, the cancer is breast cancer. In embodiments, the cancer is triple negative breast cancer. In embodiments, the cancer is head and neck carcinoma. In embodiments, the cancer is prostate cancer. In embodiments, the cancer is a hematologic malignancy.

In an aspect, a method of treating a cancer tumor in a subject in need thereof is provided. The cancer tumor comprises an elevated level of tumor infiltrating lymphocytes relative to a control, the cancer tumor comprises and elevated T-effector signature relative to a control, the subject comprises increased T cell receptor diversity in the blood or cancer tumor relative to a control, the cancer tumor comprises an elevated level of PD-L1 (e.g., relative to a control), and/or the cancer tumor or the blood of the subject comprises an elevated level of CD73 relative to a control. In embodiments, the tumor infiltrating lymphocytes are CD8 T cells. In embodiments, the cancer tumor comprises an elevated level of a T cell gene signature relative to a control. The method includes administering to the subject a therapeutically effective amount of an adenosine-A2A receptor antagonist of formula:

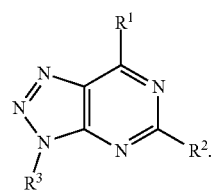
(I)

In formula (I), $R^1$ is independently hydrogen, halogen, $-CX^a_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^b_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^c_3$, $-CN$, $-SO_2Cl$, $-SO_{n3}R^{13}$, $-SO_{v3}NR^{13}R^{14}$, $-NHNH_2$, $-ONR^{13}R^{14}$, $-NHC=(O)NHNH_2$, $NHC=(O)NR^{13}R^{14}$, $-N(O)_{m3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently $-F$, $-Cl$, $-Br$, or $-I$. The symbols $n_1$, $n_2$ and $n_3$ are independently an integer from 0 to 4. In embodiments, $n_1$ is 0. In embodiments, $n_1$ is 1. In embodiments, $n_1$ is 3. In embodiments, $n_1$ is 4. In embodiments, $n_2$ is 0. In embodiments, $n_2$ is 1. In embodiments, $n_2$ is 3. In embodiments, $n_2$ is 4. In embodiments, $n_3$ is 0. In embodiments, $n_3$ is 1. In embodiments, $n_3$ is 3. In embodiments, $n_3$ is 4. The symbols $m_1$, $m_2$ and $m_3$ are independently an integer from 1 to 2. In embodiments, $m_1$ is 0. In embodiments, $m_1$ is 1. In embodiments, $m_1$ is 2. In embodiments, $m_2$ is 0. In embodiments, $m_2$ is 1. In embodiments, $m_2$ is 2. In embodiments, $m_3$ is 0. In embodiments, $m_3$ is 1. In embodiments, $m_3$ is 2. The symbols $v_1$, $v_2$ and $v_3$ are independently an integer from 1 to 2. In embodiments, $v_1$ is 0. In embodiments, $v_1$ is 1. In embodiments, $v_1$ is 2. In embodiments, $v_2$ is 0. In embodiments, $v_2$ is 1. In embodiments, $v_2$ is 2. In embodiments, $v_3$ is 0. In embodiments, $v_3$ is 1. In embodiments, $v_3$ is 2.

The A2A receptor antagonist provided herein is the same A2A receptor antagonist as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{1.4}$-substituted furanyl; $R^{1.4}$ is methyl; $R^2$ is $-NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl) and are incorporated herewith.

Thus, in embodiments, the adenosine-A2A receptor antagonist is a compound of formula:

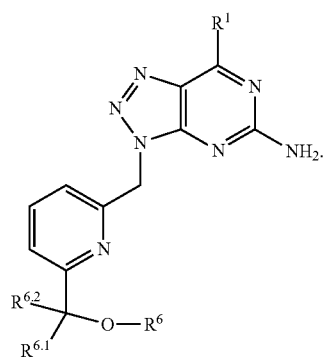

(II)

In formula (II), $R^6$, $R^{6.1}$ and $R^{6.2}$ are independently hydrogen, halogen, =O, =S, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the adenosine-A2A receptor antagonist is a compound of formula (III):

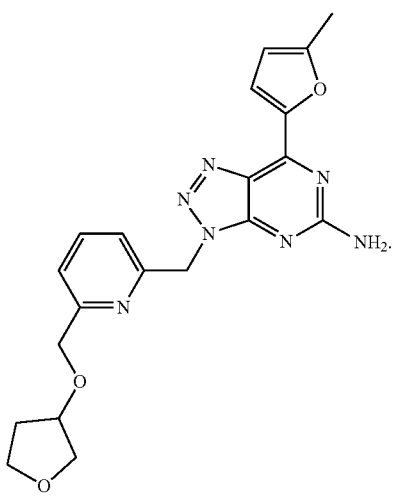

(III)

In embodiments, the adenosine-A2A receptor antagonist is a compound of formula (IIIA):

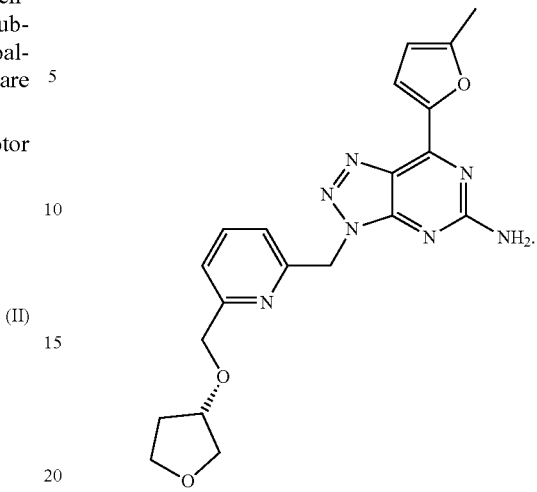

(IIIA)

In embodiments, the adenosine-A2A receptor antagonist is a compound of formula (IIIB):

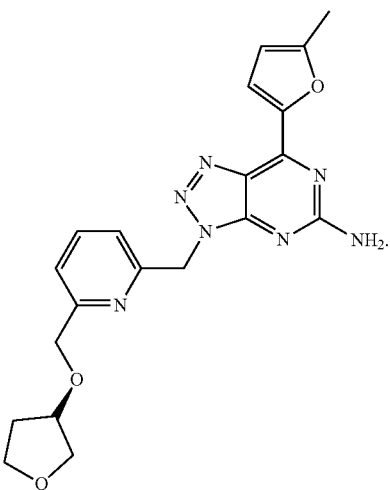

(IIIB)

In embodiments, the method further includes administering a therapeutically effective amount of a PD-1 signaling pathway inhibitor. In embodiments, the adenosine-A2A receptor antagonist and the PD-1 signaling pathway inhibitor are administered in a combined synergistic amount. In embodiments, the A2A receptor antagonist and the PD-1 signaling pathway inhibitor are administered simultaneously or sequentially. In embodiments, the A2A receptor antagonist is administered at a first time point and the PD-1 signaling pathway inhibitor is administered at a second time point, wherein the first time point precedes the second time point. In embodiments, the second time point is within less than about 120, 90, 60, 50, 40, 30, 20, 19, 18, 17, 16, 15, 14, 13, 12, 10, 11, 9, 8, 7, 6, 5, 4, 3, 2, or 1 days from the first time point. In embodiments, the second time point is within about 8, 10 or 12 days from the first time point. In embodiments, the PD-1 signaling pathway inhibitor is administered at a first time point and the A2A receptor antagonist is administered at a second time point, wherein the first time point precedes the second time point. In embodiments, the second time point is within less than about 120, 90, 60, 50, 40, 30, 20, 19, 18, 17, 16, 15, 14, 13, 12, 10, 11, 9, 8, 7, 6, 5, 4, 3, 2, or 1 days from the first time point. In embodiments, the second time point is within about 8, 10 or 12 days from the first time point.

In embodiments, the adenosine-A2A receptor antagonist is administered at an amount of about 0.5 mg/kg, 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg or 300 mg/kg. In embodiments, the A2A receptor antagonist is administered at an amount of about 1 mg/kg. In embodiments, the PD-1 signaling pathway inhibitor is administered at an amount of less than about 1,300 mg. In embodiments, the PD-1 signaling pathway inhibitor is administered at an amount of less than about 1,200 mg. In embodiments, the cancer is selected from lung cancer, bladder cancer, melanoma, renal cell carcinoma, colon cancer, ovarian cancer, gastric cancer, breast cancer, head and neck carcinoma, prostate cancer and a hematologic malignancy.

Methods of Activating T Cells

In an aspect, a method of activating a T cell is provided. In embodiments, the T cell is in a subject. In embodiments, the subject comprises an elevated level of tumor infiltrating lymphocytes (TILs) (e.g., within the cancer tumor) relative to a control, increased T cell receptor diversity in the blood or cancer tumor relative to a control, the cancer tumor comprises an elevated level of PD-L1 relative to a control, and/or the cancer tumor or the blood of the subject comprises an elevated level of CD73 relative to a control. In embodiments, the subject comprises an elevated level of a T cell gene signature (e.g., in the cancer tumor) relative to a control. In embodiments, the tumor infiltrating lymphocytes are CD8 T cells. The method includes contacting the T cell with an adenosine-A2A receptor antagonist, wherein the adenosine-A2A receptor antagonist is a compound of formula:

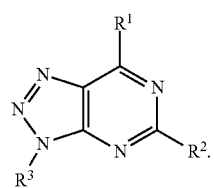

(I)

In formula (I), $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —$N(O)_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently —F, —Cl, —Br, or —I. $n_1$, $n_2$ and $n_3$ are independently an integer from 0 to 4. $m_1$, $m_2$ and $m_3$ are independently an integer from 1 to 2. And $v_1$, $v_2$ and $v_3$ are independently an integer from 1 to 2.

The A2A receptor antagonist provided herein is the same A2A receptor antagonist as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{1.4}$-substituted furanyl; $R^{1.4}$ is methyl; $R^2$ is —$NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl) and are incorporated herewith.

Thus, in embodiments, the adenosine-A2A receptor antagonist is a compound of formula:

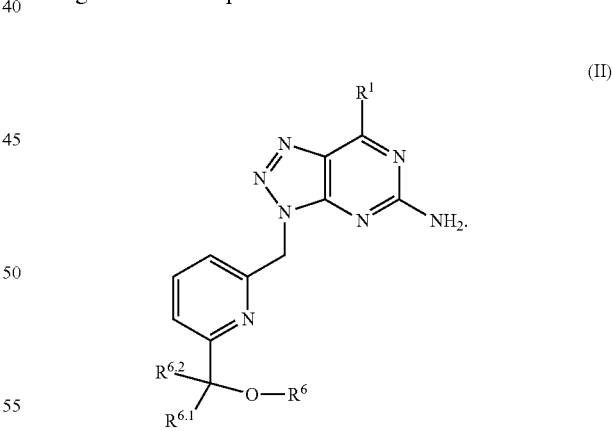

(II)

In formula (II), $R^6$, $R^{6.1}$ and $R^{6.2}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the adenosine-A2A receptor antagonist is a compound of formula (III):

(III)

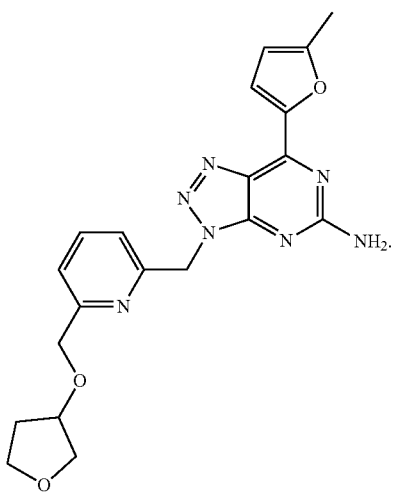

In embodiments, the adenosine-A2A receptor antagonist is a compound of formula (IIIA):

(IIIA)

In embodiments, the adenosine-A2A receptor antagonist is a compound of formula (IIIB):

(IIIB)

In embodiments, the method includes contacting the T cell with a PD-1 signaling pathway inhibitor. In embodiments, the PD-1 signaling pathway inhibitor is an antibody or a small molecule. In embodiments, the T cell is an effector T cell or a natural killer cell. In embodiments, the T cell is an adenosine-suppressed T cell. "An adenosine-suppressed T cell" is an effector T cell or a natural killer cell bound to adenosine through its A2A receptor, wherein the adenosine is bound in an amount sufficient to inhibit expression and/or secretion of immune response activating cytokines (e.g., expression of IL-2, IFN-γ or TNF). In embodiments, the T cell is a CD8 T cell. In embodiments, the CD8 T cell is a CD45RA-negative CD8 T cell. In embodiments, the T cell is a CD4 T cell. In embodiments, the CD4 T cell is a CD45RA-negative CD4 T cell. In embodiments, the T cell is within a subject. In embodiments, the subject is a cancer subject. In embodiments, the cancer subject is an anti-PD-1 refractory subject.

Pharmaceutical Compositions

Aspects relate to the administration of pharmaceutical compositions including an adenosine-A2A receptor antagonist and a pharmaceutically acceptable excipient. In embodiments, a pharmaceutical composition further comprises a PD-1 signaling pathway inhibitor. The provided compositions are, inter alia, suitable for formulation and administration in vitro or in vivo. Non-limiting examples of suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient.

Pharmaceutical compositions provided by the present invention include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the compounds and antibodies described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

Provided compositions can include a single agent or more than one agent. The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., the compounds and antibodies provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

In one aspect, a pharmaceutical composition including an A2A receptor antagonist, a PD-1 signaling pathway inhibitor and a pharmaceutically acceptable excipient is provided.

In embodiments, the adenosine-A2A receptor antagonist is a compound of formula:

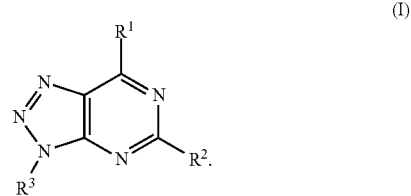

(I)

In formula (I), $R^1$ is independently hydrogen, halogen, $-CX^a{}_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$,
$-NHC=(O)NR^9R^{10}$, $-N(O)_{m1}$, $-NR^9R^{10}$,
$-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen,
halogen, $-CX^b{}_3$, $-CN$, $-SO_2Cl$, $-SO_{n2}R^{11}$,
$-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$,
$-NH-O-R^{11}$, $-C(O)R^{11}$, $-C(O)-OR^{11}$, $-C(O)NR^{11}R^{12}$, $-OR^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen,
halogen, $-CX^c{}_3$, $-CN$, $-SO_2Cl$, $-SO_{n3}R^{13}$,
$-SO_{v3}NR^{13}R^{14}$, $-NHNH_2$, $-ONR^{13}R^{14}$, $-NHC=(O)NHNH_2$, $-NHC=(O)NR^{13}R^{14}$, $-N(O)_{m3}$, $-NR^{13}R^{14}$,
$-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$ and $R^{14}$ are independently hydrogen, halogen, $=O$,
$=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^a$, $X^b$ and $X^c$ are independently $-F$, $-Cl$, $-Br$, or $-I$. $n_1$, $n_2$ and $n_3$ are independently an integer from 0 to 4. $m_1$, $m_2$ and $m_3$ are independently an integer from 1 to 2. And $v_1$, $v_2$ and $v_3$ are independently an integer from 1 to 2.

The A2A receptor antagonist and the PD-1 signaling pathway inhibitor provided herein are the same as described above for aspects of treating cancer using an A2A receptor antagonist and a PD-1 signaling pathway inhibitor. Therefore, the definitions for substituents and variables of formula (I) and (II) are the same as described above (e.g., $R^1$ is $R^{1.A}$-substituted furanyl; $R^{1.A}$ is methyl; $R^2$ is $-NR^{11}R^{12}$; $R^{11}$ and $R^{12}$ are independently hydrogen; $R^3$ is $R^4$-substituted $C_1$ alkyl; $R^4$ is $R^5$-substituted pyridinyl; $R^5$ is $R^6$-substituted 2 membered heteroalkyl; $R^6$ is unsubstituted tetrahydrofuranyl) and are incorporated herewith.

In embodiments, the adenosine-A2A receptor antagonist is a compound of formula:

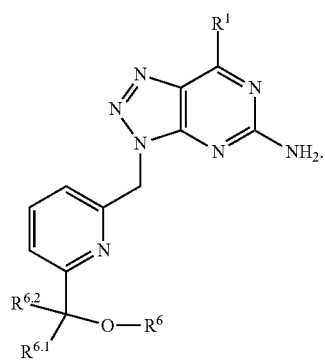

(II)

In formula (II), $R^6$, $R^{6.1}$ and $R^{6.2}$ are independently hydrogen, halogen, =O, =S, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the adenosine-A2A receptor antagonist is a compound of formula

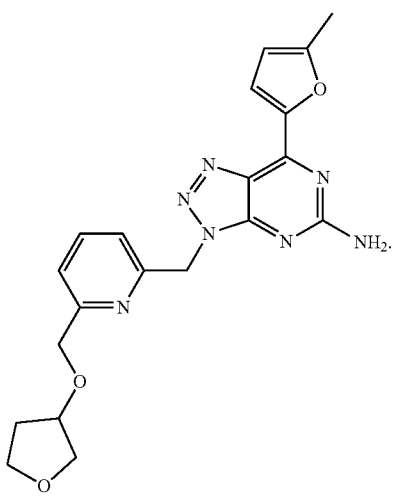

(III)

In embodiments, the adenosine-A2A receptor antagonist is a compound of formula (IIIA):

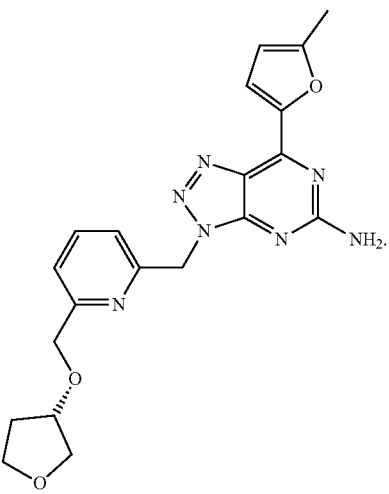

(IIIA)

In embodiments, the adenosine-A2A receptor antagonist is a compound of formula (IIIB):

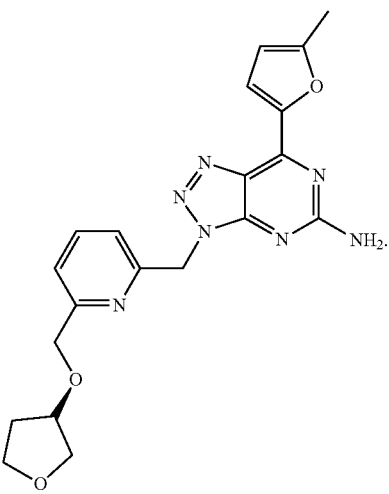

(IIIB)

In embodiments, the PD-1 signaling pathway inhibitor is a programmed death-ligand 1 (PD-L1) antagonist or a PD-1 antagonist. In embodiments, the programmed death-ligand 1 (PD-L1) antagonist is an antibody or a small molecule. In embodiments, the PD-L1 antagonist is an antibody. In embodiments, the antibody is atezolizumab. In embodiments, the PD-1 antagonist is an antibody or a small molecule. In embodiments, the A2A receptor antagonist and the PD-1 signaling pathway inhibitor are present in a combined synergistic amount, wherein the combined synergistic amount is effective to treat cancer in a subject in need thereof.

In embodiments, the pharmaceutical composition is in oral dosage form. In embodiments, the adenosine-A2A receptor antagonist (e.g., CPI-444) is presented as size 0-elongated hydroxypropyl methylcellulose (HPMC) capsules containing adenosine-A2A receptor antagonist compound (e.g., CPI-444) at 10 mg, 25 mg or 100 mg, as a dry powder mixture of adenosine-A2A receptor antagonist compound (e.g, CPI-444) resinate with common excipients and packaged in high density polyethylene (HDPE) bottles fitted with a polypropylene tamper evident child-resistant cap with an integrated desiccant. The adenosine-A2A receptor antagonist (e.g, CPI-444) resinate is a complex of the adenosine-A2A receptor antagonist and a cation exchange resin (Amberlite IRP69™). The ingredients are listed in Table A.

TABLE A

CPI-444 Capsules Table of Ingredients

| Ingredient | Function |
| --- | --- |
| CPI-444 (adenosine-A2A receptor antagonist) | Active ingredient |
| Sodium polystyrene sulfonate (Amberlite IRP69) resin | Ion-exchange resin, release modifying agent |
| Mannitol, spray-dried | Diluent |
| Croscarmellose sodium | Disintegrant |
| Colloidal silicon dioxide | Glidant |
| Sodium stearylfumarate | Lubricant |
| Size 0-elongated HPMC capsule | Capsule shell: 10 mg - opaque, Swedish orange 25 mg - opaque white 100 mg - opaque, Swedish orange |

Non-Limiting Examples of Detection, Assay, and Diagnostic Methods

In embodiments, a method described herein may include detecting a level of, e.g., PD-L1, CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, or CD44, or any combination thereof, e.g., with a binding agent (e.g., a specific binding agent that binds to a protein or nucleic acid molecule). Exemplary examples of a binding agent include an antibody or a fragment thereof, a detectable protein or a fragment thereof, a nucleic acid molecule such as an oligonucleotide/polynucleotide comprising a sequence that is complementary to patient genomic DNA, mRNA or a cDNA produced from patient mRNA, or any combination thereof. In embodiments, an antibody is labeled with detectable moiety, e.g., a fluorescent compound, an enzyme or functional fragment thereof, or a radioactive agent. In embodiments, an antibody is detectably labeled by coupling it to a chemiluminescent compound. In embodiments, the presence of the chemiluminescent-tagged antibody is then determined by detecting the presence of luminescence that arises during the course of chemical reaction. Non-limiting examples of particularly useful chemiluminescent labeling compounds are luminol, isoluminol, theromatic acridinium ester, imidazole, acridinium salt and oxalate ester.

In embodiments, a specific binding agent is an agent that has greater than 10-fold, preferably greater than 100-fold, and most preferably, greater than 1000-fold affinity for the target molecule as compared to another molecule. As the skilled artisan will appreciate the term specific is used to indicate that other biomolecules present in the sample do not significantly bind to the binding agent specific for the target molecule. In embodiments, the level of binding to a biomolecule other than the target molecule results in a binding affinity which is at most only 10% or less, only 5% or less only 2% or less or only 1% or less of the affinity to the target molecule, respectively. A preferred specific binding agent will fulfill both the above minimum criteria for affinity as well as for specificity. For example, in embodiments an antibody has a binding affinity (e.g., Kd) in the low micromolar ($10^{-6}$), nanomolar ($10^{-7}$-$10^{-9}$), with high affinity antibodies in the low nanomolar ($10^{-9}$) or pico molar ($10^{-12}$) range for its specific target ligand.

In embodiments, the present subject matter provides a composition comprising a binding agent, wherein the binding agent is attached to a solid support, (e.g., a strip, a polymer, a bead, a nanoparticle, a plate such as a multiwell plate, or an array such as a microarray). In embodiments relating to the use of a nucleic acid probe attached to a solid support (such as a microarray), a nucleic acid in a test sample may be amplified (e.g., using PCR) before or after the nucleic acid to be measured is hybridized with the probe. In embodiments, reverse transcription polymerase chain reaction (RT-PCR) is used to detect mRNA levels. In embodiments, a probe on a solid support is used, and mRNA (or a portion thereof) in a biological sample is converted to cDNA or partial cDNA and then the cDNA or partial cDNA is hybridized to a probe (e.g., on a microarray), hybridized to a probe and then amplified, or amplified and then hybridized to a probe. In embodiments, a strip may be a nucleic acid-probe coated porous or non-porous solid support strip comprising linking a nucleic acid probe to a carrier to prepare a conjugate and immobilizing the conjugate on a porous solid support. In embodiments, the support or carrier comprises glass, polystyrene, polypropylene, polyethylene, dextran, nylon, amylases, natural and modified celluloses, polyacrylamides, gabbros, and magnetite. In embodiments, the nature of the carrier can be either soluble to some extent or insoluble for the purposes of the present subject matter. In embodiments, the support material may have any structural configuration so long as the coupled molecule is capable of binding to a binding agent (e.g., an antibody). In embodiments, the support configuration may be spherical, as in a bead, or cylindrical, as in the inside surface of a test tube, or the external surface of a rod. In embodiments, the surface may be flat such as a plate (or a well within a multiwell plate), sheet, or test strip, etc. polystyrene beads. Those skilled in the art will know many other suitable carriers for binding antibody or antigen, or will be able to ascertain the same by use of routine experimentation.

In embodiments, a solid support comprises a polymer, to which an agent is chemically bound, immobilized, dispersed, or associated. In embodiments, a polymer support may be, e.g., a network of polymers, and may be prepared in bead form (e.g., by suspension polymerization). In embodiments, the location of active sites introduced into a polymer support depends on the type of polymer support. In embodiments, in a swollen-gel-bead polymer support the active sites are distributed uniformly throughout the beads, whereas in a macroporous-bead polymer support they are predominantly on the internal surfaces of the macropores. In embodiments, the solid support, e.g., a device, may contain an PD-L1 binding agent alone or together with a binding agent for at least one, two, three or more other molecules, e.g., CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, and/or CD44.

In embodiments, detection comprises an immunoassay. In embodiments, detectons comprises immunoprecipitation followed by mass spectrometry. In embodiments, detection is accomplished using an ELISA or Western blot format. In embodiments, the binding agent comprises an nucleic acid (e.g., a probe or primers that are complementary for mRNA or cDNA), and the detecting step is accomplished using a polymerase chain reaction (PCR) or Northern blot format, or other means of detection. In embodiments, a probe or primer is about 10-20, 15-25, 15-35, 15-25, 20-80, 50-100, or 10-100 nucleotides in length, e.g., about 10, 12, 15, 20, 25, 30, 35, 40, 45, 50, 55, 60, 70, 80, 90, or 100 nucleotides in length or less than about 30, 35, 40, 45, 50, 55, 60, 70, 80, 90, or 100 nucleotides in length.

As used herein, "assaying" means using an analytic procedure to qualitatively assess or quantitatively measure the presence or amount or the functional activity of a target entity. For example, assaying the level of a compound (such as a protein or an mRNA molecule) means using an analytic procedure (such as an in vitro procedure) to qualitatively assess or quantitatively measure the presence or amount of the compound.

In embodiments, a cell or sample containing cells (such as a biopsy, blood, or cells such as PBMCs obtained from blood) is lysed to release a protein or nucleic acid. Numerous methods for lysing cells and assessing protein and nucleic acid levels are known in the art. In embodiments, cells are physically lysed, such as by mechanical disruption, liquid homogenization, high frequency sound waves, freeze/thaw cycles, with a detergent, or manual grinding. Non-limiting examples of detergents include Tween 20, Triton X-100, and Sodium Dodecyl Sulfate (SDS). Non-limiting examples of assays for determining the level of a protein include HPLC, LC/MS, ELISA, immunoelectrophoresis, Western blot, immunohistochemistry, and radioimmuno assays. Non-limiting examples of assays for determining the level of an mRNA include Northern blotting, RT-PCR, RNA sequencing, and qRT-PCR.

In embodiments, a biological sample obtained for the purpose of evaluation in vitro. With regard to the methods disclosed herein, the sample or patient sample preferably may comprise any body fluid. In embodiments, the bodily fluid includes, but is not limited to, blood, plasma, serum, or lymph. In embodiments, the sample comprises blood or a fraction thereof (e.g., plasma, serum, fraction obtained via leukopheresis). In embodiments, the sample comprises white blood cells obtained from the subject. In embodiments, the sample comprises only white blood cells. In embodiments, the sample comprises PBMCs. In embodiments, the sample comprises T cells. In embodiments, the sample is a biopsy from a tumor (i.e., a solid tumor). In embodiments the biopsy is a core needle biopsy.

In embodiments, T-effector gene signature biomarkers described herein are useful to identify cancer patients who are most likely to achieve a clinical benefit from treatment with an A2A receptor antagonist. This utility supports the use of these biomarkers in a variety of research and commercial applications, including but not limited to, clinical trials of A2A receptor antagonists in which patients are selected on the basis of their T-effector gene signature score, diagnostic methods and products for determining a patient's T-effector gene signature score or for classifying a patient as positive or negative for a T-effector gene signature biomarker, personalized treatment methods which involve tailoring a patient's drug therapy based on the patient's T-effector gene signature score, as well as pharmaceutical compositions and drug products comprising an A2A receptor antagonist for use in treating patients who test positive for a T-effector signature biomarker.

The utility of any of diagnostic methods, kits, and compositions provided herein does not require that 100% of the patients who test positive for a biomarker of the invention achieve an anti-tumor response to an A2A receptor antagonist; nor does it require a diagnostic method or kit to have a specific degree of specificity or sensitivity in determining the presence or absence of a biomarker in every subject, nor does it require that a diagnostic method claimed herein be 100% accurate in predicting for every subject whether the subject is likely to have a beneficial response to an A2A receptor antagonist. With respect to diagnostics, the terms "determine", "determining" and "predicting" should not be interpreted as requiring a definite or certain result; instead these terms should be construed as meaning either that a claimed method provides an accurate result for at least the majority of subjects or that the result or prediction for any given subject is more likely to be correct than incorrect.

In embodiments, the accuracy of the result provided by a diagnostic method provided herein is one that a skilled artisan or regulatory authority would consider suitable for the particular application in which the method is used.

In embodiments, an T-effector gene signature score is determined in a sample of tumor tissue removed from a subject. In embodiments, the tumor is primary or recurrent, and may be of any type (as described above), any stage (e.g., Stage I, II, III, or IV or an equivalent of other staging system), and/or histology. The subject may be of any age, gender, treatment history and/or extent and duration of remission.

In embodiments, the tumor sample can be obtained by a variety of procedures including, but not limited to, surgical excision, aspiration or biopsy. In embodiments, the tissue sample may be sectioned and assayed as a fresh specimen; alternatively, the tissue sample may be frozen for further sectioning. In embodiments, the tissue sample is preserved by fixing and embedding in paraffin or the like.

In embodiments, the tumor tissue sample is fixed by conventional methodology, with the length of fixation depending on the size of the tissue sample and the fixative used. Neutral buffered formalin, glutaraldehyde, Bouin's and paraformaldehyde are nonlimiting examples of fixatives. In embodiments, the tissue sample is fixed with formalin. In embodiments, the fixed tissue sample is also embedded in paraffin to prepare an FFPE tissue sample.

In embodiments, the tissue sample is fixed and dehydrated through an ascending series of alcohols, infiltrated and embedded with paraffin or other sectioning media so that the tissue sample may be sectioned. In embodiments, the tumor tissue sample is first sectioned and then the individual sections are fixed.

In embodiments, the T-effector gene signature score for a tumor is determined using FFPE tissue sections of about 3-4 millimeters, and preferably 4 micrometers, which are mounted and dried on a microscope slide, and where tumor area is macrodissected (e.g., from multiple slides) for RNA extraction.

In embodiments, once a suitable sample of tumor tissue has been obtained, it is analyzed to quantitate the expression level of each of the genes that comprise the particular T-effector gene signature to be scored, e.g. 2 or more or each of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, and CD44. In embodiments, determining the expression level of a gene comprises detecting and quantifying RNA transcribed from that gene or a protein translated from such RNA. In embodiments, the RNA includes mRNA transcribed from the gene, and/or specific spliced variants thereof and/or fragments of such mRNA and spliced variants.

A person skilled in the art will appreciate that a number of methods can be used to isolate RNA from the tissue sample for analysis. For example, RNA may be isolated from frozen tissue samples by homogenization in guanidinium isothiocyanate and acid phenol-chloroform extraction. Commercial kits are available for isolating RNA from FFPE samples. In embodiments, the tumor sample is an FFPE tissue section on a glass slide and gene expression analysis is performed on whole cell lysates rather than on isolated total RNA.

Persons skilled in the art are also aware of several methods useful for detecting and quantifying the level of RNA transcripts within the isolated RNA or whole cell lysates. Quantitative detection methods include, but are not limited to, arrays (i.e., microarrays), quantitative real time PCR, multiplex assays, nuclease protection assays, and Northern blot analyses. Generally, such methods employ labeled probes that are complimentary to a portion of each transcript to be detected. Probes for use in these methods can be readily designed based on the known sequences of the genes and the transcripts expressed thereby. In embodiments, the probes are designed to hybridize to each of the gene signature transcripts. Suitable labels for the probes are well-known and include, e.g., fluorescent, chemiluminescent and radioactive labels.

In embodiments, assaying a tumor sample for a gene signature of the invention employs detection and quantification of RNA levels in real-time using nucleic acid sequence based amplification (NASBA) combined with molecular beacon detection molecules. NASBA is described, e.g., in Compton J., Nature 350 (6313):91-92 (1991). NASBA is a single-step isothermal RNA-specific amplification method. In embodiments, the method involves the following steps: RNA template is provided to a reaction mixture, where the first primer attaches to its complementary site at the 3' end of the template; reverse transcriptase synthesizes the opposite, complementary DNA strand; RNAse H destroys the RNA template (RNAse H only destroys RNA in RNA-DNA hybrids, but not single-stranded RNA); the second primer attaches to the 3' end of the DNA strand, and reverse transcriptase synthesizes the second strand of DNA; and T7 RNA polymerase binds double-stranded DNA and produces a complementary RNA strand which can be used again in step 1, such that the reaction is cyclic.

In embodiments, the assay format is a flap endonuclease-based format, such as the Invader™ assay (Third Wave Technologies). In the case of using the invader method, an invader probe containing a sequence specific to the region 3' to a target site, and a primary probe containing a sequence specific to the region 5' to the target site of a template and an unrelated flap sequence, are prepared. Cleavase is then allowed to act in the presence of these probes, the target molecule, as well as a FRET probe containing a sequence complementary to the flap sequence and an auto-complementary sequence that is labeled with both a fluorescent dye and a quencher. When the primary probe hybridizes with the template, the 3' end of the invader probe penetrates the target site, and this structure is cleaved by the Cleavase resulting in dissociation of the flap. The flap binds to the FRET probe and the fluorescent dye portion is cleaved by the Cleavase resulting in emission of fluorescence.

In embodiments, the assay format employs direct mRNA capture with branched DNA (QuantiGene™, Panomics) or Hybrid Capture™ (Digene).

One non-limiting example of an array technology suitable for use in measuring expression of the genes in an T-effector gene signature is the ArrayPlate™ assay technology sold by HTG Molecular, Tucson Ariz., and described in Martel, R. R., et al., Assay and Drug Development Technologies 1(1): 61-71, 2002. In brief, this technology combines a nuclease protection assay with array detection. Cells in microplate wells are subjected to a nuclease protection assay. Cells are lysed in the presence of probes that bind targeted mRNA species. Upon addition of S1 nuclease, excess probes and unhybridized mRNA are degraded, so that only mRNA:probe duplexes remain. Alkaline hydrolysis destroys the mRNA component of the duplexes, leaving probes intact. After the addition of a neutralization solution, the contents of the processed cell culture plate are transferred to another ArrayPlate™ called a programmed ArrayPlate™. ArrayPlates™ contain a 16-element array at the bottom of each well. Each array element comprises a position-specific anchor oligonucleotide that remains the same from one assay to the next. The binding specificity of each of the 16 anchors is modified with an oligonucleotide, called a programming linker oligonucleotide, which is complementary at one end to an anchor and at the other end to a nuclease protection probe. During a hybridization reaction, probes transferred from the culture plate are captured by immobilized programming linker. Captured probes are labeled by hybridization with a detection linker oligonucleotide, which is in turn labeled with a detection conjugate that incorporates peroxidase. The enzyme is supplied with a chemiluminescent substrate, and the enzyme-produced light is captured in a digital image. Light intensity at an array element is a measure of the amount of corresponding target mRNA present in the original cells.

By way of further non-limiting example, DNA microanalysis can be used to measure gene expression. In brief, a DNA microarray, also referred to as a DNA chip, is a microscopic array of DNA fragments, such as synthetic oligonucleotides, disposed in a defined pattern on a solid support, wherein they are amenable to analysis by standard hybridization methods (see Schena, BioEssays 18:427 (1996)). Exemplary microarrays and methods for their manufacture and use are set forth in T. R. Hughes et al., Nature Biotechnology 9:342-347 (2001). A number of different microarray configurations and methods for their production are known to those of skill in the art and are disclosed in U.S. Pat. Nos. 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770,456; 5,770,722; 5,837,832; 5,856,101; 5,874,219; 5,885,837; 5,919,523; 6,022,963; 6,077,674; and 6,156,501; Shena, et al., Tibtech 6:301-306, 1998; Duggan, et al., Nat. Genet. 2:10-14, 1999; Bowtell, et al., Nat. Genet. 21:25-32, 1999; Lipshutz, et al., Nat. Genet. 21:20-24, 1999; Blanchard, et al., Biosensors and Bioelectronics 77:687-90, 1996; Maskos, et al., Nucleic Acids Res. 2:4663-69, 1993; and Hughes, et al., Nat. Biotechnol. 79:342-347, 2001. Patents describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; the disclosures of which are herein incorporated by reference.

In embodiments, an array of oligonucleotides may be synthesized on a solid support. Exemplary solid supports include glass, plastics, polymers, metals, metalloids, ceramics, organics, etc. Using chip masking technologies and photoprotective chemistry, it is possible to generate ordered arrays of nucleic acid probes. These arrays, which are known, for example, as "DNA chips" or very large scale immobilized polymer arrays ("VLSIPS®" arrays), may include millions of defined probe regions on a substrate having an area of about 1 cm2 to several cm2, thereby incorporating from a few to millions of probes (see, e.g., U.S. Pat. No. 5,631,734).

In embodiments, to compare expression levels, labeled nucleic acids may be contacted with the array under conditions sufficient for binding between the target nucleic acid and the probe on the array. In embodiments, the hybridization conditions may be selected to provide for the desired level of hybridization specificity; that is, conditions sufficient for hybridization to occur between the labeled nucleic acids and probes on the microarray.

In embodiments, hybridization may be carried out in conditions permitting essentially specific hybridization. The length and GC content of the nucleic acid will determine the thermal melting point and thus, the hybridization conditions necessary for obtaining specific hybridization of the probe to the target nucleic acid. These factors are well known to a person of skill in the art, and may also be tested in assays. An extensive guide to nucleic acid hybridization may be found in Tijssen, et al. (Laboratory Techniques in Biochemistry and Molecular Biology, Vol. 24: Hybridization With Nucleic Acid Probes, P. Tijssen, ed.; Elsevier, N.Y. (1993)). The methods described above will result in the production of hybridization patterns of labeled target nucleic acids on the array surface. The resultant hybridization patterns of labeled nucleic acids may be visualized or detected in a variety of ways, with the particular manner of detection selected based on the particular label of the target nucleic acid. Representative detection means include scintillation counting, autoradiography, fluorescence measurement, calorimetric measurement, light emission measurement, light scattering, and the like.

One such (non-limiting) method of detection utilizes an array scanner that is commercially available (Affymetrix, Santa Clara, Calif.), for example, the 417® Arrayer, the 418® Array Scanner, or the Agilent Gene Array® Scanner. This scanner is controlled from a system computer with an interface and easy-to-use software tools. The output may be directly imported into or directly read by a variety of software applications. Exemplary scanning devices are described in, for example, U.S. Pat. Nos. 5,143,854 and 5,424,186.

In embodiments, an assay method to measure biomarker transcript abundance includes using the nCounter® Analysis System marketed by NanoString® Technologies (Seattle, Wash. USA). This system, which is described by Geiss et al., Nature Biotechnol. 2(3):317-325 (2008), utilizes a pair of probes, namely, a capture probe and a reporter probe, each comprising a 35- to 50-base sequence complementary to the transcript to be detected. The capture probe additionally includes a short common sequence coupled to an immobilization tag, e.g. an affinity tag that allows the complex to be immobilized for data collection. The reporter probe additionally includes a detectable signal or label, e.g. is coupled to a color-coded tag. Following hybridization, excess probes are removed from the sample, and hybridized probe/target complexes are aligned and immobilized via the affinity or other tag in a cartridge. The samples are then analyzed, for example using a digital analyzer or other processor adapted for this purpose. Generally, the color-coded tag on each transcript is counted and tabulated for each target transcript to yield the expression level of each transcript in the sample. This system allows measuring the expression of hundreds of unique gene transcripts in a single multiplex assay using capture and reporter probes designed by Nano String.

In embodiments, when measuring expression of the genes in a T-effector gene signature described herein, the absolute expression of each of the genes in a tumor sample is compared to a control; for example, the control can be the average level of expression of each of the genes, respectively, in a pool of subjects. In embodiments, to increase the sensitivity of the comparison, the expression level values may be transformed in a number of ways. For example, the expression level of each gene in the gene signature can be normalized by the average expression level of all of the genes, the expression level of which is determined, or by the average expression level of a set of control genes. Thus, in an embodiment, the genes are represented by a set of probes, and the expression level of each of the genes is normalized by the mean or median expression level across all of the genes represented, including any genes that are not part of the gene signature of interest. In a specific embodiment, the normalization is carried out by dividing the median or mean level of expression of all of the genes on the microarray. In an embodiment, the expression levels of the signature genes are normalized by the mean or median level of expression of a set of control genes. In an embodiment, the control genes comprise housekeeping genes. In an embodiment, the normalization is accomplished by dividing by the median or mean expression level of the control genes.

In embodiments, the sensitivity of a gene signature score will also be increased if the expression levels of individual genes in the gene signature are compared to the expression of the same genes in a pool of tumor samples. In embodiments, the comparison is to the mean or median expression level of each signature gene in the pool of samples. Such a comparison may be accomplished, for example, by dividing by the mean or median expression level of the pool for each of the genes from the expression level each of the genes in the subject sample of interest. In embodiments, this has the effect of accentuating the relative differences in expression between genes in the sample and genes in the pool as a whole, making comparisons more sensitive and more likely to produce meaningful results than the use of absolute expression levels alone. In embodiments, the expression level data may be transformed in any convenient way; preferably, the expression level data for all is log transformed before means or medians are taken.

In embodiments, the expression levels of the signature genes in the sample are compared to the expression level of those genes in the pool, where nucleic acid derived from the sample and nucleic acid derived from the pool are hybridized during the course of a single experiment. In embodiments, such an approach requires that a new pool of nucleic acid be generated for each comparison or limited numbers of comparisons, and is therefore limited by the amount of nucleic acid available. In embodiments, the expression levels in a pool, whether normalized and/or transformed or not, are stored on a computer, or on computer-readable media, to be used in comparisons to the individual expression level data from the sample (i.e., single-channel data).

In embodiments, when comparing a subject's tumor sample with a standard or control, the expression value of a particular gene in the sample is compared to the expression value of that gene in the standard or control. In embodiments, for each gene in a gene signature, the log(10) ratio is created for the expression value in the individual sample relative to the standard or control. In embodiments, a score for an T-effector gene signature is calculated by determining the mean log(10) ratio of the genes in the signature. In embodiments, if the gene signature score for the test sample is above a pre-determined threshold for that gene signature, then the sample is considered to be positive for a T-effector gene signature biomarker. In embodiments, the pre-determined threshold may also be the mean, median, or a percentile of scores for that gene signature in a collection of samples or a pooled sample used as a standard or control. It will be recognized by those skilled in the art that other differential expression values, besides log(10) ratio, may be used for calculating a signature score, as long as the value represents an objective measurement of transcript abundance of the genes. Examples include, but are not limited to: xdev, error-weighted log (ratio), and mean subtracted log (intensity).

In embodiments, raw expression values are normalized by performing quantile normalization relative to the reference distribution and subsequent log 10-transformation. In embodiments, when the gene expression is detected using the nCounter® Analysis System marketed by NanoString® Technologies, the reference distribution is generated by pooling reported (i.e., raw) counts for the test sample and one or more control samples (preferably at least 2 samples, more preferably at least any of 4, 8 or 16 samples) after excluding values for technical (both positive and negative control) probes and without performing intermediate normalization relying on negative (background-adjusted) or positive (synthetic sequences spiked with known titrations). In embodiments, the T-effector signature score is then calculated as the arithmetic mean of normalized values for each of the genes in the gene signature, e.g., each of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, and CD44.

In embodiments, the reference distribution is generated from raw expression counts for a normalization set of genes, which comprises, consists essentially of, or consists of each of the genes in the set of 400 genes listed below, or a subset thereof. In embodiments, the subset may consist of at least any of 1, 2, 3, 4, 5, 6, 7, 8, 9, 10, 11, 12, 13, 14, 15, 16, 17, 18, 19, 20, 21, 22, 23, 24, 25, 50, 75, 100, 125, 150, 175, 200, 225, 250, 275, 300, 325, 350, 375 or any whole number in between 1 and 400 or 25 and 400. In embodiments, the normalization set of genes does not include a gene that is in the T-effector signature. In embodiments, the normalization set of genes does not include any one of or lacks any combination of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, IL7R, CD44, CD73, and PD-L1. A non-limiting normalization gene set (any of which or any combination of which may be selected or omitted) is as follows (Gene IDs are followed by target transcript NCBI Accession Number): ABCF1 NM_001090.2; ALAS1 NM_000688.4; AXL NM_021913.2; Adipoq NM_004797.2; Areg NM_001657.2; Arg1 NM_000045.2; Arg2 NM_001172.3; Atp6v0d2 NM_152565.1; Atp8b4 NM_024837.2; B7-H3 (CD276) NM_001024736.1; B7-H4 (VTCN1) NM_024626.2; BAGE NM_001187.1; BCL6 NM_138931.1; BLNK NM_013314.2; Batf NM_006399.3; Bcl11a NM_022893.3; Bcl11b NM_022898.1; Bst1 NM_004334.2; Btla NM_181780.2; CADM1 NM_014333.3; CD112 NM_002856.2; CD113 NM_015480.2; CD127 (IL-7RA) NM_002185.2; CD14 NM_000591.2; CD155 NM_006505.3; CD160 NM_007053.2; CD163 NM_004244.4; CD167 DDR1 NM_001954.4; CD2 NM_001767.2; CD200 NM_005944.5; CD200R1 NM_138939.2; CD207-CLEC4K NM_015717.2; Langerin CD209 NM_021155.2; CD22 (Siglec-2) NM_001771.2; CD226 NM_006566.2; CD244 NM_016382.2; CD24a NM_013230.2; CD28 NM_001243078.1; CD3 delta NM_000732.4; CD3 epsilon NM_000733.2; CD3 zeta (CD247) NM_198053.1; CD300a NM_007261.2; CD300b (CD300LB NM_174892.2; IREM3) CD300e (IREM2) NM_181449.1; CD300f (IREM1) NM_139018.3; CD317 (Bst2) NM_004335.2; CD33 NM_001177608.1; CD4 NM_000616.3; CD40 (TNFRSF5) NM_001250.4; CD40L (TNFSF5) NM_000074.2; CD44 NM_001001392.1; CD45 (PTPRC) NM_080921.2; CD47 NM_001777.3; CD48 NM_001778.2; CD5 NM_014207.2; CD55 NM_000574.3; CD62L L-NR_029467.1; selectin Sell CD68 (SCARD1) NM_001251.2; CD69 NM_001781.1; CD7 NM_006137.6; CD72 NM_001782.2; CD79A NM_001783.3; CD80 NM_005191.3; CD84 NM_001184879.1; CD86 NM_175862.3; CD8b NM_172099.2; CD90 (Thy1) NM_006288.2; CD96 NM_005816.4; CDH1 (E Cadherin) NM_004360.2; CLEC12A NM_138337.5; CLEC15a (KLRG1 NM_005810.3; MAFA) CLEC4A NM_194448.2; CLEC6A NM_001007033.1; CSPG4 NM_001897.4; CXCL11-ITAC NM_005409.3; CXCL2 (GRO-NM_002089.3; beta MIP-2) CXCL9-Mig NM_002416.1; CXCR2 NM_001557.2; Caspase 3 NM_032991.2; Ccl19 NM_006274.2; Ccl21 NM_002989.2; Ccl24 NM_002991.2; Ccl27 NM_006664.2; Ccl3 NM_002983.2; Ccl4 NM_002984.2; Ccl5 NM_002985.2; Ccl8 NM_005623.2; Ccr2 NM_001123041.2; Ccr3 NM_001837.2; Ccr4 NM_005508.4; Ccr5 NM_000579.1; Ccr6 NM_031409.2; Ccr7 NM_001838.2; Cdo1 NM_001801.2; Chi3l1 NM_001276.2; Chi3l2 NM_004000.2; Ciita NM_000246.3; Clca1 NM_001285.3; Clca2 NM_006536.5; Clec10a (mouse NM_182906.2; also MGL1) Clec1b (Clec-2) NM_016509.3; Clec2d (OCIL) NM_001004419.3; Clec3b NM_003278.2; Clec4d (MCL) NM_080387.4; Clec4e (Mincle) NM_014358.2; Clec5a (MDL-1) NM_013252.2; Clec7a (dectin-1) NM_197954.2; Clec9a NM_207345.2; Cmklr1 NM_004072.1; Cpd NM_001304.4; Crtam NM_019604.2; Csf1r NM_005211.2; Csf2rb NM_000395.2; Cst6 NM_001323.3; Cst7 NM_003650.3; Ctla4 NM_005214.3; Ctsb NM_000100.2; Ctsg NM_001911.2; Ctsz NM_001336.3; Cx3cl1 NM_002996.3; Cx3cr1 NM_001337.3; Cxcl1 (GRO-alpha) NM_001511.1; Cxcl10 (IP-10) NM_001565.1; Cxcl13 (BCA-1) NM_006419.2; Cxcl14 NM_004887.4; Cxcl3 NM_002090.2; Cxcl4 (Pf4) NM_002619.2; Cxcr3 NM_001504.1; Cxcr6 NM_006564.1; Cxcr7 NM_020311.1; DCK NM_000788.2; DCT NM_001922.3; Dab1 NM_021080.3; Dap10 (HCST) NM_001007469.1; Dap12 (TYROBP) NM_003332.2; Def6 NM_022047.3; Defb1 NM_005218.3; Defb2 NM_004942.2; Dgkz NM_001105540.1; Dpp4 (CD26) NM_001935.3; Dsc1 NM_024421.2; Dsc2 NM_024422.3; Dsg2 NM_001943.3; EEF1G NM_001404.4; EGF NM_001963.3; Efemp1 NM_004105.3; Egfr NM_201282.1; Egr2 NM_000399.3; Eomes NM_005442.2; Epcam NM_002354.1; Ezr NM_003379.4; F2R (PAR-1) NM_001992.2; F2RL1 (PAR-2) NM_005242.3; FCER1A NM_002001.2; FCGR2A (CD32) NM_021642.2; FN1 NM_212482.1; Fap NM_004460.2; Fasl (TNFSF6) NM_000639.1; Fcgr2b (CD32b) NM_001002273.1; Fcrl3 NM_052939.3; Folr4 NM_001199206.1; Foxp3 NM_014009.3; G6PD NM_000402.2; GAPDH NM_002046.3; GUSB NM_000181.1; Gas6 NM_000820.2; Gata3 NM_001002295.1; Gdf10 NM_004962.2; Gfi1 NM_005263.2; Gitr (Tnfrsf18) NM_004195.2; Gitrl (Tnfsf18) NM_005092.2; Gnly NM_006433.2; Gpld1 NM_001503.2; gpr18 NM_001098200.1; Grap2 NM_004810.2; Gzma NM_006144.2; Gzmb NM_004131.3; Gzmk NM_002104.2; HLA-A (HLA NM_002116.5; Class I) HLA-B NM_005514.6; HLA-C NM_002117.4; HLA-DRA NM_019111.3; (HLA class II) HLA-E NM_005516.4; HPRT1 NM_000194.1; Havcr1-Tim1 NM_001099414.1; Havcr2-Tim3 NM_032782.3;

Hcls1 NM_005335.4; Hgfac NM_001528.2; Hif1a NM_001530.2; Hopx NM_001145460.1; IFNg NM_000619.2; IGSF6 NM_005849.2; IL-10R1 NM_001558.2; IL-2RA NM_000417.1; IL-2RB NM_000878.2; IL-2Rg NM_000206.1; IL-37 NM_014439.3; IL10 NM_000572.2; IL18 NM_001562.2; IL18R1 NM_003855.2; IL2 NM_000586.2; L4 NM_000589.2; ITGAL (CD11a) NM_002209.2; ITGAM (CD11b) NM_000632.3; Icam1 NM_000201.1; Icos NM_012092.2; IcosL (B7-H2) NM_015259.4; Id2 NM_002166.4; Ido1 (Indo) NM_002164.3; Ifi16 NM_005531.1; Ifitm1 NM_003641.3; Ifngr2 NM_005534.3; Igf1 NM_000618.3; Igj NM_144646.3; Ikzf3 NM_012481.3; Ing1 NM_198219.1; Ing2 NM_001564.2; Insr NM_000208.1; Irf1 NM_002198.1; Irf2 NM_002199.2; Irf4 NM_002460.1; Irf6 NM_006147.2; Irf7 W001572.3; Irf8 NM_002163.2; Itga1 (CD49) NM_181501.1; Itga2 (CD49b) NM_002203.2; Itgae (CD103) NM_002208.4; Itgax NM_000887.3; Itk NM_005546.3; Itm2a NM_004867.4; Jak3 NM_000215.2; Jakmip1 NM_001099433.1; KIR2DL1 NM_014218.2; KLK6 NM_002774.3; KLRG2 (CLEC15b) NM_198508.2; Klrc1 (NKG2A) NM_002259.3; Klrc2 (NKG2c) NM_002260.3; Klrd1 (CD94) NM_002262.3; Klrk1-NKG2D NM_007360.1; LAIR1 NM_002287.3; LIFR NM_002310.3; LILRA1 (CD85I) NM_006863.1; LILRA2 $v_1$-2 NM_001130917.1; (CD85H) LILRA4 (CD85G) NM_012276.3; LILRA5 $v_3$-4 NM_181879.1; (CD85F) Lag3 (CD223) NM_002286.5; Lamp2 NM_002294.2; Lat NM_001014987.1; Lat2-linker for NM_014146.3; activation of T cells family member 2 Lax1 NM_001136190.1; Lck NM_005356.2; Lgals3 NM_001177388.1; Lgals3BP NM_005567.3; Lgals9-lectin NM_002308.3; LilRB4 NM_001081438.1; Lst1 NM_001166538.1; Ltk NM_002344.5; Ly6e NM_002346.2; Ly6g6c NM_025261.2; Ly6g6d NM_021246.2; MAGEA1-NM_004988.4; melanoma antigen family A MBL2 NM_000242.2; MER (MERTK) NM_006343.2; MLANA (Mart1) NM_005511.1; MON1B NM_014940.2; MSA41 (CD20) NM_152866.2; Maf NM_001031804.2; Mafb NM_005461.3; Marco (Scara2) NM_006770.3; Mica NM_000247.1; Micb NM_005931.3; Mn1 NM_002430.2; Mrc1 NM_002438.2; Myh4 NM_017533.2; NCR2-NKp44 NM_004828.3; Nfatc1 NM_172389.1; Nkg7 NM_005601.3; N1rp10 (NOD) NM_176821.3; Nr4a2 NM_006186.3; Ny-eso-1 (CTAG1B) NM_001327.2; OAZ1 NM_004152.2; OSCAR NM_130771.3; PARK7 NM_001123377.1; PD-1 (Pdcd1) NM_005018.1; PDCD4 NM_014456.3; POLR$^{1B}$ NM_019014.3; POLR2A NM_000937.2; PPARG NM_015869.3; PPIA NM_021130.2; Pdcd1Lg2 (PD-L2) NM_025239.3; Pdgfra NM_006206.3; Phactr2 NM_001100164.1; Pi3kCA NM_006218.2; Pi3kCB NM_006219.1; Pi3kCD NM_005026.3; Pi3kCG NM_002649.2; Pilra (FDF03 NM_178273.1; inhibited) Pilrb (FDF03 NM_178238.1; activated) Postn NM_001135935.1; Ppplr2 NM_006241.4; Prf1 NM_005041.3; Psmb10 NM_002801.2; Psmb8 NM_004159.4; Psmb9 NM_002800.4; Psme1 NM_006263.2; Psme2 NM_002818.2; Pstpip1 NM_003978.3; Pstpip2 NM_024430.3; Pten NM_000314.3; Ptger2 NM_000956.2; Ptger4 NM_000958.2; Ptpn10 (Dusp1) NM_004417.2; Ptpn13 NM_080684.2; Ptpn22 NM_015967.3; Ptpn3 NM_001145372.1; Ptpn6 NM_002831.5; Ptpn7 NM_002832.3; Ptprcap NM_005608.2; Ptprf NM_002840.3; Pvrig NM_024070.3; RGS16 NM_002928.2; RIKEN cDNA NM_022153.1; 4632428N05 (VISTA) RPL19 NM_000981.3; Rarres2 NM_002889.3; Retnlb (Relmb Fizz2) NM_032579.2; Rgn NM_152869.2; Rora NM_134261.2; Rorc (RORg and T) NM_001001523.1; Runx1 NM_001754.4; Runx3 NM_004350.1; S100a8 NM_002964.3; S100a9 NM_002965.2; SAMD3 NM_001017373.2; SART3 NM_014706.3; SDHA NM_004168.1; SIGLEC14 NM_001098612.1; SIGLEC15 NM_213602.2; _(CD33L3) SIGLEC5 (CD170; NM_003830.2; CD33L2) Samhd1 NM_015474.2; Sema4a NM_001193300.1; Serpinf1 NM_002615.4; Sgpp2 NM_152386.2; Sh2d1b NM_053282.4; Sh2d2a NM_001161443.1; Sirpb1 NM_006065.3; Sirpg NM_001039508.1; Sit1 NM_014450.2; Sla1 NM_001045556.2; Sla2 NM_032214.2; Slamf1 (CD150 NM_003037.2; Slam) Slamf6 (ntba) NM_001184714.1; Slamf7 (Cracc) NM_021181.3; Socs3 NM_003955.3; Stat1 NM_007315.2; Stat6 NM_003153.3; TBP NM_001172085.1; TIMP3 NM_000362.4; TIMP4 NM_003256.2; TNFRSF10b-NM_003842.3; TRAIL $R^2$ DR5 TNFRSF13B-TACI NM_012452.2; TNFRSF8-CD30 NM_152942.2; TNFSF10-TRAIL NM_003810.2; CD253 TNFSF13b-BLYS NM_006573.4; TNFSF8-CD30L NM_001244.2; TREM1 NM_018643.3; TREM2 NM_018965.2; TREML1 (TLT-1) NM_178174.2; TREML2 (TLT-2) NM_024807.2; TUBB NM_178014.2; TYR (Tyrosinase) NM_000372.4; TYRO3 NM_006293.2; Tagap NM_054114.3; Tarp (TCR gamma NM_001003799.1; alternate reading frame protein) Tbx21 (Tbet) NM_013351.1; Tcn2 NM_000355.2; Tigit NM_173799.2; Tmem2 NM_013390.2; Tnfa NM_000594.2; Tnfaip3 NM_006290.2; Tnfaip6 NM_007115.2; Tnfaip8L2 NM_024575.3; Tnfrsf14 (Hvem) NM_003820.2; Tnfrsf4 (Ox40) NM_003327.2; Tnfrsf7 (Cd27) NM_001242.4; Tnfrsf9 (CD137 4-NM_001561.4; 1BB) Tnfsf14 (LIGHT) NM_003807.2; Tnfsf4 NM_003326.2; Tnfsf7 CD27L NM_001252.2; Tnfsf9 (4-1BBL) NM_003811.3; Tox NM_014729.2; Trat1 NM_016388.2; UBB NM_018955.2; Ubash3a NM_001001895.1; Ubash3b NM_032873.3; VCAM NM_001078.3; Xist NR_001564.1; Zap70 NM_001079.3; Zbtb16 NM_006006.4; Zbtb32 NM_014383.1.

In embodiments, each of the steps of obtaining a tissue sample, preparing one or more tissue sections therefrom for a gene signature biomarker assay, performing the assay, and scoring the results may be performed by separate individuals/entities at separate locations. For example, a surgeon may obtain by biopsy a tissue sample from a cancer patient's tumor and then send the tissue sample to a pathology lab, which may fix the tissue sample and then prepare one or more slides, each with a single tissue section, for the assay. The slide(s) may be assayed soon after preparation, or stored for future assay. The lab that prepared a tissue section may conduct the assay or send the slide(s) to a different lab to conduct the assay. A pathologist or trained professional who scores the slide(s) for an T-effector gene signature may work for the diagnostic lab, or may be an independent contractor. Alternatively, a single diagnostic lab obtains the tissue sample from the subject's physician or surgeon and then performs all of the steps involved in preparing tissue sections, assaying the slide(s) and calculating the gene signature score for the tissue section(s).

In embodiments, the individuals involved with preparing and assaying the tissue section for a gene signature biomarker do not know the identity of the subject whose sample is being tested; i.e., the sample received by the laboratory is made anonymous in some manner before being sent to the laboratory. For example, the sample may be merely identified by a number or some other code (a "sample ID") and the results of the assay are reported to the party ordering the test using the sample ID. In embodiments, the link between the identity of a subject and the subject's tissue sample is known only to the individual or to the individual's physician.

In embodiments, after the test results have been obtained, the diagnostic laboratory generates a test report, which may comprise any one or both of the following results: the tissue sample was biomarker positive or negative, the gene signature score for the tumor sample and the reference score for that gene signature. The test report may also include a list of genes whose expression was analyzed in the assay.

In embodiments, the test report may also include guidance on how to interpret the results for predicting if a subject is likely to respond to an A2A receptor antagonist. For example, in one embodiment, the tested tumor sample is from a solid tumor and has an T-effector gene signature score at or above a prespecified threshold, the test report may indicate that the subject has a score that is associated with response or better response to treatment with an A2A receptor antagonist, while if the T-effector gene signature score is below the threshold, then the test report indicates that the patient has a score that is associated with no response or poor response to treatment with an A2A receptor antagonist.

In embodiments, the test report is a written document prepared by the diagnostic laboratory and sent to the patient or the patient's physician as a hard copy or via electronic mail. In embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

In embodiments, the presence or absence of an T-effector gene signature is performed using a kit that has been specially designed for this purpose. In embodiments, the kit comprises binding agents (e.g., a set of oligonucleotide probes capable of hybridizing to the target transcripts in the gene signature). In embodiments, the kit may further comprise oligonucleotide probes capable of detecting transcripts of other genes, such as control genes, or genes used for normalization purposes. In embodiments, the set of oligonucleotide probes may comprise an ordered array of oligonucleotides on a solid surface, such as a microchip, silica beads (such as BeadArray technology from Illumina, San Diego, Calif.), or a glass slide (see, e.g., WO 98/20020 and WO 98/20019). In embodiments, the oligonucleotide probes are provided in one or more compositions in liquid or dried form.

In embodiments, oligonucleotides in kits are capable of specifically hybridizing to a target region of a polynucleotide, such as for example, an RNA transcript or cDNA generated therefrom. As used herein, specific hybridization means the oligonucleotide forms an anti-parallel double-stranded structure with the target region under certain hybridizing conditions, while failing to form such a structure with non-target regions when incubated with the polynucleotide under the same hybridizing conditions. The composition and length of each oligonucleotide in the kit will depend on the nature of the transcript containing the target region as well as the type of assay to be performed with the oligonucleotide and is readily determined by the skilled artisan.

In embodiments, each oligonucleotide in the kit is a perfect complement of its target region. An oligonucleotide is the to be a "perfect" or "complete" complement of another nucleic acid molecule if every nucleotide of one of the molecules is complementary to the nucleotide at the corresponding position of the other molecule. While perfectly complementary oligonucleotides are preferred for detecting transcripts in a gene signature, departures from complete complementarity are contemplated where such departures do not prevent the molecule from specifically hybridizing to the target region as defined above. For example, an oligonucleotide probe may have one or more non-complementary nucleotides at its 5' end or 3' end, with the remainder of the probe being completely complementary to the target region. Alternatively, non-complementary nucleotides may be interspersed into the probe as long as the resulting probe is still capable of specifically hybridizing to the target region.

In embodiments, each oligonucleotide in the kit specifically hybridizes to its target region under stringent hybridization conditions. Stringent hybridization conditions are sequence-dependent and vary depending on the circumstances. In embodiments, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. As the target sequences are generally present in excess, at Tm, 50% of the probes are occupied at equilibrium.

In embodiments, stringent conditions include a salt concentration of at least about 0.01 to 1.0 M sodium ion concentration (or other salts) at pH 7.0 to 8.3 and the temperature is at least about 25° C. for short oligonucleotide probes (e.g., 10 to 50 nucleotides). In embodiments, stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations. Additional stringent conditions can be found in Molecular Cloning: A Laboratory Manual, Sambrook et al., Cold Spring Harbor Press, Cold Spring Harbor, N.Y. (1989), chapters 7, 9, and 11, and in Nucleic Acid Hybridization, A Practical Approach, Haymes et al., IRL Press, Washington, D.C., 1985. One non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Stringency conditions with ranges intermediate to the above-recited values, e.g., at 65-70° C. or at 42-50° C. are also intended to be encompassed by the present invention. SSPE (1×SSPE is 0.15M NaCl, 10 mM NaH2PO4, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete.

In embodiments, the hybridization temperature for hybrids anticipated to be less than 50 base pairs in length should be 5-10° C. less than the melting temperature (Tm)

of the hybrid, where Tm is determined according to the following equations. In embodiments, for hybrids less than 18 base pairs in length, Tm(° C.)=2(# of A+T bases)+4(# of G+C bases). In embodiments, for hybrids between 18 and 49 base pairs in length, Tm(° C.)=81.5+16.6(log 10[Na+])+ 0.41(% G+C)−(600/N), where N is the number of bases in the hybrid, and [Na+] is the concentration of sodium ions in the hybridization buffer ([Na+] for 1×SSC=0.165 M).

In embodiments, oligonucleotides in kits may be comprised of any phosphorylation state of ribonucleotides, deoxyribonucleotides, and acyclic nucleotide derivatives, and other functionally equivalent derivatives. In embodiments, the oligonucleotides may have a phosphate-free backbone, which may be comprised of linkages such as carboxymethyl, acetamidate, carbamate, polyamide (peptide nucleic acid (PNA)) and the like (Varma, in Molecular Biology and Biotechnology, A Comprehensive Desk Reference, Meyers, ed., pp. 6 17-20, VCH Publishers, Inc., 1995). In embodiments, the oligonucleotides may be prepared by chemical synthesis using any suitable methodology known in the art, or may be derived from a biological sample, for example, by restriction digestion. In embodiments, the oligonucleotides may contain a detectable label, according to any technique known in the art, including use of radiolabels, fluorescent labels, enzymatic labels, proteins, haptens, antibodies, sequence tags and the like. In embodiments, the oligonucleotides in the kit may be manufactured and marketed as analyte specific reagents (ASRs) or may be constitute components of an approved diagnostic device.

Exemplary kits provided herein may also contain other reagents such as hybridization buffer and reagents to detect when hybridization with a specific target molecule has occurred. In embodiments, detection reagents may include biotin- or fluorescent-tagged oligonucleotides and/or an enzyme-labeled antibody and one or more substrates that generate a detectable signal when acted on by the enzyme. It will be understood by the skilled artisan that the set of oligonucleotides and reagents for performing the assay will be provided in separate receptacles placed in the kit container if appropriate to preserve biological or chemical activity and enable proper use in the assay.

In embodiments, each of the oligonucleotide probes and all other reagents in the kit have been quality tested for optimal performance in an assay designed to determine the T-effector gene signature score in a tumor sample, and preferably when the tumor sample is an FFPE tissue section. In embodiments, the kit includes an instruction manual that describes how to use the determined gene signature score to assign, to the tested tumor sample, the presence or absence of a gene signature biomarker that predicts response to treatment with an A2A receptor antagonist.

Patient Selection, Monitoring, and Dosage Adjustment

In embodiments, treatment or dosage efficacy of an adenosine receptor antagonist can be determined for patients treated with adenosine receptor antagonists and/or PD-1 pathway inhibitors. In embodiments, an increased level of tumor infiltrating lymphocytes, increased T cell receptor diversity, and/or increased PD-L1 levels indicates likely efficacy of an adenosine receptor antagonist. In embodiments, the tumor infiltrating lymphocytes are CD8 T cells.

An individual patient reaction to treatment with an adenosine receptor antagonist (e.g. an A2A receptor or A2B receptor antagonist) can be predicted by measuring whether a cancer tumor comprises an elevated level of tumor infiltrating lymphocytes relative to a control, a subject comprises an increased cancer tumor T cell receptor diversity or blood T cell receptor diversity relative to a control, a cancer tumor comprises an elevated level of PD-L1 relative to a control, a subject has an increased level of a T-effector signature compared to a control, or a cancer tumor or blood of a subject comprises an elevated level of CD73 relative to a control.

In embodiments, in patients treated with adenosine receptor antagonists (such as adenosine-A2A receptor antagonists), alone or in combination with a PD-1 pathway inhibitor, effects on tumor infiltrating lymphocytes (e.g., the level of tumor infiltrating lymphocytes in a solid tumor), T cell receptor diversity, and PD-L1 levels can be used to determine treatment or dosage efficacy of the adenosine receptor antagonist therapy. In embodiments, an increase in the level of tumor infiltrating lymphocytes, increased T cell receptor diversity, and/or increased PD-L1 levels indicates efficacy of an adenosine receptor antagonist. In embodiments, the tumor infiltrating lymphocytes are CD8 T cells.

An individual patient reaction to treatment with an adenosine receptor antagonist (e.g. an A2A receptor or A2B receptor antagonist) can be detected by measuring of cellular effects. In embodiments, cellular effects of treatment can be monitored in a patient sample (e.g. a blood or a tumor sample such as a biopsy). In embodiments, a blood sample is used to assay T cell receptor diversity. In embodiments, a tumor sample (such as a biopsy, e.g., a core needle biopsy) is used to assay the level of tumor infiltrating lymphocytes (such as infiltrating CD8 T cells) in a tumor, and/or PD-L1 levels.

In embodiments, cells are isolated from a patient sample (e.g. a blood or tumor sample). In embodiments, a level of tumor infiltrating lymphocytes, T cell receptor diversity, and/or PD-L1 is detected prior to treatment with an adenosine receptor antagonist (e.g. prior to treatment with CPI-444). In embodiments, an additional sample is collected (and detection is performed) following treatment with an adenosine receptor antagonist, alone or in combination with another agent (e.g. CPI-444, or CPI-444 combination therapy with atezolizumab). In embodiments, the tumor infiltrating lymphocytes are CD8 T cells. In embodiments, a sample is collected after about 7 days, 8 days, 9 days, 10 days, 11 days, 12 days, 13 days, 2 weeks, 3 weeks, 4 weeks, 8 weeks, 12 weeks or more following treatment with an adenosine receptor antagonist. A comparison can be made between a level of tumor infiltrating lymphocytes, T cell receptor diversity, and/or PD-L1 prior to and following treatment with an adenosine receptor antagonist to determine the degree to which treatment has been effective.

In embodiments, the level of tumor infiltrating lymphocytes, T cell receptor diversity, and/or PD-L1 is detected in a subject (e.g., monitored) at least 2, 3, 4, 5, 6, 7, 8, 9, or 10 time points. In embodiments, the tumor infiltrating lymphocytes are CD8 T cells. In embodiments, at least one of the time points is prior to the administration of an adenosine receptor antagonist. In embodiments, 2 or more or all of the time points are about or at least about or less than about 1, 2, 3, 4, 5, 6, 7, 8, 9, 10, 11, or 12 days, weeks, months, or years apart from each other. In embodiments, the dose of an adenosine receptor antagonist is adjusted over time based at least in part on the level of tumor infiltrating lymphocytes, T cell receptor diversity, and/or PD-L1. In embodiments, subjects who display an increase in the level of tumor infiltrating lymphocytes, increased T cell receptor diversity, and/or increased PD-L1 levels by an adenosine receptor antagonist following treatment with an adenosine receptor antagonist are identified as responsive to treatment with adenosine receptor antagonists. In embodiments, a subject who is responsive to treatment with adenosine receptor antagonists receives further administration of an adenosine receptor antagonist. In embodiments, subjects who do not display an increase in the level of tumor infiltrating lymphocytes, increased T cell receptor diversity, and/or increased PD-L1 levels by an adenosine receptor antagonist following treatment with an adenosine receptor antagonist are identified as insufficiently responsive to treatment with adenosine receptor antagonists. In embodiments, a subject who is insufficiently responsive to treatment with adenosine receptor antagonists receives an increase in the dose of an adenosine receptor antagonist, and/or increased frequency of administration of a dose of an adenosine receptor antagonist.

EMBODIMENTS 1 TO 92

Embodiment 1

A method of treating a cancer tumor in a subject in need thereof, the method comprising administering to the subject a therapeutically effective amount of an adenosine-A2A receptor antagonist, wherein: (i) the cancer tumor or blood of the subject comprises an elevated level of CD73 relative to a control; (ii) the cancer tumor comprises an elevated level of tumor infiltrating lymphocytes relative to a control; (iii) the subject comprises an increased cancer tumor T cell receptor diversity or blood T cell receptor diversity relative to a control; (iv) the cancer tumor comprises an elevated level of PD-L1 relative to a control; (v) the subject has an increased level of a T-effector signature compared to a control; or (vi) a combination of two or more of the foregoing Embodiment 2

The method of Embodiment 1, wherein the adenosine-A2A receptor antagonist is a compound of formula (I):

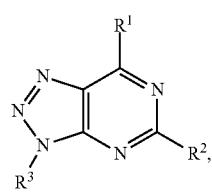

wherein, $R^1$ is independently hydrogen, halogen, $-CX^a_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$,
$-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, halogen, $-CX^b_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$,
$-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, halogen, $-CX^c_3$, $-CN$, $-SO_2Cl$, $-SO_{n3}R^{13}$, $-SO_{v3}NR^{13}R^{14}$, $-NHNH_2$, $-ONR^{13}R^{14}$, $-NHC=(O)NHNH_2$, $-NHC=(O)NR^{13}R^{14}$,
$-N(O)_{m3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$, $R^{10}$, $R^{11}$, $R^{12}$, $R^{13}$ and $R^{14}$ are independently hydrogen, halogen, =O, =S, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $X^a$, $X^b$ and $X^c$ are independently $-F$, $-Cl$, $-Br$, or $-I$; $n_1$, $n_2$ and $n_3$ are independently an integer from 0 to 4; $m_1$, $m_2$ and $m_3$ are independently an integer from 1 to 2; and $v_1$, $v_2$ and $v_3$ are independently an integer from 1 to 2

Embodiment 3

The method of Embodiment 1, wherein the adenosine-A2A receptor antagonist is a compound of formula (II):

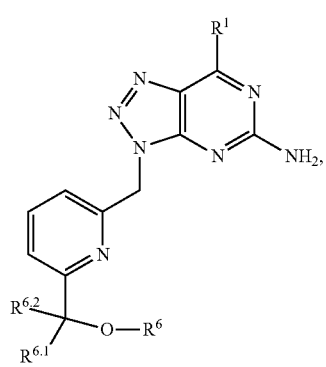

wherein the substituents are as defined herein.

Embodiment 4

The method of Embodiment 1, wherein the adenosine-A2A receptor antagonist is a compound of formula (III):

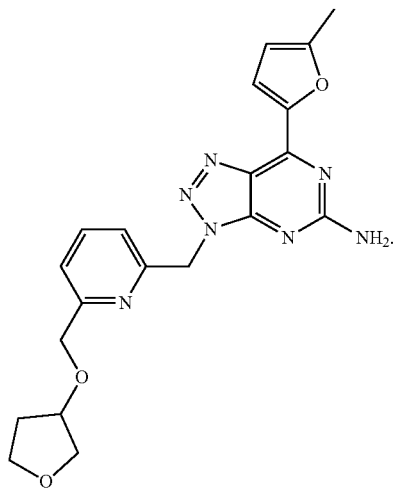

(III)

Embodiment 5

The method of Embodiment 1, wherein the adenosine-A2A receptor antagonist is a compound of formula (IIIA):

(IIIA)

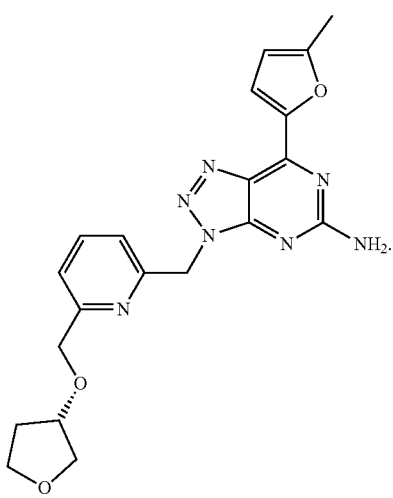

Embodiment 6

The method of Embodiment 1, wherein the adenosine-A2A receptor antagonist is a compound of formula (IIIB):

(IIIB)

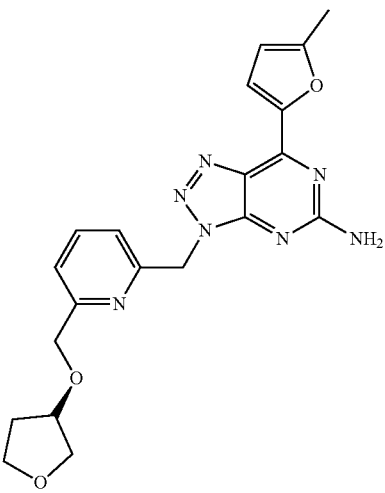

Embodiment 7

The method of Embodiment 1, wherein the adenosine-A2A receptor antagonist is a mixture of the compound of formula (IIIA) and the compound of formula (IIIB).

Embodiment 8

The method of any one of Embodiments 1 to 7, further comprising administering to the subject a therapeutically effective amount of a PD-1 signaling pathway inhibitor.

Embodiment 9

The method of Embodiment 8, wherein the PD-1 signaling pathway inhibitor is atezolizumab.

Embodiment 10

The method of any one of Embodiments 1 to 9, further comprising administering to the subject a therapeutically effective amount of an anti-cancer agent.

Embodiment 11

The method of any one of Embodiments 1 to 10, wherein the cancer tumor comprises an elevated level of CD73 relative to a control.

Embodiment 12

The method of any one of Embodiments 1 to 11, wherein the blood of the subject comprises an elevated level of CD73 relative to a control

Embodiment 13

The method of any one of Embodiments 1 to 12, wherein the cancer tumor comprises an elevated level of tumor infiltrating lymphocytes relative to a control.

Embodiment 14

The method of Embodiment 13, wherein the tumor infiltrating lymphocytes are tumor infiltrating T cells.

Embodiment 15

The method of Embodiment 14, wherein the T cells are CD8 T cells.

Embodiment 16

The method of any one of Embodiments 13 to 15, wherein about 1% to about 4% of the cells in a region of the tumor are CD8 T cells.

Embodiment 17

The method of Embodiment 16, wherein the region is the center of the cancer tumor.

Embodiment 18

The method of any one of Embodiments 14 to 17, wherein the T cells are effector memory T cells.

Embodiment 19

The method of any one of Embodiments 13 to 18, wherein elevated level of tumor infiltrating lymphocytes comprise: (i) an elevated level of the number of tumor infiltrating lymphocytes; (ii) an elevated tumor infiltrating lymphocyte activity; or (iii) an elevated level of the number of tumor infiltrating lymphocytes and an elevated tumor infiltrating lymphocyte activity.

Embodiment 20

The method of any one of Embodiments 1 to 19, wherein a biological sample obtained from the subject comprises increased T cell receptor diversity relative to a control.

Embodiment 21

The method of Embodiment 20, wherein the subject has a peripheral blood clonality of less than about 0.3.

Embodiment 22

The method of any one of Embodiments 1 to 21, wherein the cancer tumor comprises an elevated level of PD-L1 relative to a control.

Embodiment 23

The method of Embodiment 22, wherein the cancer tumor comprises an elevated level of PD-L1 in tumor infiltrating lymphocytes relative to a control.

Embodiment 24

The method of Embodiment 22, wherein the cancer tumor comprises an elevated level of PD-L1 in all tumor cells relative to a control.

Embodiment 25

The method of any one of Embodiments 1 to 24, wherein the subject has an increased level of a T-effector signature compared to a control.

Embodiment 26

The method of Embodiment 25, wherein the T-effector signature is the level of expression of any combination of 2, 3, 4, 5, 6, 7, 8, 9, 10, 11, 12, 13, 14, 15, 16, 17, or 18 of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, L7R, and CD44.

Embodiment 27

The method of any one of Embodiments 1 to 26, wherein the subject comprises an increased cancer tumor T cell receptor diversity relative to a control.

Embodiment 28

The method of any one of Embodiments 1 to 27, wherein the subject comprises an increased cancer blood T cell receptor diversity relative to a control.

Embodiment 29

The method of any one of Embodiments 1 to 10, wherein the subject comprises an elevated level of tumor infiltrating lymphocytes relative to a control, the subject comprises an increased cancer tumor T cell receptor diversity or blood T cell receptor diversity relative to a control, the cancer tumor comprises an elevated level of PD-L1 relative to a control, or the cancer tumor or the blood of the subject comprises an elevated level of CD73 relative to a control prior to administration of the adenosine-A2A receptor antagonist.

Embodiment 30

The method of any one of Embodiments 1 to 10, wherein subject comprises an elevated level of tumor infiltrating lymphocytes relative to a control, the subject comprises an increased cancer tumor T cell receptor diversity or blood T cell receptor diversity relative to a control, or the cancer tumor comprises an elevated level of PD-L1 relative to a control, or the cancer tumor or the blood of the subject comprises an elevated level of CD73 relative to a control, after administration of the adenosine-A2A receptor antagonist.

Embodiment 31

The method of any one of Embodiments 8 to 30, wherein the adenosine-A2A receptor antagonist and the PD-1 signaling pathway inhibitor are administered in a combined synergistic amount.

Embodiment 32

The method of any one of Embodiments 1 to 31, wherein the adenosine-A2A receptor antagonist is administered at 100 mg.

Embodiment 33

The method of any one of Embodiments 1 to 31, wherein the adenosine-A2A receptor antagonist is administered once a day or twice a day.

Embodiment 34

The method of any one of Embodiments 8 to 33, wherein the PD-1 signaling pathway inhibitor is administered in an amount of about 840 mg.

Embodiment 35

The method of any one of Embodiments 8 to 34, wherein the PD-1 signaling pathway inhibitor is administered once every two weeks.

Embodiment 36

The method of any one of Embodiments 8 to 33 and 35, wherein the PD-1 signaling pathway inhibitor is administered in an amount of about 1200 mg.

Embodiment 37

The method of any one of Embodiments 8 to 33 and 36, wherein the PD-1 signaling pathway inhibitor is administered once every three weeks.

Embodiment 38

The method of any one of Embodiments 31 to 37, wherein the adenosine-A2A receptor antagonist is a compound of formula (III) and the PD-1 signaling pathway inhibitor is atezolizumab.

Embodiment 39

The method of any one of Embodiments 31 to 37, wherein the adenosine-A2A receptor antagonist is the compound of formula (IIIA) or the compound of formula (IIIB); and the PD-1 signaling pathway inhibitor is atezolizumab.

Embodiment 40

The method of any one of Embodiments 31 to 37, wherein the adenosine-A2A receptor antagonist is a mixture of the compound of formula (IIIA) and the compound of formula (IIIB), and the PD-1 signaling pathway inhibitor is atezolizumab.

Embodiment 41

The method of any one of Embodiments 1 to 40, wherein the cancer is colon cancer.

Embodiment 42

The method of any one of Embodiments 1 to 40, wherein the cancer is non-small cell lung cancer.

Embodiment 43

The method of any one of Embodiments 1 to 40, wherein the cancer is triple negative breast cancer.

Embodiment 44

The method of any one of Embodiments 1 to 40, wherein the cancer is melanoma.

Embodiment 45

The method of any one of Embodiments 1 to 40, wherein the cancer is a head and neck cancer.

Embodiment 46

The method of any one of Embodiments 1 to 40, wherein the cancer is colorectal cancer.

Embodiment 47

The method of any one of Embodiments 1 to 40, wherein the cancer is prostate cancer.

Embodiment 48

The method of any one of Embodiments 1 to 40, wherein the cancer is bladder cancer.

Embodiment 49

The method of any one of Embodiments 1 to 40, wherein the cancer is renal cancer.

Embodiment 50

A method of treating a cancer tumor in a subject in need thereof, the method comprising: (i) determining whether: (a) the cancer tumor or blood of the subject comprises an elevated level of CD73 relative to a control; (b) the cancer tumor comprises elevated levels of tumor infiltrating lymphocytes relative to a control; (c) the subject comprises an increased cancer tumor T cell receptor diversity or blood T cell receptor diversity relative to a control; (d) the cancer tumor comprises an elevated level of PD-L1 relative to a control, or (e) the subject has an increased level of a T-effector signature compared to a control; and (ii) administering to the subject a therapeutically effective amount of an adenosine-A2A receptor antagonist

Embodiment 51

The method of Embodiment 50, comprising obtaining a biological sample from the subject to determine whether: (a) the cancer tumor or blood of the subject comprises an elevated level of CD73 relative to a control; (b) the cancer tumor comprises elevated levels of tumor infiltrating lymphocytes relative to a control; (c) the subject comprises an increased cancer tumor T cell receptor diversity or blood T cell receptor diversity relative to a control; (d) the cancer tumor comprises an elevated level of PD-L1 relative to a control, or (e) the subject has an increased level of a T-effector signature compared to a control.

Embodiment 52

The method of Embodiment 50 or 51, wherein the adenosine-A2A receptor antagonist is a compound of formula:

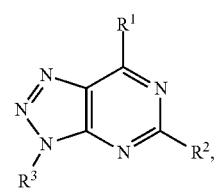

(I)

wherein the substituents are as defined in Embodiment 2.

Embodiment 53

The method of Embodiment 50 or 51, wherein the adenosine-A2A receptor antagonist is a compound of formula (II):

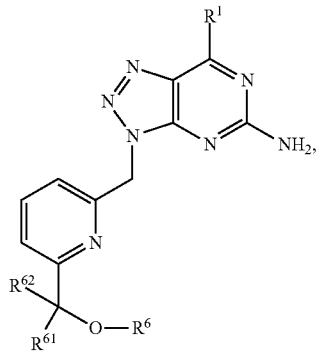

(II)

wherein the substituents are as defined herein.

Embodiment 54

The method of Embodiment 50 or 51, wherein the adenosine-A2A receptor antagonist is a compound of formula (III):

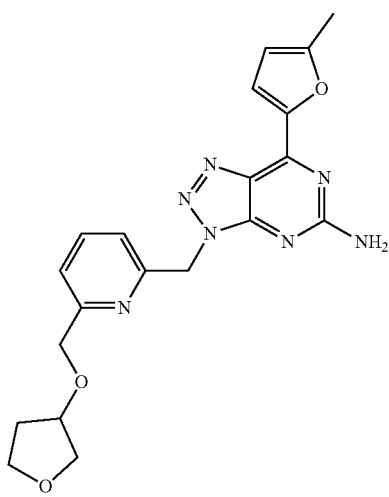

(III)

Embodiment 55

The method of Embodiment 50 or 51, wherein the adenosine-A2A receptor antagonist is a compound of formula (IIIA):

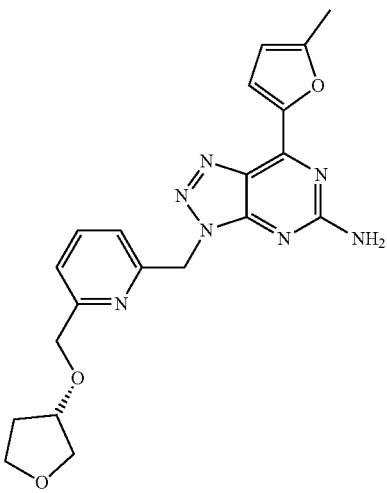

(IIIA)

Embodiment 56

The method of Embodiment 50 or 51, wherein the adenosine-A2A receptor antagonist is a compound of formula (IIIB):

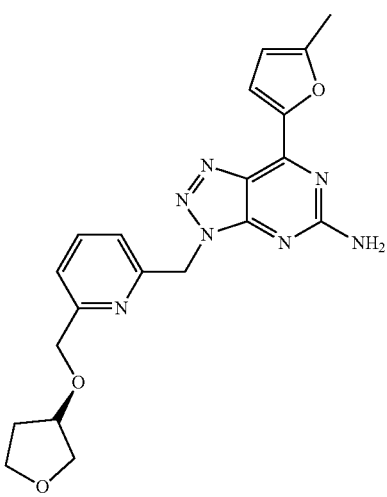

(IIIB)

Embodiment 57

The method of Embodiment 50 or 51, wherein the adenosine-A2A receptor antagonist is a mixture of the compound of formula (IIIA) and the compound of formula (IIIB).

Embodiment 58

The method of any one of Embodiments 50 to 57, further comprising administering to the subject a therapeutically effective amount of a PD-1 signaling pathway inhibitor.

Embodiment 59

The method of Embodiment 58, wherein the PD-1 signaling pathway inhibitor is atezolizumab.

Embodiment 60

The method of any one of Embodiments 50 to 59, further comprising administering to the subject a therapeutically effective amount of an anti-cancer agent.

Embodiment 61

The method of any one of Embodiments 51 to 60, wherein the biological sample comprises a tumor biopsy, blood, serum, or plasma.

Embodiment 62

The method of any one of Embodiments 50 to 61, wherein determining whether the cancer tumor comprises elevated levels of tumor infiltrating lymphocytes comprises detecting a T-effector signature.

Embodiment 63

The method of Embodiment 62, wherein the T-effector signature is the level of expression of any combination of 2, 3, 4, 5, 6, 7, 8, 9, 10, 11, 12, 13, 14, 15, 16, 17, or 18 of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, L7R, and CD44 compared to a control.

Embodiment 64

The method of any one of Embodiments 50 to 63, wherein the cancer tumor has an elevated level of tumor infiltrating lymphocytes relative to a control.

Embodiment 65

The method of Embodiment 64, wherein the tumor infiltrating lymphocytes are tumor infiltrating T cells.

Embodiment 66

The method of Embodiment 65, wherein the T cells are CD8 T cells.

Embodiment 67

The method of Embodiment 66, wherein at about 1% to about 4% of the cells in a region of the tumor are CD8 T cells.

Embodiment 68

The method of Embodiment 67, wherein the region is the center of the cancer tumor.

Embodiment 69

The method of any one of Embodiments 50 to 68, wherein the cancer is colon cancer.

Embodiment 70

The method of any one of Embodiments 50 to 68, wherein the cancer is non-small cell lung cancer.

Embodiment 71

The method of any one of Embodiments 50 to 68, wherein the cancer is triple negative breast cancer.

Embodiment 72

The method of any one of Embodiments 47 to 65, wherein the cancer is melanoma.

Embodiment 73

The method of any one of Embodiments 50 to 68, wherein the cancer is head and neck cancer.

Embodiment 74

The method of any one of Embodiments 50 to 68, wherein the cancer is colorectal cancer.

Embodiment 75

The method of any one of Embodiments 50 to 68, wherein the cancer is prostate cancer.

Embodiment 76

The method of any one of Embodiments 50 to 68, wherein the cancer is bladder cancer.

Embodiment 77

The method of any one of Embodiments 50 to 68, wherein the cancer is renal cancer.

Embodiment 78

The method of any one of Embodiments 1 to 77, wherein the subject is naïve to PD-1 pathway inhibitor therapy.

Embodiment 79

The method of any one of Embodiments 1 to 77, wherein the subject is a PD-1 pathway resistant subject.

Embodiment 80

The method of any one of Embodiments 1 to 77, wherein the subject is a PD-1 pathway refractory subject.

Embodiment 81

The method of Embodiment 80, wherein the refractory subject has had less than 5% reduction in tumor volume after administration of an anti-PD-1 compound.

Embodiment 82

The method of Embodiment 80, wherein the refractory subject has a tumor that has increased in volume after administration of an anti-PD-1 compound.

Embodiment 83

The method of Embodiment 81 or 82, wherein the anti-PD-1 compound is atezolizumab.

Embodiment 84

The method of Embodiment 49 or 77, wherein the subject is an nivolumab refractory subject.

Embodiment 85

The method of any one of Embodiments 1 to 84, wherein the cancer is resistant to treatment with pembrolizumab, a tyrosine kinase inhibitor, or an mTOR inhibitor.

Embodiment 86

A method of treating a nivolumab refractory cancer in a subject in need thereof, the method comprising administering to the subject a therapeutically effective amount of an adenosine-A2A receptor antagonist.

Embodiment 87

The method of Embodiment 83, wherein the nivolumab refractory cancer is nivolumab refractory renal cell cancer.

Embodiment 88

The method of Embodiment 83 or 84, wherein the nivolumab refractory cancer is refractory to a tyrosine kinase inhibitor or an mTOR inhibitor.

Embodiment 89

The method of any one of Embodiments 86 to 88, further comprising administering a PD-1 signaling pathway inhibitor.

Embodiment 90

The method of Embodiment 89, wherein the adenosine-A2A receptor antagonist is a compound of formula (III) and the PD-1 signaling pathway inhibitor is atezolizumab.

Embodiment 91

A method of treating a cancer a subject in need thereof, the method comprising administering to the subject a therapeutically effective amount of an adenosine-A2A receptor antagonist; wherein the cancer is resistant to pembrolizumab, a tyrosine kinase inhibitor, or an mTOR inhibitor.

Embodiment 92

The method of Embodiment 91, wherein the cancer is renal cell carcinoma.

EMBODIMENTS P1 TO P55

Embodiment P1

A method of treating a cancer tumor in a subject in need thereof, the method comprising administering to the subject a therapeutically effective amount of an adenosine-A2A receptor antagonist, wherein the cancer tumor comprises an elevated level of tumor infiltrating lymphocytes (TILs) relative to a control, the subject comprises an increased cancer tumor T cell receptor diversity or blood T cell receptor diversity relative to a control, the cancer tumor comprises an elevated level of PD-L1 relative to a control, the subject has an increased level of a T-effector signature compared to a control, or the cancer tumor or blood of the subject comprises an elevated level of CD73 relative to a control.

Embodiment P2

The method of Embodiment P1, wherein the A2A receptor antagonist is a compound of formula:

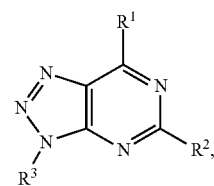

(I)

wherein $R^1$ is independently hydrogen, halogen, —$CX^a_3$, —CN, —$SO_2Cl$, —$SO_{n1}R^9$, —$SO_{v1}NR^9R^{10}$, —$NHNH_2$, —$ONR^9R^{10}$, —NHC=(O)$NHNH_2$, —NHC=(O)$NR^9R^{10}$, —$N(O)_{m1}$, —$NR^9R^{10}$, —NH—O—$R^9$, —C(O)$R^9$, —C(O)—$OR^9$, —C(O)$NR^9R^{10}$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, halogen, —$CX^b_3$, —CN, —$SO_2Cl$, —$SO_{n2}R^{11}$, —$SO_{v2}NR^{11}R^{12}$, —$NHNH_2$, —$ONR^{11}R^{12}$, —NHC=(O)$NHNH_2$, —NHC=(O)$NR^{11}R^{12}$, —$N(O)_{m2}$, —$NR^{11}R^{12}$, —NH—O—$R^{11}$, —C(O)$R^{11}$, —C(O)—$OR^{11}$, —C(O)$NR^{11}R^{12}$, —$OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, halogen, —$CX^c_3$, —CN, —$SO_2Cl$, —$SO_{n3}R^{13}$, —$SO_{v3}NR^{13}R^{14}$, —$NHNH_2$, —$ONR^{13}R^{14}$, —NHC=(O)$NHNH_2$, —NHC=(O)$NR^{13}R^{14}$, —$N(O)_{m3}$, —$NR^{13}R^{14}$, —NH—O—$R^{13}$, —C(O)$R^{13}$, —C(O)—$OR^{13}$, —C(O)$NR^{13}R^{14}$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $X^a$, $X^b$ and $X^c$ are independently —F, —Cl, —Br, or —I; $n_1$, $n_2$ and $n_3$ are independently an integer from 0 to 4; $m_1$, $m_2$ and $m_3$ are independently an integer from 1 to 2; and $v_1$, $v_2$ and $v_3$ are independently an integer from 1 to 2.

Embodiment P3

The method of Embodiment P1 or P2, further comprising administering to the subject a therapeutically effective amount of atezolizumab.

Embodiment P4

The method of any one of Embodiments P1-P3, wherein the cancer tumor comprises an elevated level of TILs relative to a control.

Embodiment P5

The method of Embodiment P4, wherein the TILs are tumor infiltrating T cells.

Embodiment P6

The method of Embodiment P5, wherein the T cells are CD8 T cells.

Embodiment P7

The method of Embodiment P6, wherein at least about 4% of the cells in a region of the tumor are CD8 T cells.

Embodiment P8

The method of Embodiment P7, wherein the region is the center of the cancer tumor.

Embodiment P9

The method of Embodiment P5, wherein the T cells are effector memory T cells.

Embodiment P10

The method of Embodiment P9, wherein elevated level of TILs comprises an elevated level of the number of TILs and/or an elevated TIL activity.

Embodiment P11

The method of any one of Embodiments P1-P10, wherein a biological sample obtained from the subject comprises increased T cell receptor diversity relative to a control.

Embodiment P12

The method of Embodiment P11, wherein the subject has a peripheral blood clonality of less than about 0.3.

Embodiment P13

The method of any one of Embodiments P1-P12, wherein the cancer tumor comprises an elevated level of PD-L1 relative to a control.

Embodiment P14

The method of Embodiment P13, wherein the cancer tumor comprises an elevated level of PD-L1 in TILs relative to a control.

Embodiment P15

The method of Embodiment P13, wherein the cancer tumor comprises an elevated level of PD-L1 in all tumor cells relative to a control.

Embodiment P16

The method of any one of Embodiments P1-P15, wherein the T-effector signature is the level of expression of any combination of 2, 3, 4, 5, 6, 7, 8, 9, 10, 11, 12, 13, 14, 15, 16, 17, or 18 of CD8a, CXCL9, CXCL10, EOMES, IFNγ, GZMA, GZMB, TBX21, CXCL16, PD-L2, CKLF, OPG, ICAM1, Eotaxin, CCL13, L2Ra, IL7R, and CD44.

Embodiment P17

The method of any one of Embodiments P1-P16, wherein the cancer tumor comprises an elevated level of CD73 relative to a control.

Embodiment P18

The method of any one of Embodiments P1-P17, wherein the blood of the subject comprises an elevated level of CD73 relative to a control.

Embodiment P19

The method of any one of Embodiments P1-P18, wherein the subject comprises an elevated level of TILs relative to a control, the subject comprises an increased cancer tumor T cell receptor diversity or blood T cell receptor diversity relative to a control, the cancer tumor comprises an elevated level of PD-L1 relative to a control, or the cancer tumor or the blood of the subject comprises an elevated level of CD73 relative to a control prior to administration of the A2A receptor antagonist.

Embodiment P20

The method of any one of Embodiments P1-P18, wherein subject comprises an elevated level of TILs relative to a control, the subject comprises an increased cancer tumor T cell receptor diversity or blood T cell receptor diversity relative to a control, or the cancer tumor comprises an elevated level of PD-L1 relative to a control, or the cancer tumor or the blood of the subject comprises an elevated level of CD73 relative to a control, after administration of the A2A receptor antagonist.

Embodiment P21

The method of Embodiment P3, wherein the A2A receptor antagonist and the atezolizumab are administered in a combined synergistic amount.

Embodiment P22

The method of any one of Embodiments P1-P21, wherein the A2A receptor antagonist is CPI-444.

Embodiment P23

The method of any one of Embodiments P1-P22, wherein the A2A receptor antagonist is administered at 100 mg.

Embodiment P24

The method of any one of Embodiments P1-P20, wherein the A2A receptor antagonist is administered twice a day (BID).

Embodiment P25

The method of any one of Embodiments P3-P24, wherein the atezolizumab is administered at 840 mg.

Embodiment P26

The method of any one of Embodiments P3-P25, wherein the atezolizumab is administered once every two weeks (Q2W).

Embodiment P27

The method of any one of Embodiments P3-P24 or P26, wherein the atezolizumab is administered at 1200 mg.

Embodiment P28

The method of any one of Embodiments P3-P27, wherein the atezolizumab is administered once every three weeks (Q3W).

Embodiment P29

The method of any one of Embodiments P1-P28, wherein the cancer is colon cancer, lung cancer, triple negative breast cancer, melanoma, head and neck cancer, prostate cancer, bladder cancer or renal cancer.

Embodiment P30

The method of any one of Embodiments P1-P29, wherein the cancer is colon cancer.

Embodiment P31

The method of any one of Embodiments P1-P25, wherein the cancer is lung cancer.

Embodiment P32

A method of treating a cancer tumor in a subject in need thereof, the method comprising: (i) determining whether (a) the cancer tumor comprises elevated levels of tumor infiltrating lymphocytes (TILs) relative to a control, (b) the subject comprises an increased cancer tumor T cell receptor diversity or blood T cell receptor diversity relative to a control, (c) the cancer tumor comprises an elevated level of PD-L1 relative to a control, (d) the subject has an increased level of a T-effector signature compared to a control, or (e) the cancer tumor or blood of the subject comprises an elevated level of CD73 relative to a control; and (ii) administering to the subject a therapeutically effective amount of an adenosine-A2A receptor antagonist.

Embodiment P33

The method of Embodiment P32, wherein determining whether (a) the cancer tumor comprises elevated levels of tumor infiltrating lymphocytes (TILs) relative to a control, (b) the subject comprises an increased cancer tumor T cell receptor diversity or blood T cell receptor diversity relative to a control, (c) the cancer tumor comprises an elevated level of PD-L1 relative to a control, (d) the subject has an increased level of a T-effector signature compared to a control, or (e) the cancer tumor or the blood of the subject comprises an elevated level of CD73 relative to a control comprises obtaining a biological sample from the subject.

Embodiment P34

The method of Embodiment P33, wherein the biological sample comprises a tumor biopsy, blood, serum, or plasma.

Embodiment P35

The method of any one of Embodiments P32-P34, wherein determining whether the cancer tumor comprises elevated levels of TILs comprises detecting a T-effector signature.

Embodiment P36

The method of Embodiment P35, wherein the T-effector signature is the level of expression of any combination of 2, 3, 4, 5, 6, 7, 8, 9, 10, 11, 12, 13, 14, 15, 16, 17, or 18 of CD8a, CXCL9, CXCL10, EOMES, IFNγ, GZMA, GZMB, TBX21, CXCL16, PD-L2, CKLF, OPG, ICAM1, Eotaxin, CCL13, IL2Ra, L7R, and CD44 compared to a control.

Embodiment P37

The method of any one of Embodiments P32-P36, wherein the A2A receptor antagonist is a compound of formula:

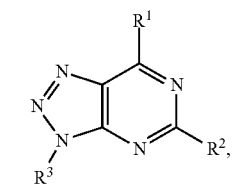

(I)

wherein the substituents are as defined in Embodiment P2.

Embodiment P38

The method of any one of Embodiments P32-P37, further comprising administering to the subject a therapeutically effective amount of atezolizumab.

Embodiment P39

The method of any one of Embodiments P32-P38, wherein the cancer tumor has an elevated level of TILs relative to a control.

Embodiment P40

The method of Embodiment P39, wherein the TILs are tumor infiltrating T cells.

Embodiment P41

The method of Embodiment P40, wherein the T cells are CD8 T cells.

Embodiment P42

The method of Embodiment P41, wherein at least about 4% of the cells in a region of the tumor are CD8 T cells.

Embodiment P43

The method of Embodiment P42, wherein the region is the center of the cancer tumor.

Embodiment P44

The method of any one of Embodiments P32-P43, wherein the cancer is colon cancer, lung cancer, triple negative breast cancer, melanoma, head and neck cancer, prostate cancer, bladder cancer, or renal cancer.

Embodiment P45

The method of any one of Embodiments P1-P44, wherein the subject is a refractory subject.

Embodiment P46

The method of Embodiment P45, wherein the refractory subject has had less than 5% reduction in tumor volume after administration of anti-PD-1 compound.

Embodiment P47

The method of Embodiment P45, wherein the refractory subject has a tumor that has increased in volume after administration of an anti-PD-1 compound.

Embodiment P48

The method of Embodiment P46, wherein the anti-PD-1 compound is atezolizumab.

Embodiment P49

The method of any one of Embodiments P1-P48, wherein the subject has nivolumab refractory renal cancer.

Embodiment P50

The method of any one of Embodiments P1-P49, wherein the cancer is resistant to pembrolizumab, a tyrosine kinase inhibitor, or an mTOR inhibitor.

Embodiment P51

A method of treating nivolumab refractory cancer in a subject in need thereof, the method comprising administering to the subject a therapeutically effective amount of an adenosine A2A receptor antagonist.

Embodiment P52

The method of Embodiment P50, wherein the nivolumab refractory cancer is nivolumab refractory renal cell cancer.

Embodiment P53

The method of any one of Embodiment P51 or P52, wherein the nivolumab refractory cancer is also refractory to a tyrosine kinase inhibitor or an mTOR inhibitor.

Embodiment P54

A method of treating cancer that is wherein the cancer is resistant to pembrolizumab, a tyrosine kinase inhibitor, or an mTOR inhibitor in a subject in need thereof, the method comprising administering to the subject a therapeutically effective amount of an adenosine-A2A receptor antagonist.

Embodiment P55

The method of Embodiment P54, wherein the cancer that is resistant to pembrolizumab, a tyrosine kinase inhibitor, or an mTOR inhibitor is renal cell carcinoma that is resistant to pembrolizumab, a tyrosine kinase inhibitor, or an mTOR inhibitor.

EXAMPLES

Embodiments herein are further illustrated by the following examples. However, the examples are merely intended to illustrate embodiments and are not to be construed to limit the scope herein.

Inhibition of A2AR induces anti-tumor immunity alone and in combination with anti-PD-L1 in preclinical and clinical studies.

Anti-PD-(L)1 antibodies are approved in the treatment of renal cell carcinoma (RCC) and non-small cell lung cancer (NSCLC), but only a minority of patients respond or achieve long-term disease control. There are no approved therapies that can overcome resistance to anti-PD-(L)1 therapies. Few, if any immunotherapies, have reported benefit in the PD-1 resistant/refractory setting. Approaches for converting tumors devoid of T cell infiltration ("cold tumors") into T cell inflamed tumors ("hot tumors") have not been established. Adenosine represents an emerging mediator of immunosuppression within the tumor microenvironment. CPI-444 is an oral small molecule antagonist of the adenosine A2A receptor (A2AR).

Adenosine signaling via A2A receptor (A2AR) on immune cells suppresses anti-tumor immunity and limits the efficacy of immunotherapy, chemotherapy, CAR-T, and vaccines. CPI-444 is a potent and selective oral A2AR antagonist. Daily treatment of mice with CPI-444 led to dose-dependent inhibition of tumor growth in multiple syngeneic tumor models. Combining CPI-444 with anti-PD-L1 treatment synergistically eliminated tumors in up to 90% of treated mice, including restoration of immune responses in models that are poorly responsive to anti-PD-1 or anti-PD-L1 monotherapy. A Phase 1/1b clinical trial has been initiated to examine safety, tolerability, biomarkers, and preliminary efficacy of CPI-444 as a single agent and in combination with the anti-PD-L1 antibody, atezolizumab, in patients with non-small cell lung, melanoma, renal, triple negative breast, and other (bladder, prostate, head and neck, colorectal) tumors. Step 1 of the trial focused on determining the optimal dose and schedule for CPI-444; Step 2 is currently evaluating the efficacy of optimal CPI-444 dosing alone and with atezolizumab. In 48 patients treated in Step 1, CPI-444 was well tolerated with 1 Grade 3 or 4 treatment related adverse events. Evidence of clinical activity was observed in patients treated with single agent CPI-444, including patients who previously failed anti-PD-1 therapy. In embodiments, CD73 expression, CD8 infiltration, TREG distribution, and gene expression signatures are evaluated in serial tumor biopsy specimens. CPI-444 is well tolerated in cancer patients, exhibits functional inhibition of adenosine signaling, and treatment is associated with activation of anti-tumor immunity and clinical activity.

In embodiments, pre-existing T cell infiltration or activation is not required for tumor regression with either single agent or combination regimens. In embodiments, inhibition of A2AR signaling stimulates T cell infiltration and activation in the tumor microenvironment in both inflamed and non-inflamed tumors.

While various embodiments and aspects of the disclosure are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments described herein may be employed.

References: Antonioli et al, Nat Rev Cancer. 2013 December; 13(12):842-57; Blank et al, Cancer Immunol Immunother 2005; 54:307-14; Blank et al, Cancer Immunol Immunother 2007; 56:739-45; Chalmin et al, Immunity. 2012; 36(3):362-73; Csoka et al, FASEB J. 2008; 22(10): 3491-9; D'Addio et al, J Immunol 2011; 187:4530-41; Gao et al, Biomed Res Int. 2014; 2014:4606-54; Guleria et al, J Exp Med 2005; 202:231-7; Habicht et al, J Immunol 2007; 179:5211-9; Hasko et al, Nat Rev Drug Discov. 2008; 7(9):759-70; Herbst et al, Nature 2014; 515:563-7; Hodi et al, N Engl J Med 2010; 363:711-23; Iwai et al, Proc Natl Acad Sci USA 2002; 99:12293-7; Keir et al, Annual Rev Immunol 2008; 26:677-704; Loi et al, Proc Natl Acad Sci USA 2013; 110(27):11091-6; Marzec et al, Proc Natl Acad Sci USA. 2008 Dec. 30; 105(52):20852-7; Mittal et al, Cancer Research. 2014; 74(14):3652-8; Ohta et al, Proc Natl Acad Sci USA. 2006; 103(35):13132-7; Raskovalova et al, J Immunol. 2005; 175(7):4383-91; Schadendorf et al, Eur Cancer Congress 2013 LBA24; Sica, Exp Oncol. 2010; 32(3):153-8; Stagg et al, Proc Natl Acad Sci USA. 2010; 107(4):1547-52; Stagg et al, Proc Natl Acad Sci USA 2011; 108:7142-7; Strome et al, Cancer Res 2003; 63:6501-5; Waickman et al, Cancer Immunol Immunother. 2012; 61(6): 917-26.

What is claimed is:

1. A method of treating a cancer tumor in a subject in need thereof, the method comprising administering to the subject a therapeutically effective amount of an adenosine-A2A receptor antagonist, wherein:

the cancer tumor or blood of the subject comprises an elevated level of CD73 relative to a control;

(ii) the cancer tumor comprises an elevated level of tumor infiltrating lymphocytes relative to a control;

(iii) the subject comprises an increased cancer tumor T cell receptor diversity or blood T cell receptor diversity relative to a control;

(vi) the subject has an increased level of a T-effector signature compared to a control; or (v) a combination of two or more of the foregoing.

2. The method of claim 1, wherein the adenosine-A2A receptor antagonist is a compound of formula (I):

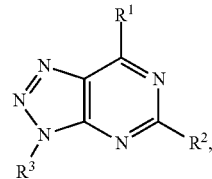

wherein: $R^1$ is independently hydrogen, halogen, $-CX^a_3$, $-CN$, $-SO_2Cl$, $-SO_{n_1}R^9$, $-SO_{v_1}NR^9R^{10}$, $-NHNH_2$, $-ONR^9R^{10}$, $-NHC=(O)NHNH_2$, $-NHC=(O)NR^9R^{10}$, $-N(O)_{m_1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, halogen, $-CX^b_3$, $-CN$, $-SO_2Cl$, $-SO_2R^{11}$, $-SO_{v_2}R^{11}R^{12}$, $-NHNH_2$, $-ONR^{11}R^{12}$, $-NHC=(O)NHNH_2$, $-NHC=(O)NR^{11}R^{12}$, $-N(O)_{m_2}$, $-NR^{11}R^{12}$, $-NH-O-R^{11}$, $-C(O)R^{11}$, $-C(O)-OR^9$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, halogen, $-CX^c_3$, $-CN$, $-SO_2Cl$, $-SO_{n_3}R^{13}$, $-SO_{v_3}NR^{13}R^{14}$, $-NHNH_2$, $-ONR^{13}R^{14}$, $-NHC=(O)NHNH_2$, $-NHC=(O)NR^{13}R^{14}$, $-N(O)_{m_3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$, $R^{10}$, $R^{11}$, $R^{12}$, $R^{13}$ and $R^{14}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $X^a$, $X^b$ and $X^c$ are independently $-F$, $-Cl$, $-Br$, or $-I$; $n_1$, $n_2$ and $n_3$ are independently an integer from 0 to 4; $m_1$, $m_2$ and $m_3$ are independently an integer from 1 to 2; and $v_1$, $v_2$ and $v_3$ are independently an integer from 1 to 2.

3. The method of claim 1, wherein the adenosine-A2A receptor antagonist is a compound of formula (III):

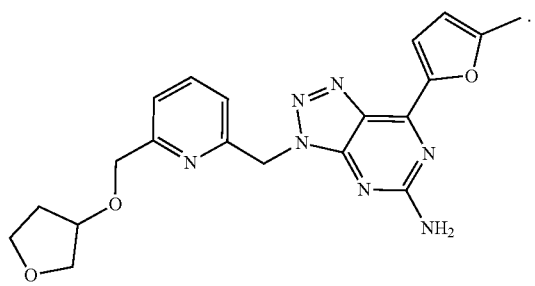

4. The method of claim 1, wherein the adenosine-A2A receptor antagonist is a compound of formula (IIIA) or (IIIB):

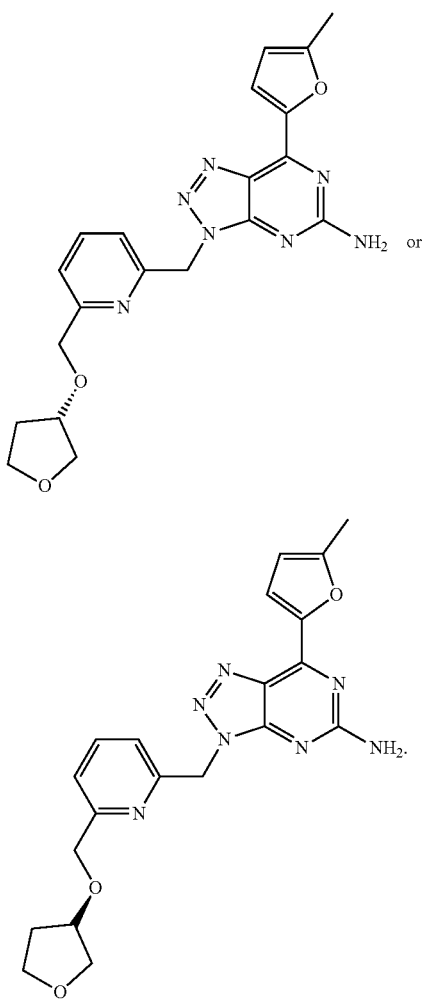

5. The method of claim 1 further comprising administering to the subject a therapeutically effective amount of a PD-1 signaling pathway inhibitor.

6. The method of claim 5, wherein the PD-1 signaling pathway inhibitor is atezolizumab.

7. The method of claim 1 wherein the cancer tumor or the blood of the subject comprises an elevated level of CD73 relative to a control.

8. The method of claim 1, wherein the cancer tumor comprises an elevated level of tumor infiltrating lymphocytes relative to a control.

9. The method of claim 8, wherein elevated level of tumor infiltrating lymphocytes comprise: (i) an elevated level of the number of tumor infiltrating lymphocytes; (ii) an elevated tumor infiltrating lymphocyte activity; or (iii) an elevated level of the number of tumor infiltrating lymphocytes and an elevated tumor infiltrating lymphocyte activity.

10. The method of claim 1, wherein a biological sample obtained from the subject comprises increased T cell receptor diversity relative to a control.

11. The method of claim 1, wherein the cancer tumor further comprises: (i) an elevated level of PD-L1 relative to a control; (ii) an elevated level of PD-L1 in tumor infiltrating lymphocytes relative to a control; or (iii) an elevated level of PD-L1 in all tumor cells relative to a control.

12. The method of claim 1 wherein the subject has an increased level of a T-effector signature compared to a control.

13. The method of claim 12, wherein the T-effector signature is the level of expression of any combination of 2, 3, 4, 5, 6, 7, 8, 9, 10, 11, 12, 13, 14, 15, 16, 17, or 18 of CD8a, CXCL9, CXCL10, EOMES, IFNγ, GZMA, GZMB, TBX21, CXCL16, PD-L2, CKLF, OPG, ICAM1, eotaxin, CCL13, IL2Ra, IL7R, and CD44.

14. The method of claim 1 wherein the subject comprises an increased cancer tumor or blood T cell receptor diversity relative to a control.

15. The method of claim 1, wherein the cancer is colon cancer, non-small cell lung cancer, triple negative breast cancer, melanoma, head and neck cancer, colorectal cancer, prostate cancer, bladder cancer, or renal cancer.

* * * * *